(12) United States Patent
Goble et al.

(10) Patent No.: US 8,556,936 B2
(45) Date of Patent: Oct. 15, 2013

(54) FACET JOINT REPLACEMENT

(75) Inventors: Eugene Marlowe Goble, Logan, UT (US); Thomas Wade Fallin, Hyde Park, UT (US); Robert W. Hoy, Columbus, OH (US); Daniel F. Justin, Logan, UT (US); Alan Chervitz, Palm Harbor, FL (US); Jude Paganelli, San Diego, CA (US); Daniel J. Triplett, Providence, UT (US)

(73) Assignee: GMEDELAWARE 2 LLC, Audubon, PA (US)

( * ) Notice: Subject to any disclaimer, the term of this patent is extended or adjusted under 35 U.S.C. 154(b) by 1217 days.

(21) Appl. No.: 11/670,292

(22) Filed: Feb. 1, 2007

(65) Prior Publication Data
US 2007/0270967 A1    Nov. 22, 2007

Related U.S. Application Data

(63) Continuation of application No. 10/687,865, filed on Oct. 17, 2003, now abandoned, which is a continuation-in-part of application No. 10/421,078, filed on Apr. 23, 2003, now Pat. No. 7,041,136, which is a continuation of application No. 09/726,169, filed on Nov. 29, 2000, now Pat. No. 6,579,319.

(60) Provisional application No. 60/505,199, filed on Sep. 23, 2003.

(51) Int. Cl.
*A61B 17/70* (2006.01)
*A61B 17/88* (2006.01)

(52) U.S. Cl.
USPC .......................................... 606/247; 606/279

(58) Field of Classification Search
USPC ............. 606/279, 246–248; 623/17.11–17.16
See application file for complete search history.

(56) References Cited

U.S. PATENT DOCUMENTS

| | | | |
|---|---|---|---|
| 3,486,505 A | 12/1969 | Morrison | |
| 3,508,954 A | 4/1970 | White | |
| 3,857,642 A | 12/1974 | Miller | |
| 4,092,078 A | 5/1978 | Klotz et al. | |
| 4,289,123 A | 9/1981 | Dunn | |
| 4,483,334 A | 11/1984 | Murray | |

(Continued)

FOREIGN PATENT DOCUMENTS

| CN | 2386790 Y | 7/2000 |
|---|---|---|
| EP | 408489 A1 | 1/1991 |

(Continued)

OTHER PUBLICATIONS

Anres; Todd, *A Glimpse of the Future of Spine Technology*, Facet Joint Arthroplasty, Orthopaedic Product News, Sep./Oct. 2005 p. 38-40.

*Primary Examiner* — Matthew Lawson

(57) ABSTRACT

A prosthesis for the replacement of at least a portion of the bone of a facet located on a mammalian vertebra, comprising: an articulating surface that articulates with another facet; a bone contacting surface that contacts a surface of the vertebra, the articulating surface being connected to the bone contacting surface; and a fixation element that attaches the bone contacting surface to the vertebra, the fixation element being adapted for implantation into an interior bone space of a pedicle of the vertebra; wherein the prosthesis is configured so that no portion of the prosthesis contacts the posterior arch of the vertebra.

15 Claims, 48 Drawing Sheets

(56) References Cited

U.S. PATENT DOCUMENTS

| | | | |
|---|---|---|---|
| 4,501,269 A | 2/1985 | Bagby | |
| 4,604,995 A | 8/1986 | Stephens et al. | |
| 4,611,581 A | 9/1986 | Steffee | |
| 4,641,636 A | 2/1987 | Cotrel | |
| 4,657,550 A | 4/1987 | Daher | |
| 4,696,290 A | 9/1987 | Steffee | |
| 4,790,303 A | 12/1988 | Steffee | |
| 4,800,874 A | 1/1989 | David et al. | |
| 4,805,602 A | 2/1989 | Puno et al. | |
| 4,827,918 A | 5/1989 | Olerud | |
| 4,863,476 A | 9/1989 | Shepperd | |
| 4,946,458 A | 8/1990 | Harms et al. | |
| 5,011,484 A | 4/1991 | Breard | |
| 5,092,866 A | 3/1992 | Breard et al. | |
| 5,092,867 A | 3/1992 | Harms et al. | |
| 5,127,912 A | 7/1992 | Ray et al. | |
| 5,147,361 A | 9/1992 | Ojima et al. | |
| 5,246,458 A | 9/1993 | Graham | |
| 5,261,910 A | 11/1993 | Warden et al. | |
| 5,263,953 A | 11/1993 | Bagby | |
| 5,282,863 A | 2/1994 | Burton | |
| 5,306,275 A * | 4/1994 | Bryan | 606/914 |
| 5,313,962 A | 5/1994 | Obenchain | |
| 5,366,455 A * | 11/1994 | Dove et al. | 606/250 |
| 5,387,213 A | 2/1995 | Breard et al. | |
| 5,391,168 A * | 2/1995 | Sanders et al. | 606/253 |
| 5,415,661 A | 5/1995 | Holmes | |
| 5,437,669 A | 8/1995 | Yuan et al. | |
| 5,439,464 A | 8/1995 | Shapiro | |
| 5,443,516 A | 8/1995 | Albrektsson et al. | |
| 5,464,439 A | 11/1995 | Gendler | |
| 5,470,333 A | 11/1995 | Ray | |
| 5,476,463 A | 12/1995 | Boachie-Adjei et al. | |
| 5,480,401 A | 1/1996 | Navas | |
| 5,489,308 A | 2/1996 | Kuslich et al. | |
| 5,507,745 A | 4/1996 | Logroscino et al. | |
| 5,507,813 A | 4/1996 | Dowd et al. | |
| 5,522,899 A | 6/1996 | Michelson | |
| 5,531,745 A | 7/1996 | Ray | |
| 5,531,747 A | 7/1996 | Ray | |
| 5,549,607 A | 8/1996 | Olson et al. | |
| 5,556,687 A | 9/1996 | McMillin | |
| 5,562,735 A | 10/1996 | Margulies | |
| 5,562,736 A | 10/1996 | Ray et al. | |
| 5,562,737 A | 10/1996 | Graf | |
| 5,569,248 A | 10/1996 | Mathews | |
| 5,571,191 A * | 11/1996 | Fitz | 623/17.11 |
| 5,582,612 A | 12/1996 | Lin | |
| 5,584,832 A | 12/1996 | Schlapfer | |
| 5,603,713 A | 2/1997 | Aust et al. | |
| 5,649,926 A | 7/1997 | Howland | |
| 5,666,243 A | 9/1997 | Brent | |
| 5,672,175 A | 9/1997 | Martin | |
| 5,681,310 A | 10/1997 | Yuan et al. | |
| 5,683,465 A | 11/1997 | Shinn et al. | |
| 5,688,272 A | 11/1997 | Montague et al. | |
| 5,690,629 A | 11/1997 | Asher et al. | |
| 5,704,936 A | 1/1998 | Mazel | |
| 5,735,899 A | 4/1998 | Schwartz et al. | |
| 5,749,873 A | 5/1998 | Fairley | |
| 5,772,661 A | 6/1998 | Michelson | |
| 5,797,909 A | 8/1998 | Michelson | |
| 5,814,046 A | 9/1998 | Hopf | |
| 5,836,948 A | 11/1998 | Zucherman et al. | |
| 5,860,977 A | 1/1999 | Zucherman et al. | |
| 5,876,404 A | 3/1999 | Zucherman et al. | |
| RE36,221 E | 6/1999 | Breard et al. | |
| 5,961,516 A | 10/1999 | Graf | |
| 5,986,169 A | 11/1999 | Gjunter | |
| 6,004,322 A | 12/1999 | Bernstein | |
| 6,019,759 A | 2/2000 | Rogozinski | |
| 6,039,761 A | 3/2000 | Li et al. | |
| 6,048,342 A | 4/2000 | Zucherman et al. | |
| 6,063,088 A | 5/2000 | Winslow | |
| 6,066,325 A | 5/2000 | Wallace et al. | |
| 6,074,390 A | 6/2000 | Zucherman et al. | |
| 6,090,112 A | 7/2000 | Zucherman et al. | |
| 6,113,639 A | 9/2000 | Ray et al. | |
| 6,132,464 A * | 10/2000 | Martin | 623/17.15 |
| 6,149,652 A | 11/2000 | Zucherman et al. | |
| 6,151,934 A | 11/2000 | Chong et al. | |
| 6,152,926 A | 11/2000 | Zucherman et al. | |
| 6,156,038 A | 12/2000 | Zucherman et al. | |
| 6,176,861 B1 | 1/2001 | Bernstein et al. | |
| 6,179,838 B1 | 1/2001 | Fiz | |
| 6,190,414 B1 | 2/2001 | Young et al. | |
| 6,206,882 B1 | 3/2001 | Cohen | |
| 6,206,922 B1 | 3/2001 | Zdeblick et al. | |
| 6,238,397 B1 | 5/2001 | Zucherman et al. | |
| 6,241,730 B1 | 6/2001 | Alby | |
| 6,264,655 B1 | 7/2001 | Pisharodi | |
| 6,267,764 B1 | 7/2001 | Elberg | |
| 6,280,444 B1 | 8/2001 | Zucherman et al. | |
| 6,290,700 B1 | 9/2001 | Schmotzer | |
| 6,293,949 B1 | 9/2001 | Justis et al. | |
| 6,312,469 B1 | 11/2001 | Gielen et al. | |
| 6,314,325 B1 | 11/2001 | Fitz | |
| 6,332,882 B1 | 12/2001 | Zucherman et al. | |
| 6,379,355 B1 | 4/2002 | Zucherman et al. | |
| 6,413,259 B1 | 7/2002 | Lyons et al. | |
| 6,419,676 B1 | 7/2002 | Zucherman et al. | |
| 6,419,677 B2 | 7/2002 | Zucherman et al. | |
| 6,419,703 B1 * | 7/2002 | Fallin et al. | 623/17.11 |
| 6,419,704 B1 | 7/2002 | Ferree | |
| 6,440,169 B1 | 8/2002 | Elberg et al. | |
| 6,447,546 B1 | 9/2002 | Bramlet et al. | |
| 6,451,020 B1 | 9/2002 | Zucherman et al. | |
| 6,461,359 B1 | 10/2002 | Tribus et al. | |
| 6,471,704 B2 | 10/2002 | Gertzbein et al. | |
| 6,475,219 B1 | 11/2002 | Shelokov | |
| 6,478,796 B2 | 11/2002 | Zucherman et al. | |
| 6,481,440 B2 | 11/2002 | Gielen et al. | |
| 6,500,178 B2 | 12/2002 | Zucherman et al. | |
| 6,514,256 B2 | 2/2003 | Zucherman et al. | |
| 6,527,806 B2 | 3/2003 | Ralph et al. | |
| 6,565,605 B2 * | 5/2003 | Goble et al. | 623/17.11 |
| 6,579,319 B2 * | 6/2003 | Goble et al. | 623/17.11 |
| 6,582,433 B2 | 6/2003 | Yun | |
| 6,585,769 B1 | 7/2003 | Muhanna et al. | |
| 6,610,091 B1 * | 8/2003 | Reiley | 623/17.11 |
| 6,616,669 B2 | 9/2003 | Ogilvie et al. | |
| 6,626,909 B2 | 9/2003 | Chin | |
| 6,626,944 B1 | 9/2003 | Taylor | |
| 6,652,527 B2 | 11/2003 | Zucherman et al. | |
| 6,652,534 B2 | 11/2003 | Zucherman et al. | |
| 6,652,585 B2 | 11/2003 | Lange | |
| 6,669,729 B2 * | 12/2003 | Chin | 623/17.11 |
| 6,695,842 B2 | 2/2004 | Zucherman et al. | |
| 6,699,246 B2 | 3/2004 | Zucherman et al. | |
| 6,699,247 B2 | 3/2004 | Zucherman et al. | |
| 6,733,534 B2 | 5/2004 | Sherman | |
| 6,761,719 B2 | 7/2004 | Justis et al. | |
| 6,761,720 B1 | 7/2004 | Senegas | |
| 6,783,527 B2 | 8/2004 | Drewry et al. | |
| 6,796,983 B1 | 9/2004 | Zucherman et al. | |
| 6,811,567 B2 * | 11/2004 | Reiley | 623/17.11 |
| 6,835,205 B2 | 12/2004 | Atkinson et al. | |
| 6,835,207 B2 | 12/2004 | Zacouto et al. | |
| 7,087,084 B2 | 8/2006 | Reiley | |
| 7,090,698 B2 * | 8/2006 | Goble et al. | 623/17.11 |
| 7,101,398 B2 * | 9/2006 | Dooris et al. | 623/13.11 |
| 7,147,664 B2 * | 12/2006 | Louis et al. | 623/17.11 |
| 7,338,490 B2 * | 3/2008 | Ogilvie et al. | 606/276 |
| 7,371,238 B2 * | 5/2008 | Soboleski et al. | 606/246 |
| 2001/0007073 A1 | 7/2001 | Zucherman et al. | |
| 2001/0012938 A1 | 8/2001 | Zucherman et al. | |
| 2001/0016743 A1 | 8/2001 | Zucherman et al. | |
| 2001/0021850 A1 | 9/2001 | Zucherman et al. | |
| 2001/0031965 A1 | 10/2001 | Zucherman et al. | |
| 2001/0039452 A1 | 11/2001 | Zucherman et al. | |
| 2002/0029039 A1 | 3/2002 | Zucherman et al. | |
| 2002/0065557 A1 * | 5/2002 | Goble et al. | 623/17.11 |
| 2002/0072800 A1 * | 6/2002 | Goble et al. | 623/17.11 |
| 2002/0091446 A1 | 7/2002 | Zucherman et al. | |

(56) References Cited

U.S. PATENT DOCUMENTS

| | | |
|---|---|---|
| 2002/0116000 A1 | 8/2002 | Zucherman et al. |
| 2002/0143331 A1 | 10/2002 | Zucherman et al. |
| 2002/0183746 A1 | 12/2002 | Zucherman et al. |
| 2003/0009226 A1 | 1/2003 | Graf |
| 2003/0028250 A1* | 2/2003 | Reiley et al. ............... 623/17.11 |
| 2003/0055427 A1 | 3/2003 | Graf |
| 2003/0065330 A1 | 4/2003 | Zucherman et al. |
| 2003/0073998 A1 | 4/2003 | Pagliuca et al. |
| 2003/0109880 A1 | 6/2003 | Shirado et al. |
| 2003/0153912 A1 | 8/2003 | Graf |
| 2003/0191470 A1 | 10/2003 | Ritland |
| 2003/0220642 A1 | 11/2003 | Freudiger |
| 2003/0220643 A1 | 11/2003 | Ferree |
| 2004/0006341 A1 | 1/2004 | Shaolian et al. |
| 2004/0006391 A1 | 1/2004 | Reiley |
| 2004/0009232 A1 | 1/2004 | Reiner |
| 2004/0024458 A1 | 2/2004 | Senegas et al. |
| 2004/0049189 A1 | 3/2004 | Le Couedic et al. |
| 2004/0049190 A1 | 3/2004 | Biedermann et al. |
| 2004/0049272 A1 | 3/2004 | Reiley |
| 2004/0049273 A1 | 3/2004 | Reiley |
| 2004/0049274 A1 | 3/2004 | Reiley |
| 2004/0049275 A1 | 3/2004 | Reiley |
| 2004/0049276 A1 | 3/2004 | Reiley |
| 2004/0049277 A1 | 3/2004 | Reiley |
| 2004/0049278 A1 | 3/2004 | Reiley |
| 2004/0049281 A1 | 3/2004 | Reiley |
| 2004/0073215 A1 | 4/2004 | Carli |
| 2004/0078082 A1 | 4/2004 | Lange |
| 2004/0082954 A1 | 4/2004 | Teitelbaum et al. |
| 2004/0087950 A1 | 5/2004 | Teitelbaum |
| 2004/0106995 A1 | 6/2004 | Le Couedic et al. |
| 2004/0111154 A1 | 6/2004 | Reiley |
| 2004/0116927 A1 | 6/2004 | Graf |
| 2004/0117017 A1 | 6/2004 | Pasquet et al. |
| 2004/0127989 A1 | 7/2004 | Dooris et al. |
| 2004/0143264 A1 | 7/2004 | Mcafee |
| 2004/0147928 A1 | 7/2004 | Landry et al. |
| 2004/0153071 A1 | 8/2004 | Zucherman et al. |
| 2004/0158245 A1 | 8/2004 | Chin |
| 2004/0167520 A1 | 8/2004 | Zucherman et al. |
| 2004/0172025 A1 | 9/2004 | Drewry et al. |
| 2004/0181282 A1 | 9/2004 | Zucherman et al. |
| 2004/0181285 A1 | 9/2004 | Simonson |
| 2004/0186475 A1 | 9/2004 | Falahee |
| 2004/0220568 A1 | 11/2004 | Zucherman et al. |
| 2004/0225289 A1 | 11/2004 | Biedermann et al. |
| 2004/0230192 A1 | 11/2004 | Graf |
| 2004/0230201 A1 | 11/2004 | Yuan et al. |
| 2004/0230304 A1 | 11/2004 | Yuan et al. |
| 2004/0236327 A1 | 11/2004 | Paul et al. |
| 2004/0236328 A1 | 11/2004 | Paul et al. |
| 2004/0236329 A1 | 11/2004 | Panjabi |
| 2004/0243239 A1 | 12/2004 | Taylor |
| 2005/0010291 A1 | 1/2005 | Stinson et al. |
| 2005/0010293 A1 | 1/2005 | Zucherman et al. |
| 2005/0010298 A1 | 1/2005 | Zucherman et al. |
| 2005/0027361 A1 | 2/2005 | Reiley |
| 2005/0033434 A1 | 2/2005 | Berry |
| 2005/0033439 A1 | 2/2005 | Gordon et al. |
| 2005/0043797 A1 | 2/2005 | Lee |
| 2005/0043799 A1 | 2/2005 | Reiley |
| 2005/0113927 A1 | 5/2005 | Malek |
| 2005/0119748 A1 | 6/2005 | Reiley et al. |
| 2005/0131406 A1 | 6/2005 | Reiley et al. |
| 2005/0137705 A1 | 6/2005 | Reiley |
| 2005/0137706 A1 | 6/2005 | Reiley |
| 2005/0143818 A1 | 6/2005 | Yuan et al. |
| 2005/0149190 A1 | 7/2005 | Reiley |
| 2005/0154467 A1 | 7/2005 | Peterman et al. |
| 2005/0171609 A1 | 8/2005 | Humphreys et al. |
| 2009/0088802 A1* | 4/2009 | Fallin .......................... 606/248 |

FOREIGN PATENT DOCUMENTS

| | | |
|---|---|---|
| EP | 322334 B1 | 2/1992 |
| EP | 667127 A1 | 8/1995 |
| EP | 767637 B1 | 11/1998 |
| EP | 768843 B1 | 2/1999 |
| EP | 669109 B1 | 5/1999 |
| EP | 1239785 B1 | 9/2004 |
| EP | 1343424 B1 | 9/2004 |
| EP | 13999078 B1 | 12/2004 |
| FR | 2721501 B1 | 8/1996 |
| JP | 10277070 A2 | 10/1998 |
| SU | 1468543 A1 | 3/1989 |
| SU | 1517953 A1 | 10/1989 |
| WO | WO8707827 A1 | 12/1987 |
| WO | WO9421185 A1 | 9/1994 |
| WO | WO9505784 A1 | 3/1995 |
| WO | WO9505785 A1 | 3/1995 |
| WO | WO9505786 A1 | 3/1995 |
| WO | WO9600049 | 1/1996 |
| WO | WO9822033 A1 | 5/1998 |
| WO | WO9848707 A1 | 11/1998 |
| WO | WO9921500 A1 | 5/1999 |
| WO | WO9921501 A1 | 5/1999 |
| WO | WO0062684 | 10/2000 |
| WO | WO0130248 | 5/2001 |
| WO | WO0145576 A1 | 6/2001 |
| WO | WO0149192 A1 | 7/2001 |
| WO | WO0156489 A1 | 8/2001 |
| WO | WO0164142 A1 | 9/2001 |
| WO | WO0164144 A2 | 9/2001 |
| WO | WO0191657 A1 | 12/2001 |
| WO | WO0191658 A1 | 12/2001 |
| WO | WO0197721 A2 | 12/2001 |
| WO | WO0200124 A1 | 1/2002 |
| WO | WO0203882 A2 | 1/2002 |
| WO | WO0207621 A1 | 1/2002 |
| WO | WO0207622 A1 | 1/2002 |
| WO | WO0207623 A1 | 1/2002 |
| WO | WO0213732 A3 | 2/2002 |
| WO | WO0230336 A2 | 4/2002 |
| WO | WO0234120 A2 | 5/2002 |
| WO | WO0243603 A1 | 6/2002 |
| WO | WO02067792 A2 | 9/2002 |
| WO | WO02067793 A2 | 9/2002 |
| WO | WO02089712 A2 | 11/2002 |
| WO | WO02102259 A2 | 12/2002 |
| WO | WO03009737 A1 | 2/2003 |
| WO | WO03011147 A1 | 2/2003 |
| WO | WO03015646 A2 | 2/2003 |
| WO | WO03045262 A2 | 6/2003 |
| WO | WO03077806 A1 | 9/2003 |
| WO | WO2004017817 A2 | 3/2004 |
| WO | WO2004019762 A2 | 3/2004 |
| WO | WO2004024010 A1 | 3/2004 |
| WO | WO2004032794 A2 | 4/2004 |
| WO | WO2004039239 A2 | 5/2004 |
| WO | WO2004039243 A2 | 5/2004 |
| WO | WO2004041066 A2 | 5/2004 |
| WO | WO2004073533 A1 | 5/2004 |
| WO | WO2004098423 A1 | 11/2004 |
| WO | WO2004098452 A2 | 11/2004 |
| WO | WO2004105577 A2 | 12/2004 |
| WO | WO2004105580 A2 | 12/2004 |
| WO | WO2005013864 | 2/2005 |
| WO | WO2005037149 | 4/2005 |
| WO | WO2005044152 A1 | 5/2005 |
| WO | WO2006102443 | 9/2006 |

* cited by examiner

FACET JOINT REPLACEMENT

CROSS-REFERENCE TO RELATED APPLICATIONS

This application is a continuation of:

Pending prior U.S. patent application Ser. No. 10/687,865, filed Oct. 17, 2003 by E. Marlowe Goble et al. for FACET JOINT REPLACEMENT, which claims the benefit of:

Pending prior U.S. Provisional Patent Application Ser. No. 60/505,199, filed Sep. 23, 2003 by E. Marlowe Goble et al. for FACET JOINT REPLACEMENT.

The foregoing are incorporated herein by reference.

U.S. patent application Ser. No. 10/687,865 is also a continuation-in-part of U.S. patent application Ser. No. 10/421,078, filed Apr. 23, 2003 by E. Marlowe Goble et al. for FACET JOINT REPLACEMENT, which issued as U.S. Pat. No. 7,041,136 on May 9, 2006.

U.S. patent application Ser. No. 10/421,078 is a continuation of U.S. patent application Ser. No. 09/726,169, filed Nov. 29, 2000 by E. Marlowe Goble et al. for FACET JOINT REPLACEMENT, which issued as U.S. Pat. No. 6,579,319 on Jun. 17, 2003.

BACKGROUND OF THE INVENTION

1. The Field of the Invention

The present invention relates to surgical devices and methods to replace a damaged, diseased, or otherwise painful spinal facet joint.

2. The Relevant Technology

Traumatic, inflammatory, metabolic, and degenerative disorders of the spine can produce debilitating pain that can have severe socioeconomic and psychological effects. One of the most common surgical interventions today is arthrodesis, or spine fusion, of one or more motion segments, with approximately 300,000 procedures performed annually in the United States. Clinical success varies considerably, depending upon technique and indications, and consideration must be given to the concomitant risks and complications. For example, Tsantrizos and Nibu have shown that spine fusion decreases function by limiting the range of motion for patients in flexion, extension, rotation, and lateral bending. Furthermore, Khoo and Nagata have shown that spine fusion creates increased stresses and, therefore, accelerated degeneration of adjacent non-fused motion segments. Additionally, pseudoarthrosis, as a result of an incomplete or ineffective fusion, may reduce or even eliminate the desired pain relief for the patient. Finally, the fusion device, whether artificial or biological, may migrate out of the fusion site.

Recently, several attempts have been made to recreate the natural biomechanics of the spine by use of an artificial disc. Artificial discs provide for articulation between vertebral bodies to recreate the full range of motion allowed by the elastic properties of the natural intervertebral disc that directly connects two opposed vertebral bodies.

However, the artificial discs proposed to date do not fully address the mechanics of motion of the spinal column. In addition to the intervertebral disc, posterior elements called the facet joints help to support axial, torsional and shear loads that act on the spinal column. Furthermore, the facet joints are diarthroidal joints that provide both sliding articulation and load transmission features. The effects of their absence as a result of facetectomy was observed by Goh to produce significant decreases in the stiffness of the spinal column in all planes of motion: flexion and extension, lateral bending, and rotation. Furthermore, contraindications for artificial discs include arthritic facet joints, absent facet joints, severe facet joint tropism or otherwise deformed facet joints, as noted by Lemaire.

U.S. Pat. No. Re. 36,758 to Fitz discloses an artificial facet joint where the inferior facet, the mating superior facet, or both, are resurfaced.

U.S. Pat. No. 6,132,464 to Martin discloses a spinal facet joint prosthesis that is supported on the posterior arch of the vertebra. Extending from this support structure are inferior and/or superior blades that replace the cartilage at the facet joint. Like the Fitz design, the Martin prosthesis generally preserves existing bony structures and therefore does not address pathologies that affect the bone of the facets in addition to affecting the associated cartilage. Furthermore, the Martin invention requires a mating condition between the prosthesis and the posterior arch (also known as the lamina) that is a thin base of curved bone that carries all four facets and the spinous process. Since the posterior arch is a very complex and highly variable anatomic surface, it would be very difficult to design a prosthesis that provides reproducible positioning to correctly locate the cartilage-replacing blades for the facet joints.

Another approach to surgical intervention for spinal facets is provided in WO9848717A1 to Villaret. While Villaret teaches the replacement of spine facets, the replacement is interlocked in a manner to immobilize the joint.

Facet joint replacement in conjunction with artificial disc replacements represent a holistic solution to recreating a fully functional motion segment that is compromised due to disease or trauma. Together, facet joint and disc replacement can eliminate all sources of pain, return full function and range of motion, and completely restore the natural biomechanics of the spinal column. Additionally, degenerative or traumatized facet joints may be replaced in the absence of disc replacement when the natural intervertebral disc is unaffected by the disease or trauma.

It would therefore be an improvement in the art to provide a vertebral facet replacement device and method that replaces a bony portion of the facets so as to remove the source of arthritic, traumatic, or other disease mediated pain.

SUMMARY OF THE INVENTION

It is an object of the invention to provide an artificial vertebral facet that replaces the cartilage and a portion of the bone of a facet.

It is a further object of the invention to provide a method for preparing a vertebra for the installation of an artificial vertebral facet.

It is another object to provide a method for replacing a spinal facet.

It is yet another object of the invention to provide a total vertebral facet joint replacement.

In the preferred embodiment, an inferior facet of a superior vertebra is resected at the base of the facet where it connects to the posterior arch. The fin of a prosthetic inferior facet is pressed into the interior bone space of the posterior arch. Alternatively, a tool, such as a broach or punch, may be used to first prepare a space for the fin within the posterior arch.

Alternatively, or in addition, a superior facet of an inferior vertebra that articulates with the inferior facet is resected at the base of the facet where it connects to the pedicle. The post of a prosthetic superior facet is pressed into the interior bone space of the pedicle. Alternatively, a tool, such as a broach or punch, may be used to first prepare a space for the post within the pedicle.

The post and the fin may be porous coated to promote bone ingrowth in order to achieve long term fixation. Long term fixation is provided by a press fit between the post or fin and the internal surface of the bone. The porous coating may carry osteoconductive agents, such as hydroxylapatite, calcium sulfate, or demineralized bone matrix. Alternatively, the porous coating may carry osteoinductive agents, such as bone morphogenic proteins, including rhBMP-2 and rhBMP-7.

Another embodiment of the present invention provides a flange extending from the prosthetic facet. The flange is oriented relative to the body of the prosthesis such that when the flange is placed against the pedicle and in a manner such that the planar surface of the flange is perpendicular to the axis of the pedicle interior bone canal, the articulating surface of the prosthesis will be properly positioned to match the articulating surface of the natural facet. The flange includes a hole for the passage of a fastener to securely attach the prosthesis to the pedicle. The fastener can be a screw, spike, tack, staple, or the like.

In one form of the invention, there is provided a prosthesis for the replacement of at least a portion of the bone of a facet located on a mammalian vertebra, comprising:
an articulating surface that articulates with another facet;
a bone contacting surface that contacts a surface of the vertebra, said articulating surface being connected to said bone contacting surface; and
a fixation element that attaches said bone contacting surface to the vertebra, said fixation element being adapted for implantation into an interior bone space of a pedicle of the vertebra;
wherein said prosthesis is configured so that no portion of said prosthesis contacts the posterior arch of said vertebra.

In another form of the present invention, there is provided a prosthesis for the replacement of at least a portion of the bone of a facet located on a mammalian vertebra, comprising:
an articulating surface that articulates with another facet;
a bone contacting surface that contacts a surface of the vertebra, said articulating surface being connected to said bone contacting surface; and
a fixation element that attaches said bone contacting surface to the vertebra, said fixation element being adapted for implantation into an interior bone space of a pedicle of the vertebra;
wherein said bone contacting surface is configured to engage a resected surface of the vertebra.

In another form of the present invention, there is provided a prosthesis for the replacement of at least a portion of the bone of a facet located on a mammalian vertebra, comprising:
an articulating surface that articulates with another facet;
a bone contacting surface that contacts a surface of the vertebra, said articulating surface being connected to said bone contacting surface; and
as fixation element that attaches said bone contacting surface to the vertebra, said fixation element being adapted for implantation into an interior bone space of a pedicle of the vertebra;
wherein said bone contacting surface has a smaller surface area than said articulating surface.

In another form of the present invention, there is provided a prosthesis for the replacement of at least a portion of the bone of a facet located on a mammalian vertebra, comprising:
an articulating surface that articulates with another facet;
a bone contacting surface that contacts a surface of the vertebra, said articulating surface being connected to said bone contacting surface; and
a fixation element that attaches said bone contacting surface to the vertebra, said fixation element being adapted for implantation into an interior bone space of a pedicle of the vertebra;
wherein said articulating surface comprises a wing ear extending upward from said bone contacting surface.

In another form of the present invention, there is provided a prosthesis for the replacement of at least a portion of the bone of a facet located on a mammalian vertebra, comprising:
an articulating surface that articulates with another facet;
a bone contacting surface that contacts a surface of the vertebra, said articulating surface being connected to said bone contacting surface; and
a fixation element that attaches said bone contacting surface to the vertebra, said fixation element being adapted for implantation into an interior bone space of a pedicle of the vertebra;
wherein said articulating surface is substantially planar and extends adjacent to the pedicle.

In another form of the present invention, there is provided a prosthesis for the replacement of at least a portion of the bone of a facet located on a mammalian vertebra, comprising:
an articulating surface that articulates with another facet;
a bone contacting surface that contacts a surface of the vertebra, said articulating surface being connected to said bone contacting surface; and
a fixation element that attaches said bone contacting surface to the vertebra, said fixation element being adapted for implantation into an interior bone space of a pedicle of the vertebra;
wherein said articulating surface is substantially planar and extends substantially parallel to said fixation element.

In another form of the present invention, there is provided a prosthesis for the replacement of at least a portion of the bone of a facet located on a mammalian vertebra, comprising:
an articulating surface that articulates with another facet;
a bone contacting surface that contacts a surface of the vertebra, said articulating surface being connected to said bone contacting surface; and
a fixation element that attaches said bone contacting surface to the vertebra, said fixation element being adapted for implantation into an interior bone space of a pedicle of the vertebra;
wherein said fixation element clamps said bone contacting surface to a resected surface of the vertebra.

In another form of the present invention, there is provided a prosthesis for the replacement of at least a portion of the bone of a facet located on a mammalian vertebra, comprising:
an articulating element that articulates with another facet;
a bone contacting element that contacts a surface of the vertebra, said articulating element being connected to said bone contacting element; and
a fixation element that attaches said bone contacting element to the vertebra, said fixation element being adapted for implantation into an interior bone space of a pedicle of the vertebra;
wherein said prosthesis is configured so that no portion of said prosthesis contacts the posterior arch of said vertebra.

In another form of the present invention, there is provided a prosthesis for the replacement of at least a portion of the bone of a superior facet located on a mammalian vertebra and for replacement of at least a portion of the bone of an inferior facet located on the same mammalian vertebra, comprising:
a superior articulating element that articulates with another facet;

a superior bone contacting element that contacts one of a surface of the vertebra or another element contacting a surface of the vertebra, said superior articulating element being connected to said superior bone contacting element; and an inferior articulating element that articulates with another facet;

an inferior bone contacting element that contacts one of a surface of the vertebra or another element contacting a surface of the vertebra, said inferior articulating element being connected to said inferior bone contacting element; and a fixation element that attaches said superior bone contacting element and said inferior bone contacting element to the vertebra, said fixation element being adapted for implantation into an interior bone space of a pedicle of the vertebra;

wherein said prosthesis is configured so that no portion of said prosthesis contacts the posterior arch of said vertebra.

In another form of the present invention, there is provided a prosthesis for the replacement of at least a portion of the bone of a superior facet located on a first mammalian vertebra and for replacement of at least a portion of the bone of an inferior facet located on a second mammalian vertebra, comprising:

a superior articulating element that articulates with another facet;

a superior bone contacting element that contacts one of a surface of the first vertebra or another element contacting a surface of the vertebra, said superior articulating element being connected to said superior bone contacting element;

a first fixation element that attaches said superior bone contacting element to the first vertebra, said first fixation element being adapted for implantation into an interior bone space of a pedicle of the vertebra; and an inferior articulating element that articulates with another facet;

an inferior bone contacting element that contacts one of a surface of the second vertebra or another element contacting a surface of the vertebra, said inferior articulating element being connected to said inferior bone contacting element; and a second fixation element that attaches said inferior bone contacting element to the second vertebra, said second fixation element being adapted for implantation into an interior bone space of a pedicle of the vertebra; and wherein said prosthesis is configured so that no portion of said prosthesis contacts the posterior arches of said first and second vertebrae.

In another form of the present invention, there is provided a method for replacing at least a portion of the bone of a facet located on a mammalian vertebra, comprising:

providing:

an articulating surface that articulates with another facet;

a bone contacting surface that contacts a surface of the vertebra, said articulating surface being connected to said bone contacting surface; and a fixation element that attaches said bone contacting surface to the vertebra, said fixation element being adapted for implantation into an interior bone space of a pedicle of the vertebra;

wherein said prosthesis is configured so that no portion of said prosthesis contacts the posterior arch of said vertebra; and positioning said bone contacting surface against a surface of the vertebra; and attaching said bone contacting surface to the vertebra using said fixation element.

In another form of the present invention, there is provided a prosthesis for the replacement of at least a portion of the bone of a facet located on a mammalian vertebra, comprising:

an articulating element that articulates with another facet;

a bone contacting element that contacts a surface of the vertebra or another element contacting a surface of the vertebra, said articulating element being connected to said bone contacting element; and a fixation element that attaches said bone contacting element to the vertebra, said fixation element being adapted for implantation into an interior bone space of a pedicle of the vertebra;

wherein said prosthesis is configured so that no portion of said prosthesis contacts the posterior arch of said vertebra.

In another form of the present invention, there is provided a method for replacing at least a portion of the bone of a facet located on a mammalian vertebra, comprising:

an articulating element that articulates with another facet;

a bone contacting element that contacts a surface of the vertebra or another element contacting a surface of the vertebra, said articulating element being connected to said bone contacting element; and a fixation element that attaches said bone contacting element to the vertebra, said fixation element being adapted for implantation into an interior bone space of a pedicle of the vertebra;

wherein said prosthesis is configured so that no portion of said prosthesis contacts the posterior arch of said vertebra;

positioning said bone contacting surface against a surface of the vertebra or another element contacting a surface of the vertebra; and attaching said bone contacting surface to the vertebra using said fixation element.

Because the present invention allows for the individual replacements of facets, only comprised facets need be replaced. For example, if only one facet is affected by disease or trauma, it can be resected and replaced with a facet prosthesis that articulates with an opposing natural facet.

The present invention has numerous advantages over the prior art. One advantage is that the quality of attachment of the prosthesis is improved. The present invention provides a precise press fit into bones, as opposed to relying on prosthetic surfaces mating with highly complex and variable external surfaces of the vertebra, such as the posterior arch or facet. Another advantage is that the optional porous coating is placed into interior bone spaces where porous coatings have proven to achieve bone ingrowth for excellent long term fixation strength. This ability to achieve bone ingrowth is uncertain for the prior art devices that engage the external bone surfaces of the vertebra. Yet another advantage lies in the removal of the facet bone structure; where the facet bone is involved in the disease pathology or the trauma that compromised the articular or cartilaginous surface of the facet, resection provides a means for ensuring that all pain associated with the disease or trauma is removed.

The above, and other objects, features and advantages of the present invention, will become apparent from the following description which is to be read in conjunction with the accompanying drawings.

DETAILED DESCRIPTION OF THE PREFERRED EMBODIMENTS

Figure 1:
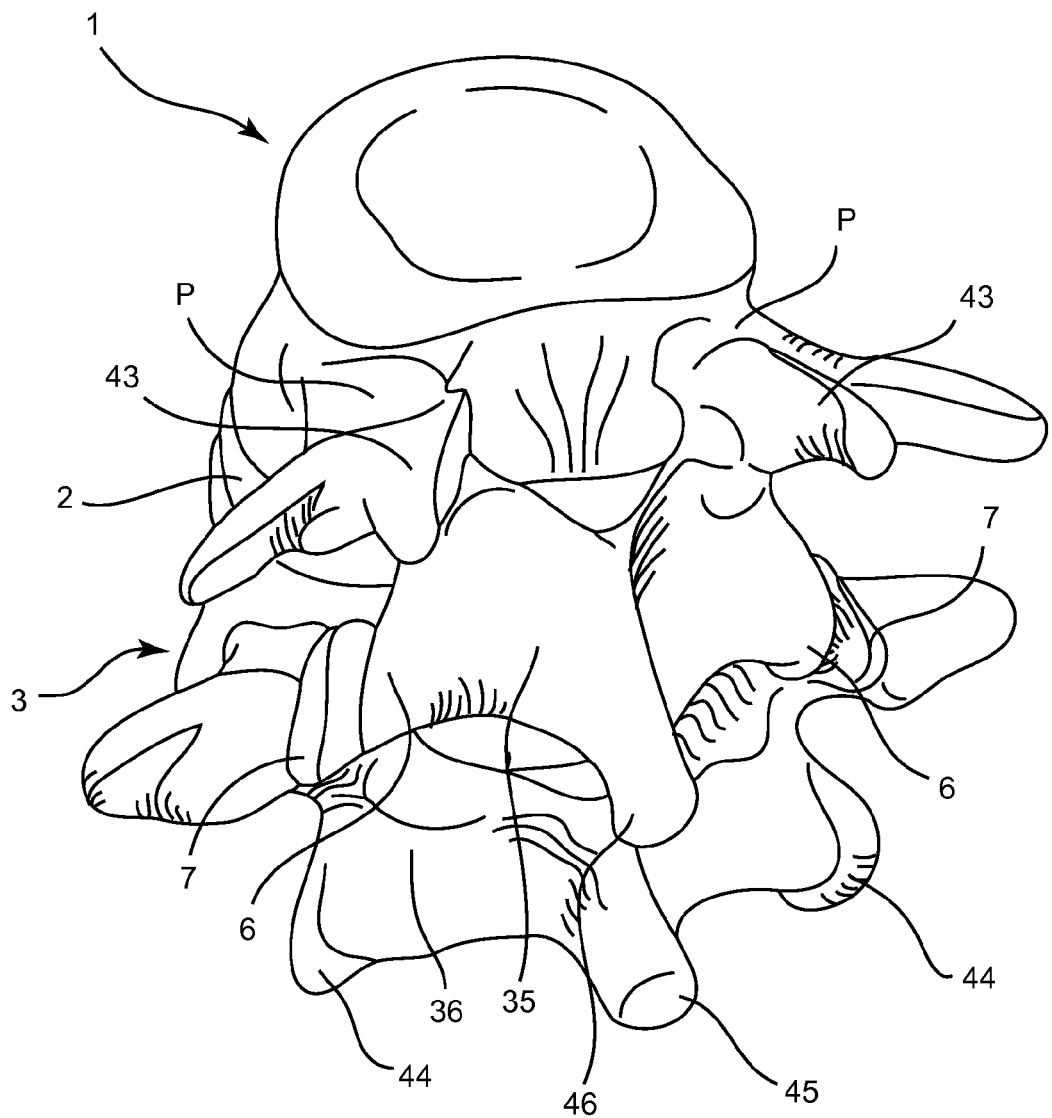
FIG. 1 is a perspective view of a portion of the spine.
Figure 1A:
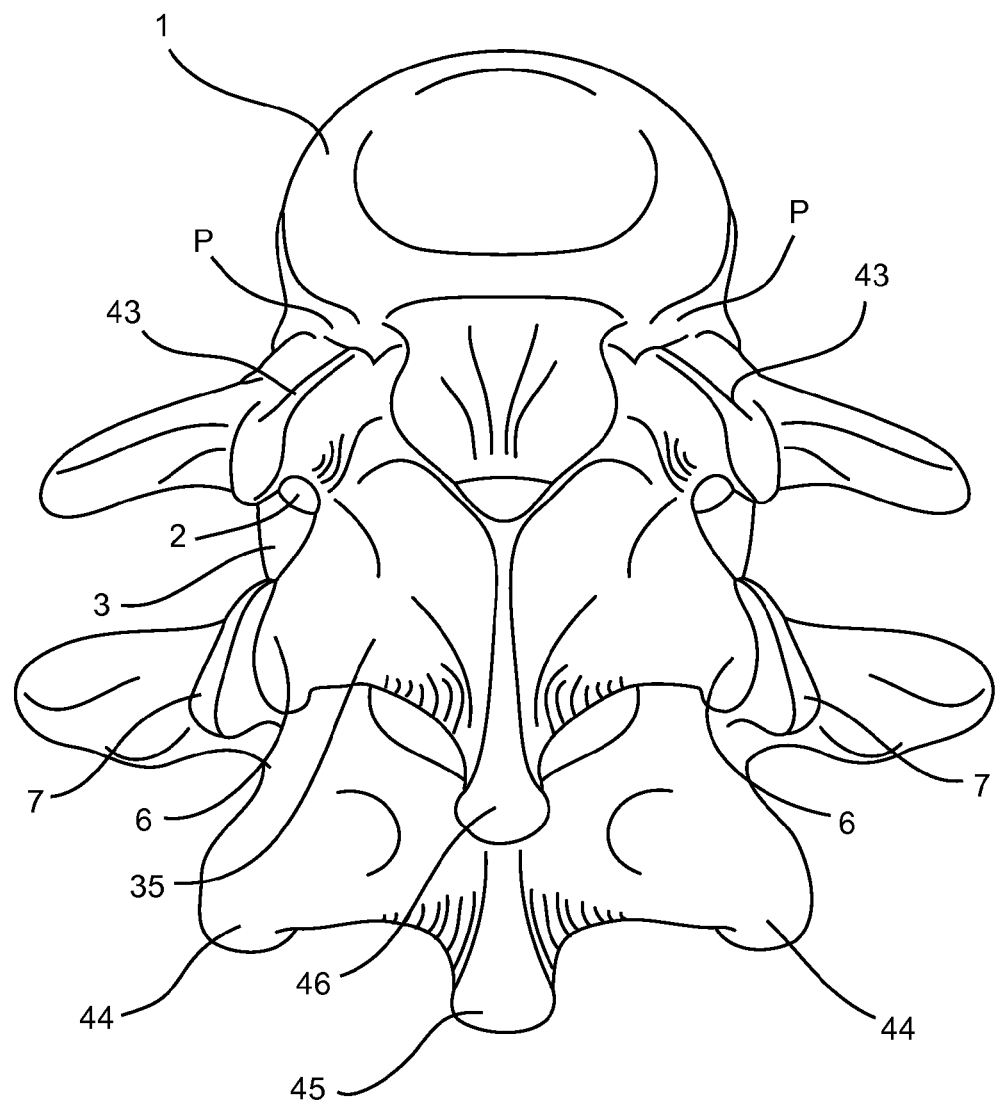
FIG. 1A is a dorsal view of the portion of the spine shown in FIG. 1.

Referring now to FIGS. 1 and 1A, there is shown a superior vertebra 1 and an inferior vertebra 3, with an intervertebral disc 2 located in between. Vertebra 1 has superior facets 43, inferior facets 6, posterior arch (or lamina) 35 and spinous process 46. Vertebra 3 has superior facets 7, inferior facets 44, posterior arch (or lamina) 36 and spinous process 45.

Figure 2:
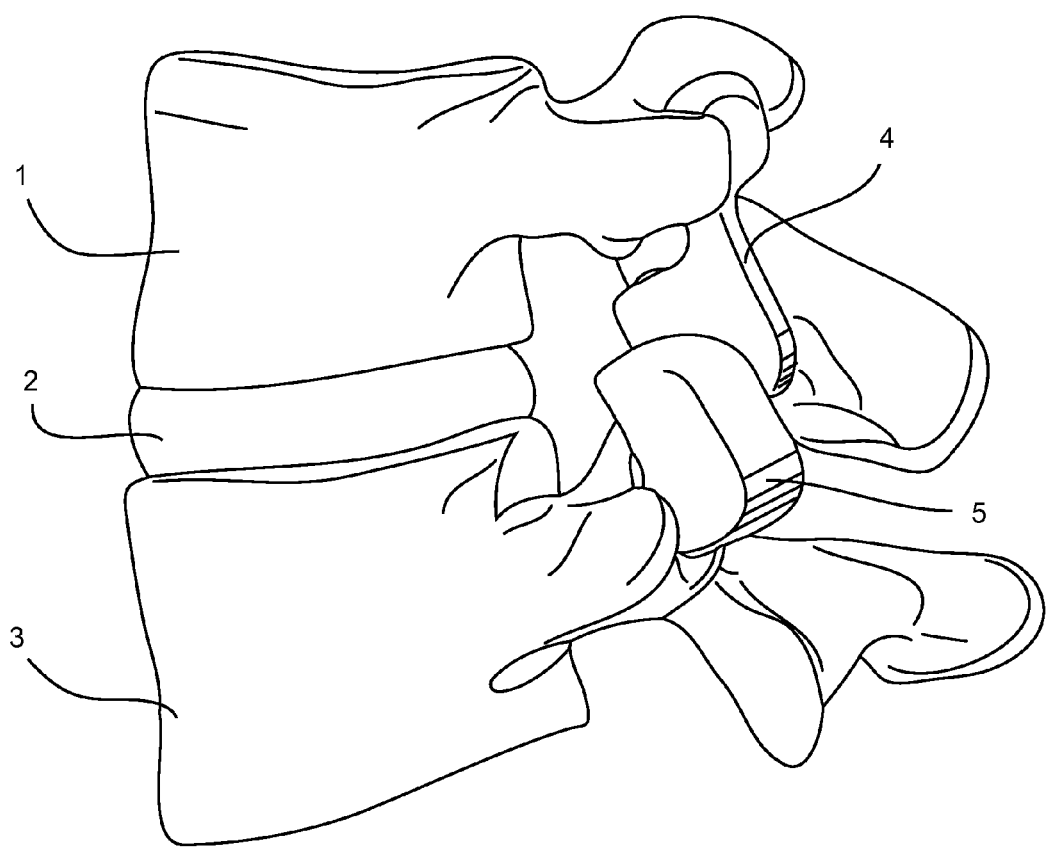
FIG. 2 is a lateral view of a facet joint reconstructed in accordance with the present invention.

Referring now to FIG. 2, the left inferior facet 6 of vertebra 1 shown in FIG. 1 and FIG. 1A has been resected and inferior facet prosthesis 4 has been attached to vertebra 1. Similarly the left superior facet 7 of vertebra 3 has been resected and a superior facet prosthesis 5 has been attached to vertebra 3.

Figure 3:
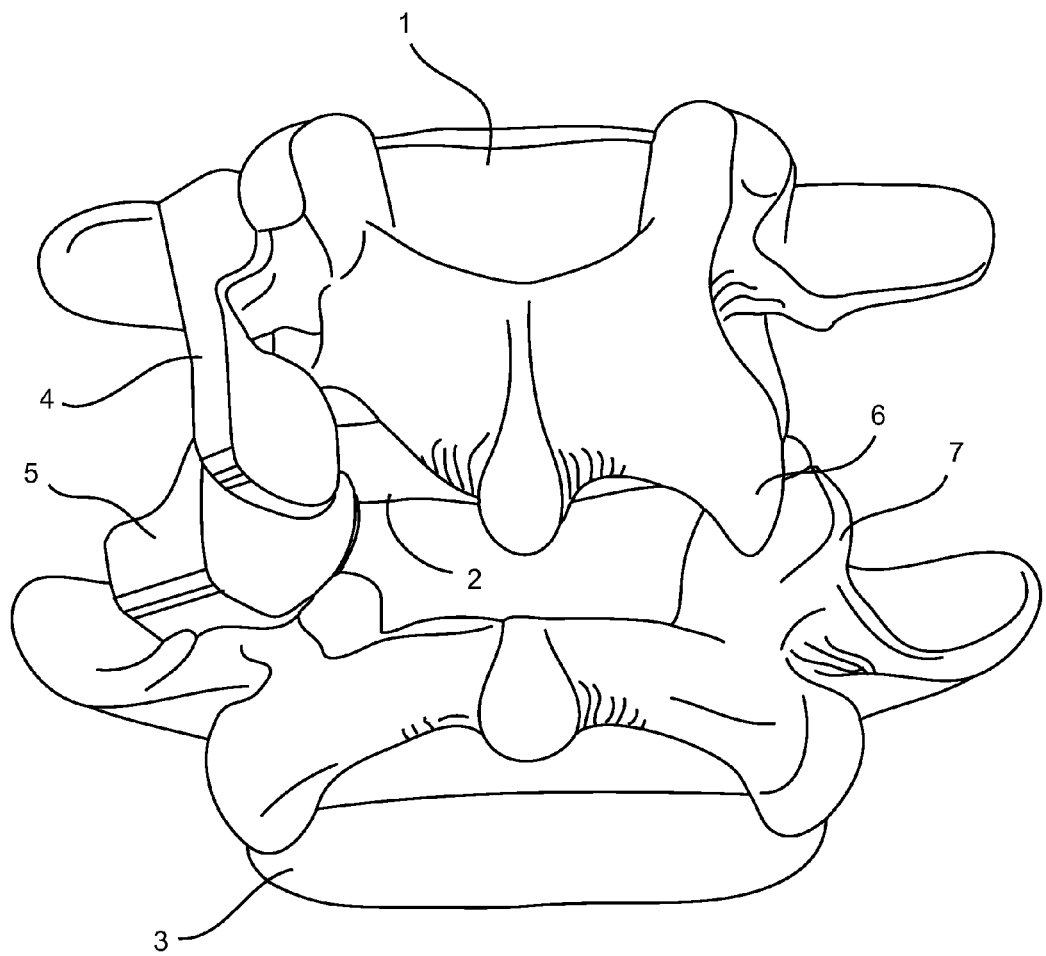
FIG. 3 is a dorsal view of the facet joint shown in FIG. 2.

FIG. 3 illustrates a dorsal view of the elements shown in FIG. 2. It can be appreciated that inferior facet prosthesis 4 replicates the natural anatomy when compared to the contralateral inferior facet 6 of vertebra 1. Similarly, it can be appreciated that superior facet prosthesis 5 replicates the natural anatomy when compared to the contralateral superior facet 7 of vertebra 3. Neither inferior facet prosthesis 4 nor superior facet prosthesis 5 rests on the lamina.

Figure 4:
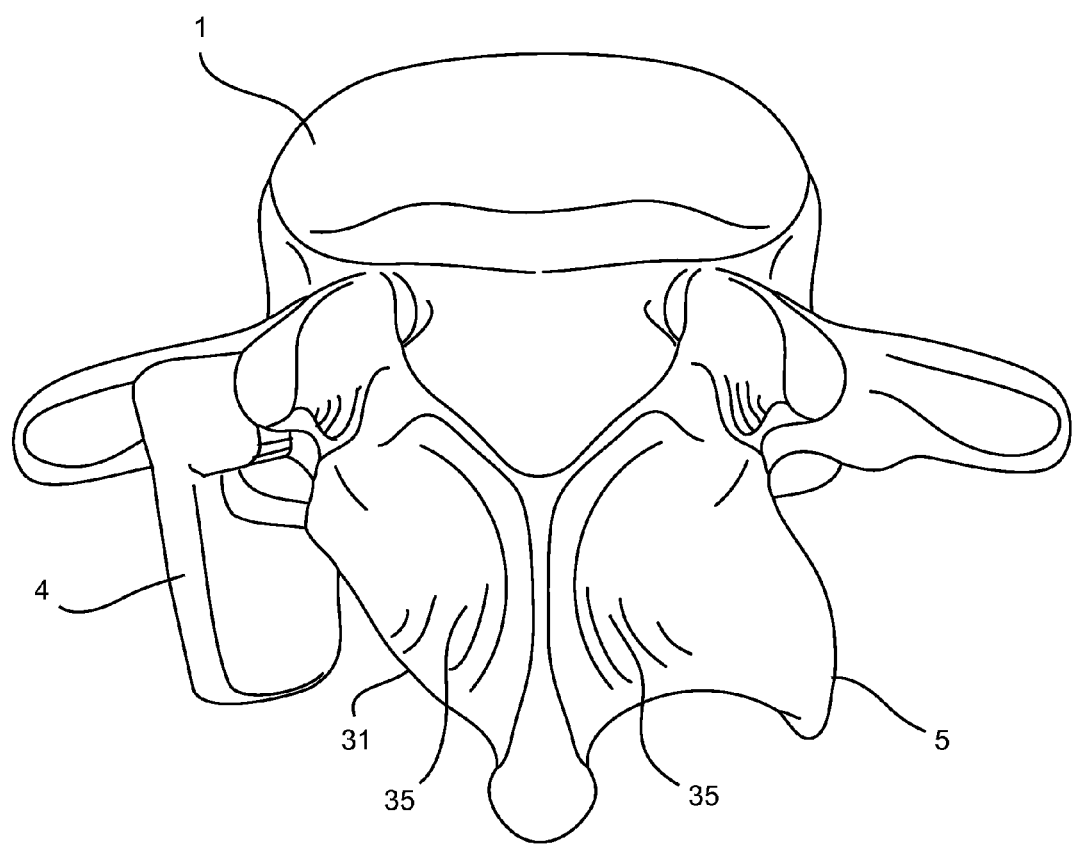
FIG. 4 is a perspective view of the implanted left inferior facet prosthesis shown in FIGS. 2 and 3.

Turning now to FIG. 4, a perspective view of vertebra 1 with implanted inferior facet prosthesis 4 is provided. A bone resection on the left side of the vertebra 1, shown as resection 31, has removed the natural inferior facet 6 at the bony junction between the inferior facet 6 and the posterior arch (or lamina) 35. In this manner, any bone pain associated with a disease, such as osteoarthritis, or trauma of the left inferior facet 6 will be eliminated as the involved bony tissue has been osteotomized.

Figure 5:
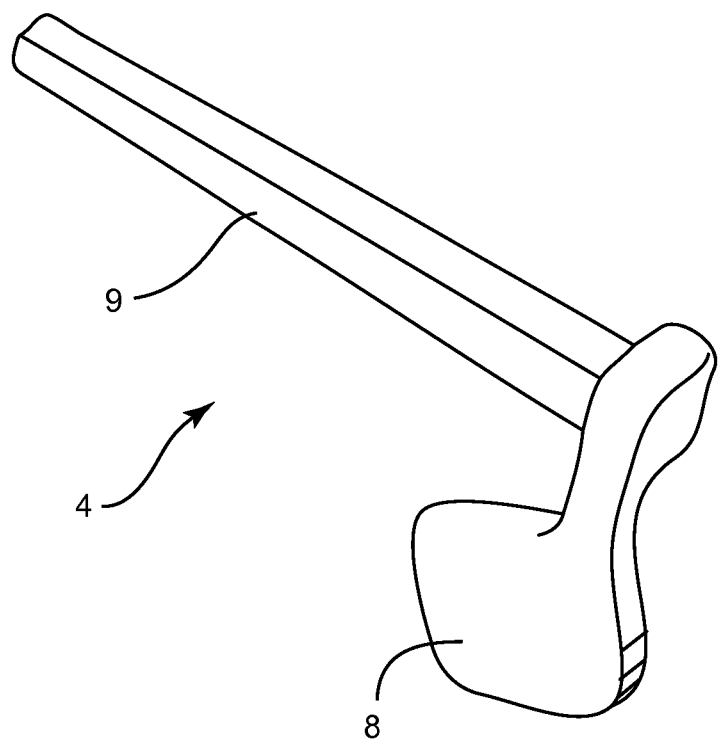
FIG. 5 is a perspective view of the left inferior facet prosthesis shown in FIGS. 2 and 3.

FIG. 5 illustrates a perspective view of inferior facet prosthesis 4. Surface 8 replicates the natural articular surface of the replaced inferior facet 6. Post 9 provides a means to affix inferior facet prosthesis 4 to vertebra 1. Post 9 is implanted into the interior bone space of the left pedicle on vertebra 1 and may or may not extend into the vertebral body of vertebra 1 to provide additional stability.

Figure 6:
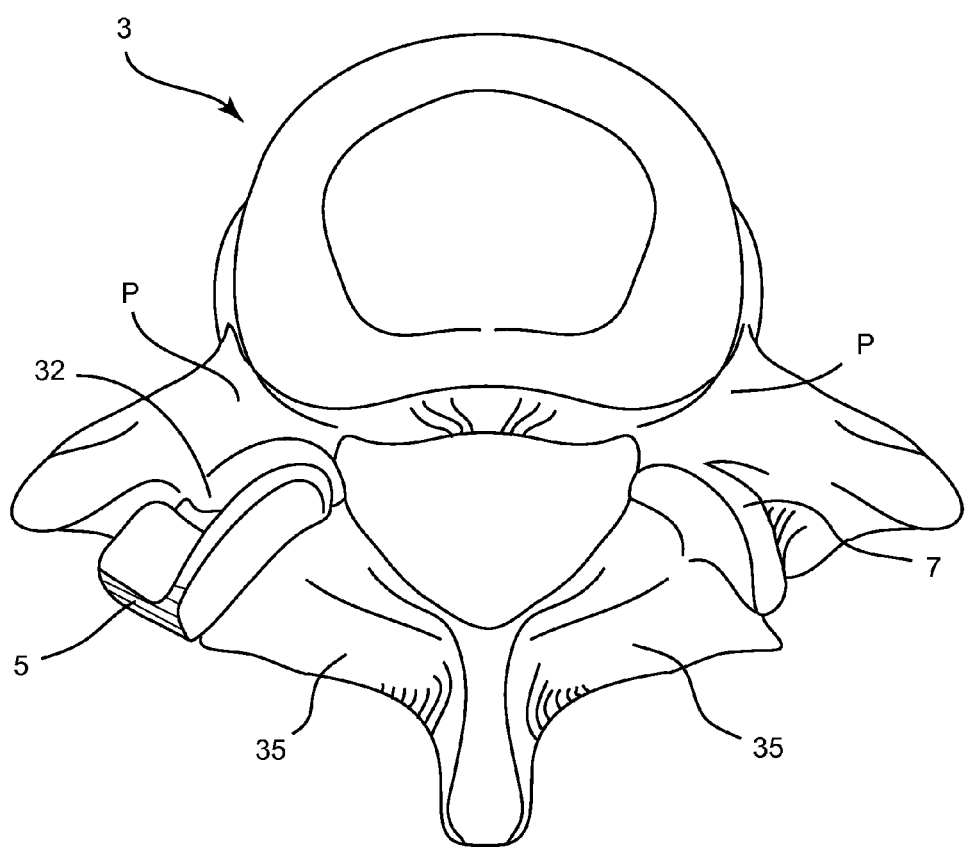
FIG. 6 is a cranial view of the implanted left superior facet prosthesis shown in FIGS. 2 and 3.

FIG. 6 illustrates a cranial view of vertebra 3 with implanted superior facet prosthesis 5. Resection surface 32 represents the bony junction between the natural superior facet 7 and the posterior arch 35.

Figure 7:
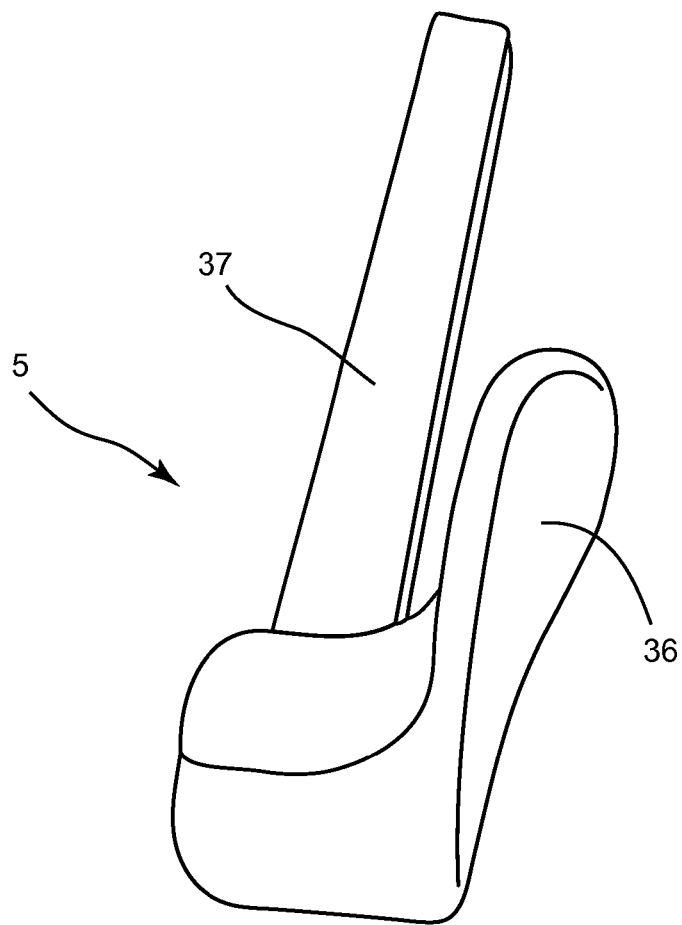
FIG. 7 is a perspective view of the left superior facet prosthesis shown in FIGS. 2 and 3.

FIG. 7 illustrates a perspective view of superior facet prosthesis 5. Surface 36 replicates the natural articular surface of the replaced superior facet 7. Post 37 provides a means for affixing superior facet prosthesis 5 to vertebra 3. Post 37 is implanted into the interior bone space of the left pedicle P (FIG. 6) on vertebra 3 and may or may not extend into the vertebral body of vertebra 3 to provide additional stability.

When the total facet joint is replaced, as shown in FIGS. 2 and 3, then surface 8 (FIG. 5) articulates with surface 36 (FIG. 7) to recreate the natural biomechanics of the spine motion segment made up of vertebra 1, vertebra 3, and intervertebral disc 2. Neither inferior facet prosthesis 4 nor superior facet prosthesis 5 rests on the lamina.

Figure 8:
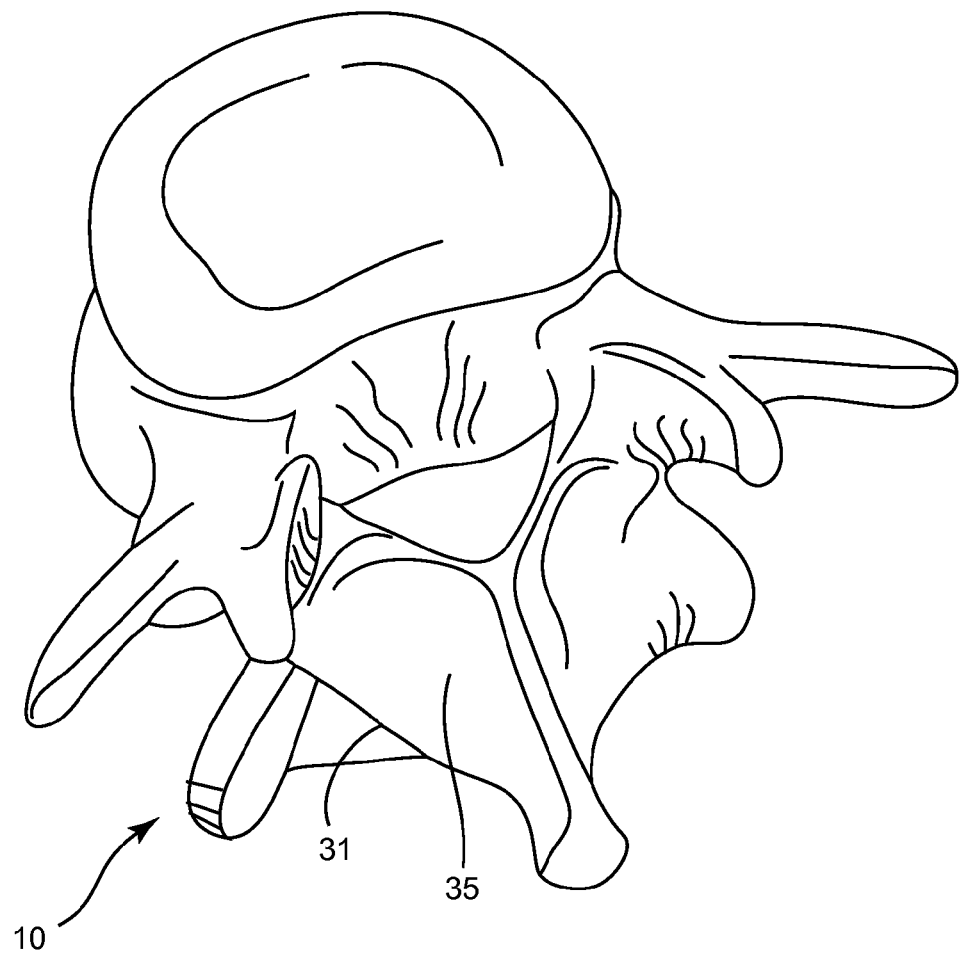
FIG. 8 is a perspective view of an alternate implanted left inferior facet prosthesis.

FIG. 8 illustrates an alternative inferior facet prosthesis 10 which is implanted into the interior bone space of posterior arch (or lamina) 35. The interior bone space is accessed from the resection 31.

Figure 9:
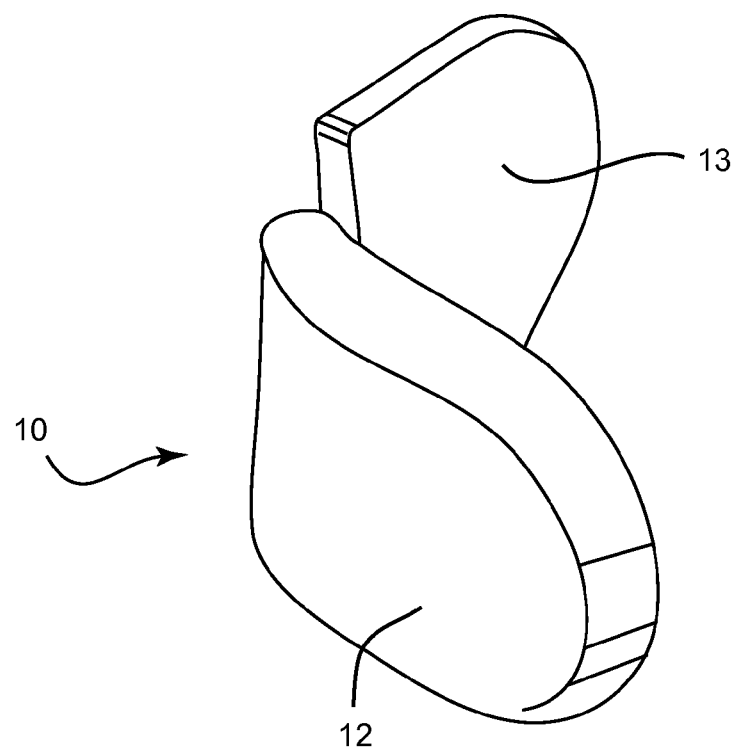
FIG. 9 is a perspective view of an alternate left inferior facet prosthesis.

FIG. 9 shows details of alternative inferior facet prosthesis 10, including the fin 13 that extends into the interior bone space of posterior arch 35. Surface 12 replicates the natural articular surface of the replaced facet.

The surfaces of post 9 (FIG. 5), post 37 (FIG. 7) and fin 13 (FIG. 9) may or may not include porous coatings to facilitate bone ingrowth to enhance the long term fixation of the implant. Furthermore, such porous coatings may or may not include osteoinductive or osteoconductive substances to further enhance the bone remodeling into the porous coating.

Figure 10:
FIG. 10 is a lateral view of an alternative reconstructed facet joint.

Referring now to FIG. 10, there is shown a lateral view of a superior vertebra 14 and an inferior vertebra 16, with an intervertebral disc 15 located in between. The left inferior facet of vertebra 14 has been resected and an inferior facet prosthesis 18 has been attached to vertebra 14 by means of a screw fastener 17. Similarly, the left superior facet of vertebra 16 has been resected and a superior facet prosthesis 19 has been attached to vertebra 16 by means of a screw fastener 17.

Figure 11:
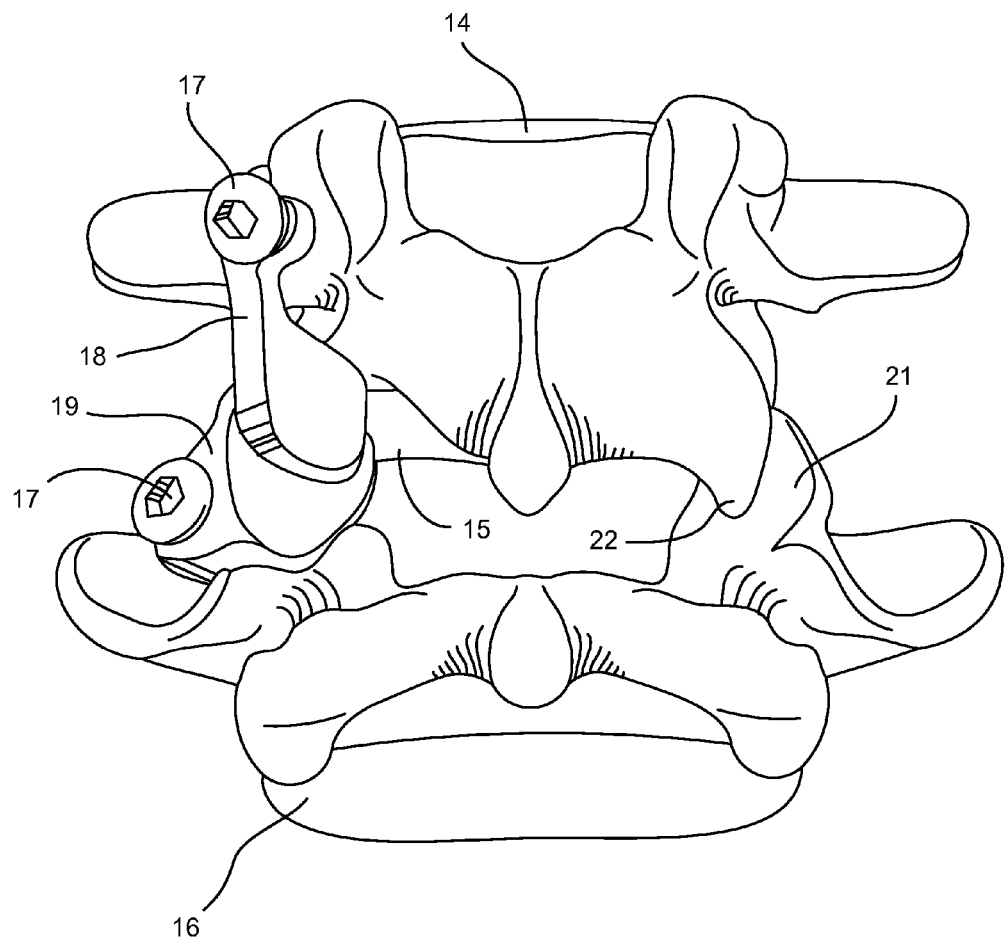
FIG. 11 is a dorsal view of an alternative reconstructed facet joint.

FIG. 11 illustrates a dorsal view of the elements of FIG. 10. It can be appreciated that inferior facet prosthesis 18 replicates the natural anatomy when compared to the contralateral inferior facet 22 of vertebra 14. Similarly, it can be appreciated that superior facet prosthesis 19 replicates the natural anatomy when compared to the contralateral superior facet 21 of vertebra 16. Neither inferior facet prosthesis 18 nor superior facet prosthesis 19 rests on the lamina.

Figure 12:
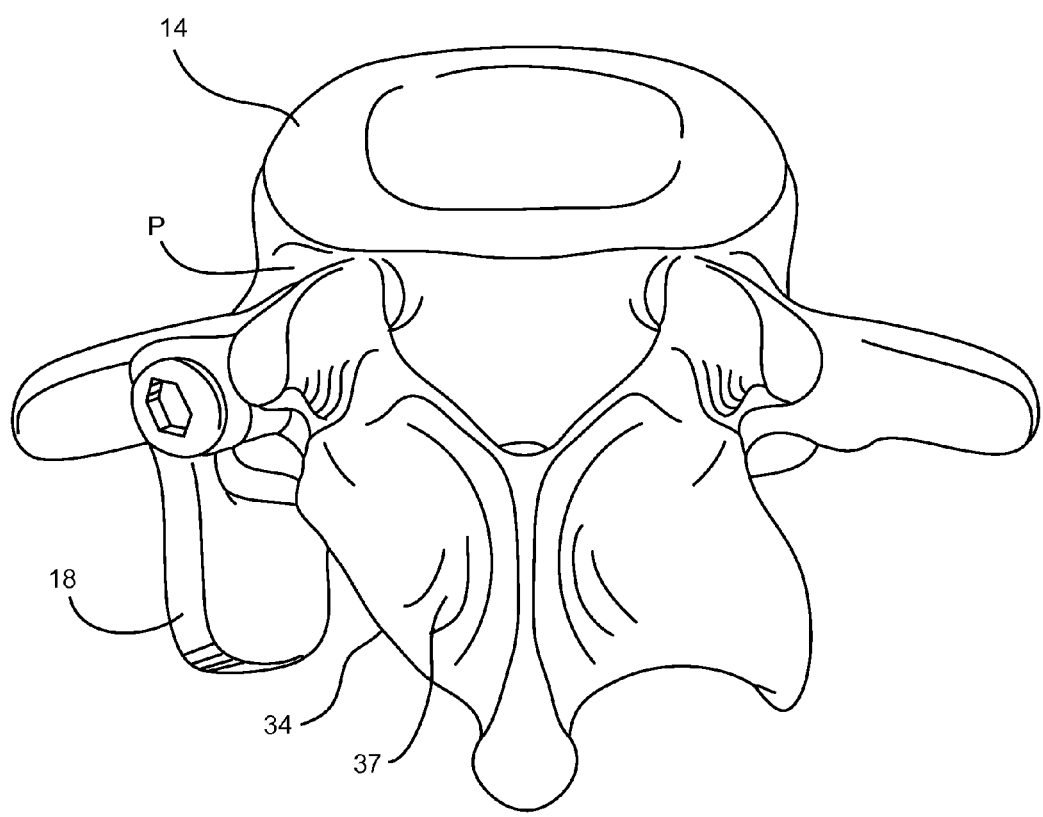
FIG. 12 is a perspective view of the implanted left inferior facet prosthesis shown in FIGS. 10 and 11.

Turning now to FIG. 12, there is provided a perspective view of vertebra 14 with implanted inferior facet prosthesis 18. Resection 34 has removed the natural inferior facet at the bony junction between the inferior facet and the posterior arch 37. In this manner, any bone pain associated with a disease, such as osteoarthritis, or trauma of the natural inferior facet 22 will be eliminated inasmuch as the involved bony tissue has been osteotomized.

Figure 13:
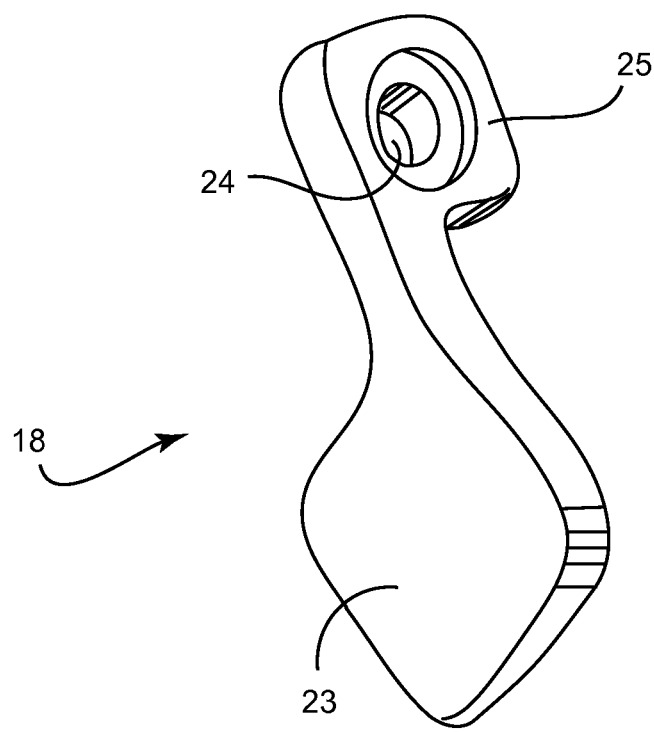
FIG. 13 is a perspective view of the alternative left inferior facet prosthesis shown in FIGS. 10 and 11.

FIG. 13 illustrates a perspective view of inferior facet prosthesis 18. Surface 23 replicates the natural articular surface of the replaced facet. Flange 25 contacts the pedicle P (FIG. 12) and hole 24 receives a screw fastener 17 to attach inferior facet prosthesis 18 to vertebra 14.

Figure 14:
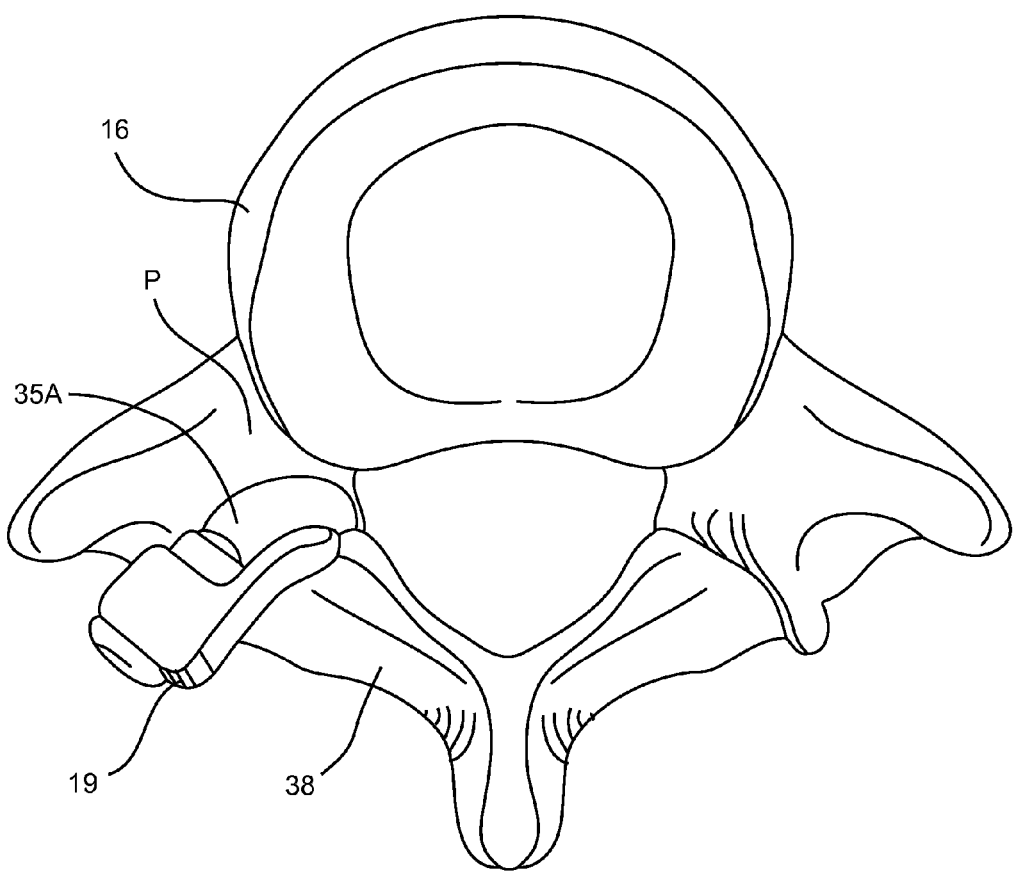
FIG. 14 is a cranial view of the alternative implanted left superior facet prosthesis shown in FIGS. 10 and 11.

FIG. 14 illustrates a cranial view of vertebra 16 with implanted superior facet prosthesis 19. Resection surface 35A represents the bony junction between the natural superior facet 21 (FIG. 11) and the posterior arch 38.

Figure 15:
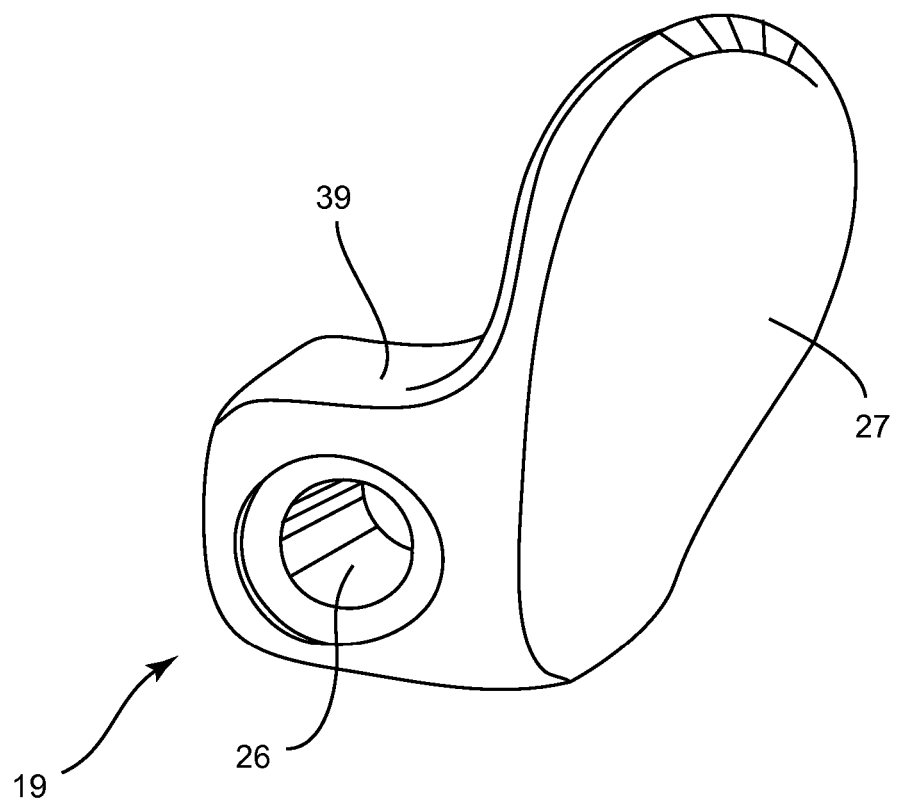
FIG. 15 is a perspective view of the alternative left superior facet prosthesis shown in FIGS. 10 and 11.

FIG. 15 illustrates a perspective view of superior facet prosthesis 19. Surface 27 replicates the natural articular surface of the replaced facet. Flange 39 contacts the pedicle P (FIG. 14) and hole 26 receives a screw fastener 17 to attach superior facet prosthesis 19 to vertebra 16.

Figure 16:
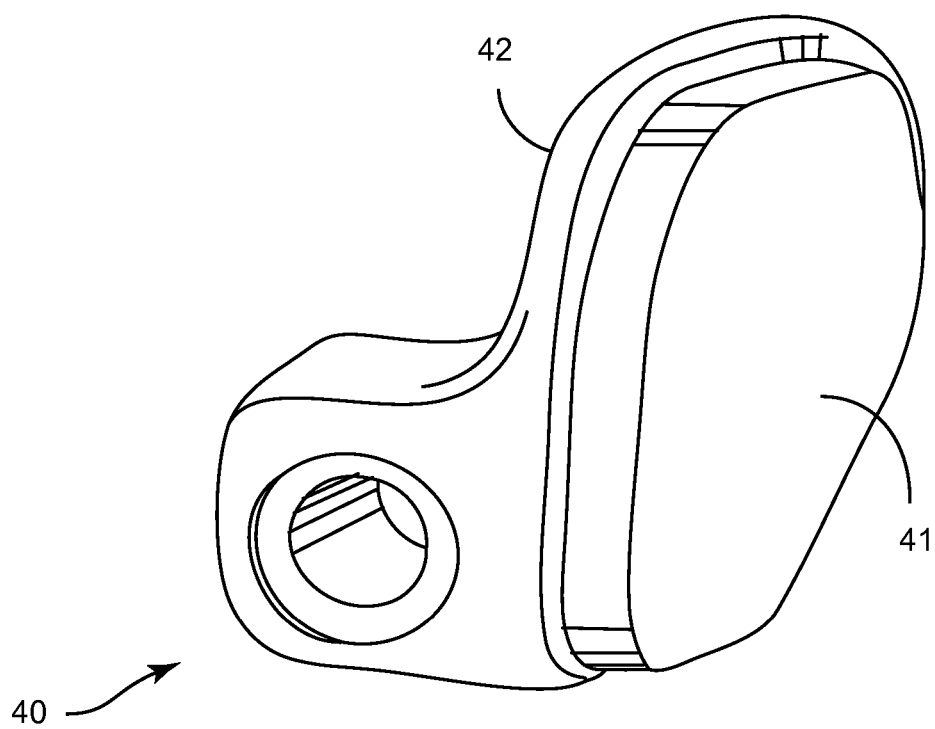
FIG. 16 is a perspective view of an alternate bearing surface for the superior facet prosthesis shown in FIG. 15.

FIG. 16 illustrates an alternative superior facet prosthesis 40 with a bearing surface 41 that mounts to substrate 42. The bearing surface 41 is a biocompatible polymeric material, such as ultra high molecular weight polyethylene. Alternately, the bearing surface can be ceramic, such as zirconia or alumina. The substrate is a biocompatible metal alloy, such as an alloy of titanium, cobalt, or iron.

Figure 17:
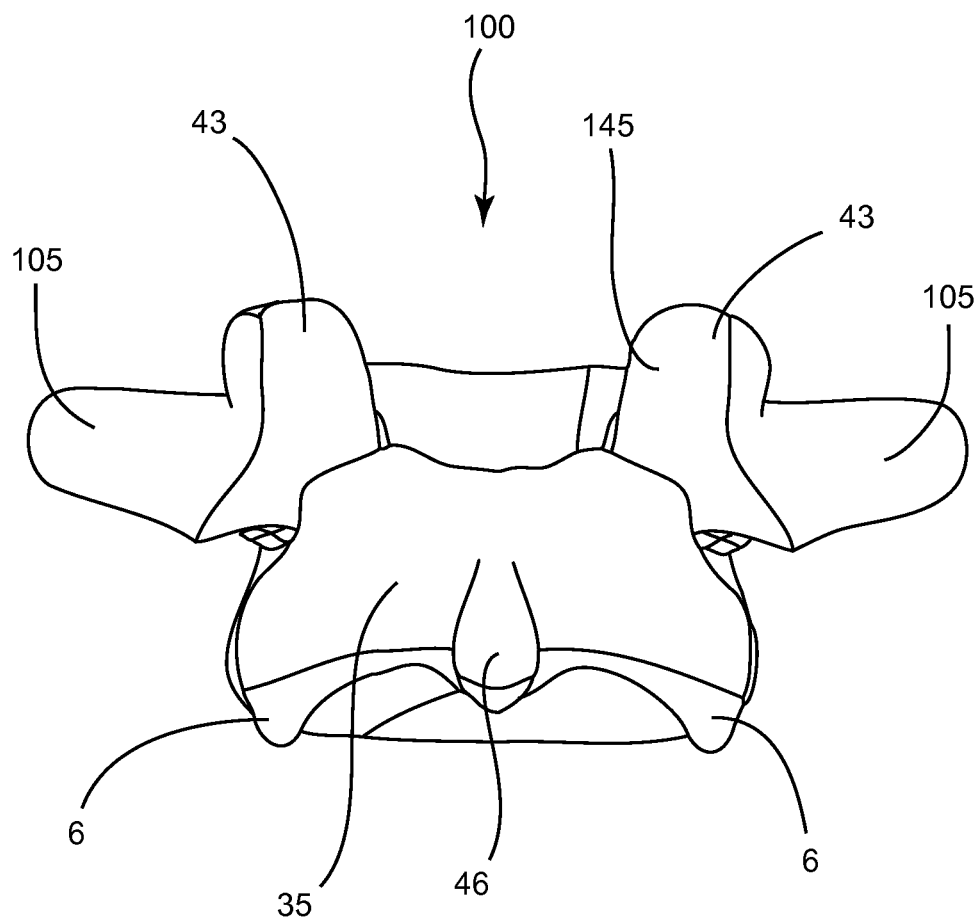
FIG. 17 is a dorsal view of a single intact vertebra.
Figure 18:
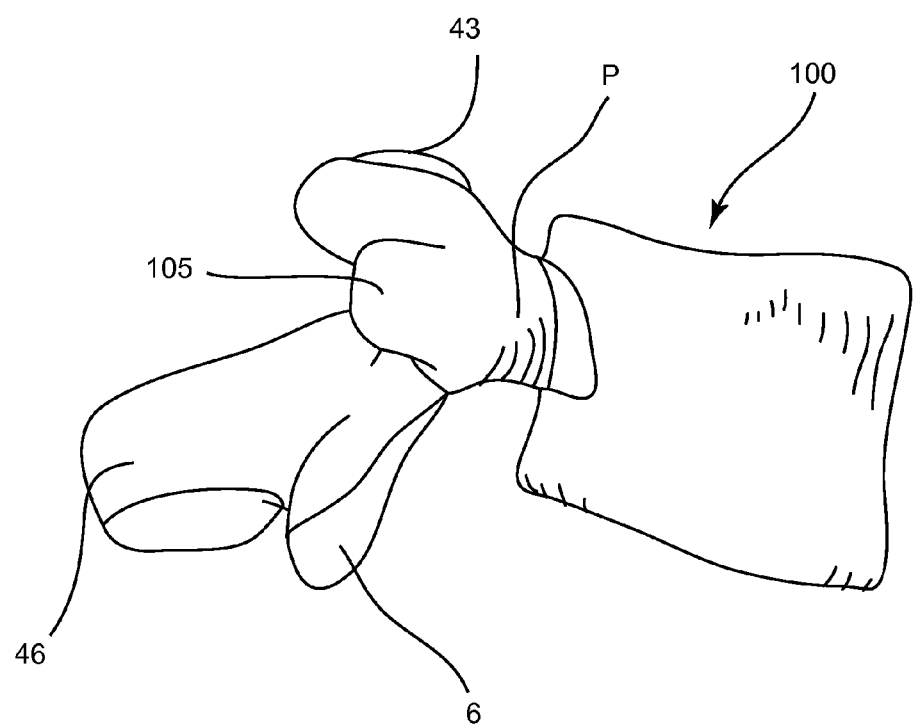
FIG. 18 is a lateral view of the same intact vertebra shown in FIG. 17.

Referring to FIG. 17 and FIG. 18, a single intact vertebra 100 is shown. FIG. 17 is a dorsal view of the vertebra 100. FIG. 18 is a lateral view of the same vertebra 100. Similar to the two vertebra shown in the portion of the spine illustrated in FIGS. 1 through 3, the vertebra 100 has posterior anatomy comprising left and right superior facets 43 on the superior, or top side in this view of the dorsal vertebra 100, left and right inferior facets 6 on the inferior or bottom side of the posterior vertebra 100, left and right transverse processes 105 extending laterally from the posterior portion of vertebra 100, and left and right pedicles P. The posterior portion of vertebra 100 also has a posterior arch (or lamina) 35, and a spinous process 46 that protrudes from the posterior arch 35 posteriorly, out of the page in FIG. 17 and to the left in FIG. 18. In FIG. 17, the bony structure of the superior facets 43 and the inferior facets 6 are intact, as it would be presented in a vertebra without significant tissue degeneration or remodeling resulting from facet joint disease. Although the vertebra 100 is shown in FIG. 17 as a generally structurally healthy and intact vertebra, if the vertebra 100 were a diseased vertebra, the vertebra could exhibit signs of facet joint disease.

Consequently, structural pathology related to facet joint disease would likely be visible. For example, the left superior facet 43 and the right superior facet 43 of the vertebra 100 axe symmetrical in FIG. 17 and FIG. 18. But in the case of a vertebra 100 with only one diseased joint, the facet on the diseased side would likely be showing pathological signs of disease such as tissue degeneration or inflammation resulting in an asymmetrical structural comparison between the two facets. Also, in more extreme cases the facet disease could progress to a state in which the articular process of the facet is eroded or inflamed resulting in anatomic morphology that is unique to the pathology of a particular facet joint of an individual patient. This could present unusual facet morphology that could be different from what is shown in FIGS. 17 and 18. Furthermore, the facet disease could eventually disable the biomechanics of a patient such that the facet joint is essentially non-articulating and immobile. In this case, one superior facet of a first vertebra could essentially be fused to one inferior facet of a second vertebra.

Figure 19:
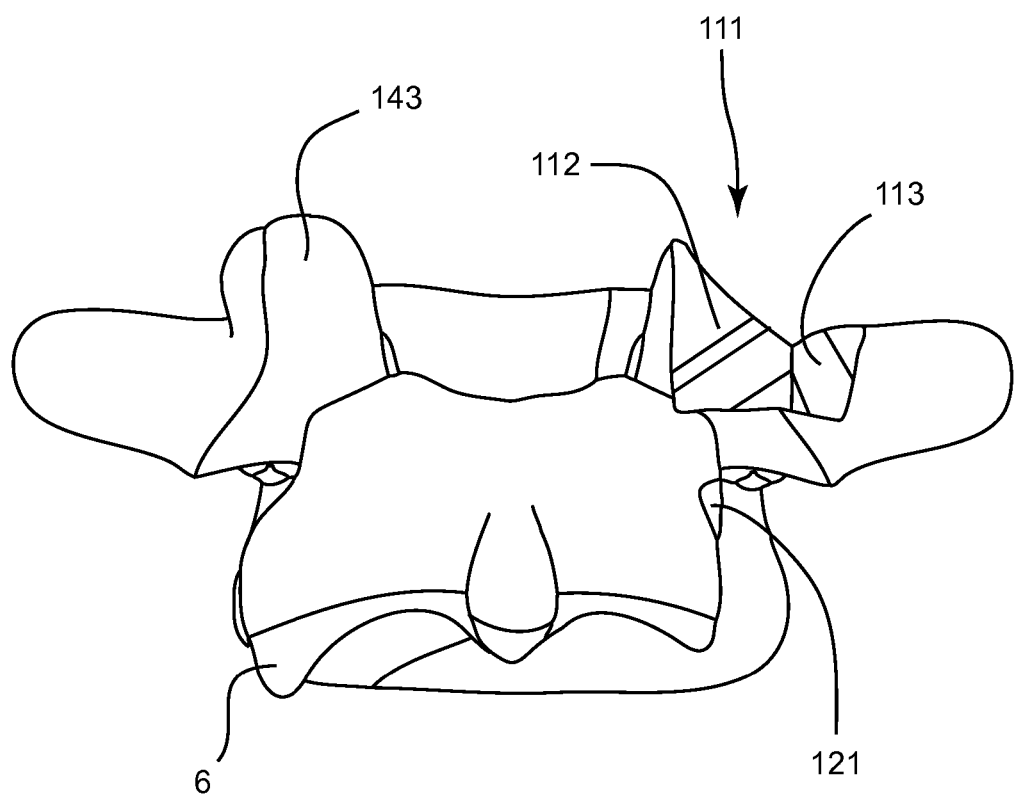
FIG. 19 is a dorsal view of the same vertebra of FIG. 17 and FIG. 18, with a portion of the superior facet resected and a portion of the inferior facet resected.
Figure 20:
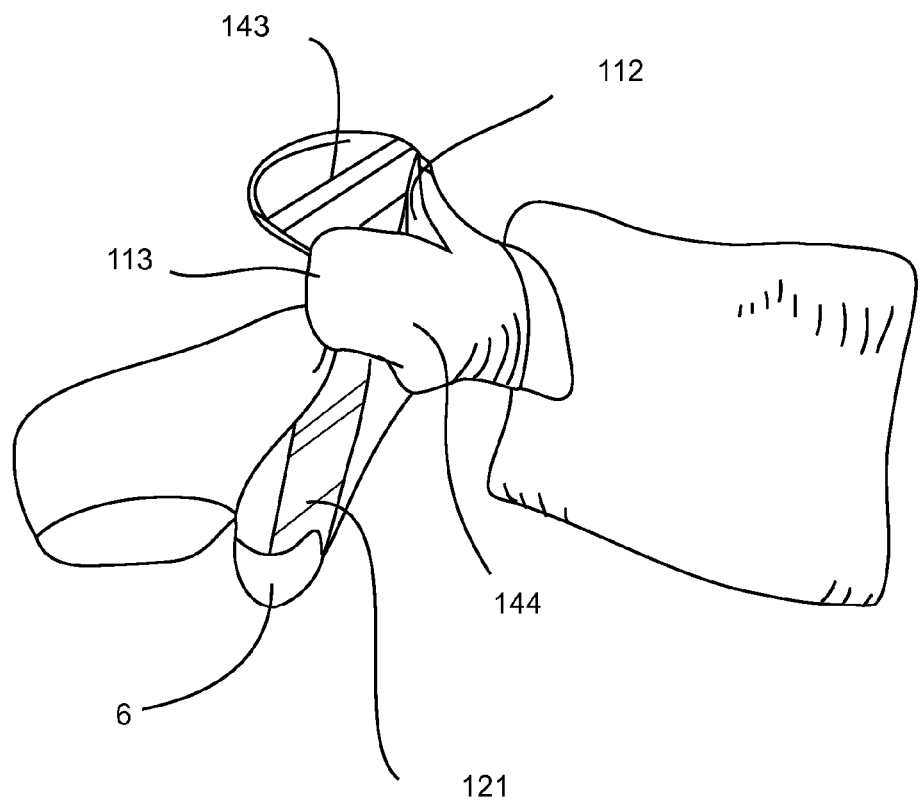
FIG. 20 is a lateral view of the resected vertebra shown in FIG. 19.

Since the structural pathology of the diseased facet is variable, a surgeon may determine that the best bone apposition surface or foundation for securing a facet implant is a resected bone surface. Referring to FIG. 19 and FIG. 20 which are dorsal and lateral views, of the same vertebra shown in FIG. 17 and FIG. 18 after a portion of the right superior facet 43 and a portion of the right inferior facet 6 have been resected. The removal of a portion of the superior facet 43 by resection results in a superior facet resection 111. In the resection shown in FIG. 19 and FIG. 20, the superior resection 111 has two resulting faces, a first resection surface 112 and a second resection surface 113. Likewise, the interior facet resection results in an inferior facet resection surface 121.

Figure 22:
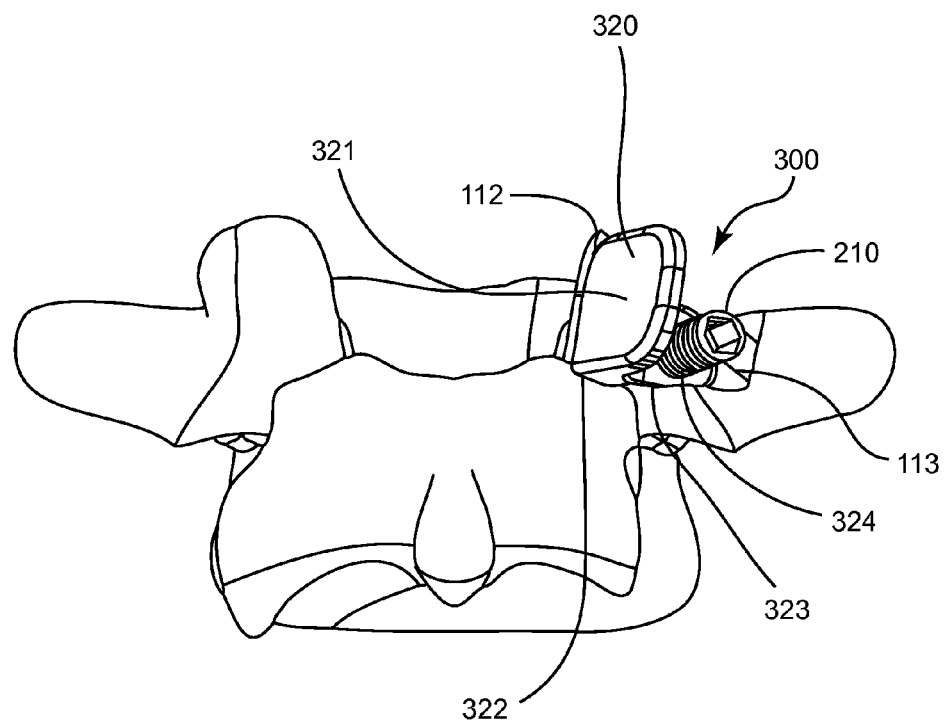
FIG. 22 is a dorsal view showing the resected vertebra, the fixation element, and a superior facet prosthesis.

Tissue removal tools (not shown) such as a bone burr, rasp, reamer, mill, saw, rounger, osteotomy or similar tools designed to cut and remove bone tissue can be used to create these resection surfaces. The surgeon uses anatomic landmarks such as the pedicle P or transverse process 105 to align the tissue removal tools in such a way as to remove the portion of the facet necessary to provide a superior resection 111 that serves as a bone apposition surface or foundation to eventually support the superior facet prosthesis 300, as shown in FIG. 22. The left superior facet 43 is shown intact in both FIG. 19) and FIG. 20, but a portion of the right superior facet 43 is resected resulting in the first resection surface 112 and the adjacent second resection surface 113 (FIG. 19). The shape of superior resection 111 will vary in accordance with the structure of the tissue removal tool. In this embodiment shown in FIG. 19 and FIG. 20, the first resection surface 112 and the second resection surface 113 are on approximately perpendicular planes. However, the geometry of the resections surfaces are a function of the patient anatomy, the pathology of the diseased tissue, the technique of the surgeon, and other factors such as the type of tissue removal tools used to prepare the resection. In general, the first resection surface 112 will be formed in such a way that it will serve as a foundation to support the superior facet prosthesis 300 (FIG. 22). The second resection surface 113 or other additional resection surfaces may or may not be present.

FIG. 19 and FIG. 20 also show that a portion of the inferior facet 6 is resected by tissue removal instruments resulting in an inferior resection surface 121. Such resection is preferably effected so that resection is confined to the tissue of inferior facet 6 and does not extend into the tissue of posterior arch (or lamina) 35. In FIGS. 19 and 20, the left inferior facet 6 is intact, while a portion of the right inferior facet 6 is resected resulting in an inferior resection surface 121 on the right side. The bone surrounding the inferior resection surface 121 is formed by tissue removal tools in a shape designed to cradle and support the inferior facet prosthesis 400 (FIG. 23) on the medial side such that when the inferior facet prosthesis 400 is loaded on the lateral side it compresses against and is supported by the inferior resection surface 121.

Alternatively, inferior facet 6 can be resected, and inferior facet prosthesis 400 sized and shaped, so that inferior facet prosthesis 400 does not engage inferior resection surface 121.

Figure 21:
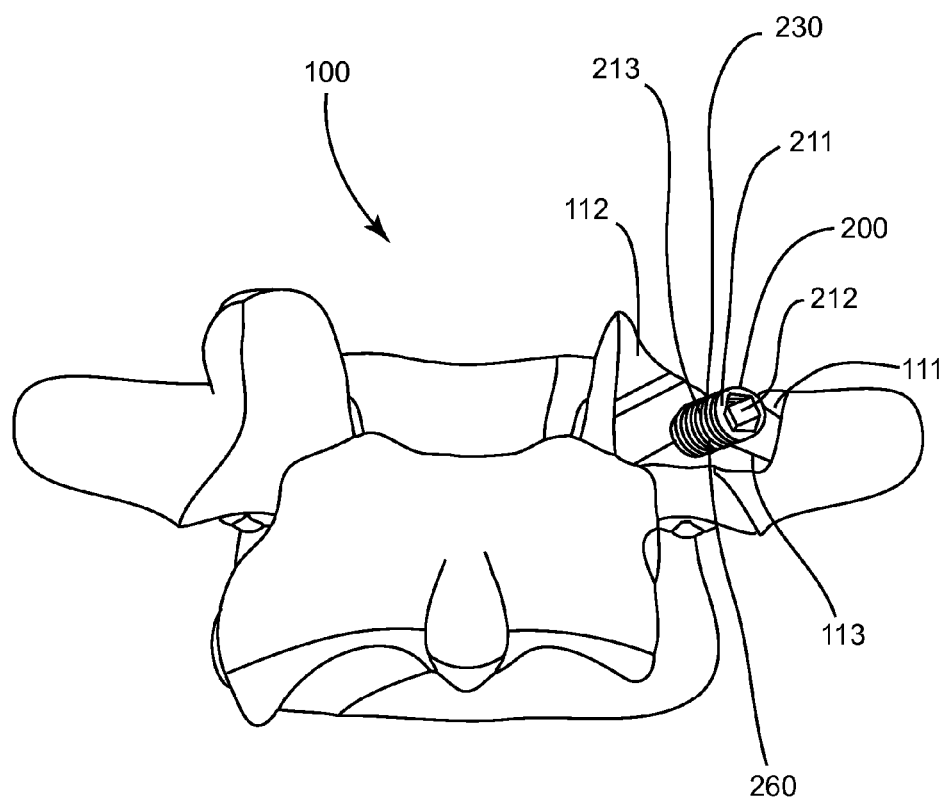
FIG. 21 is a dorsal view of the same resected vertebra shown in FIG. 18 and FIG. 19 with a fixation element placed through the first superior resection surface and into the pedicle bone.
Figure 26:
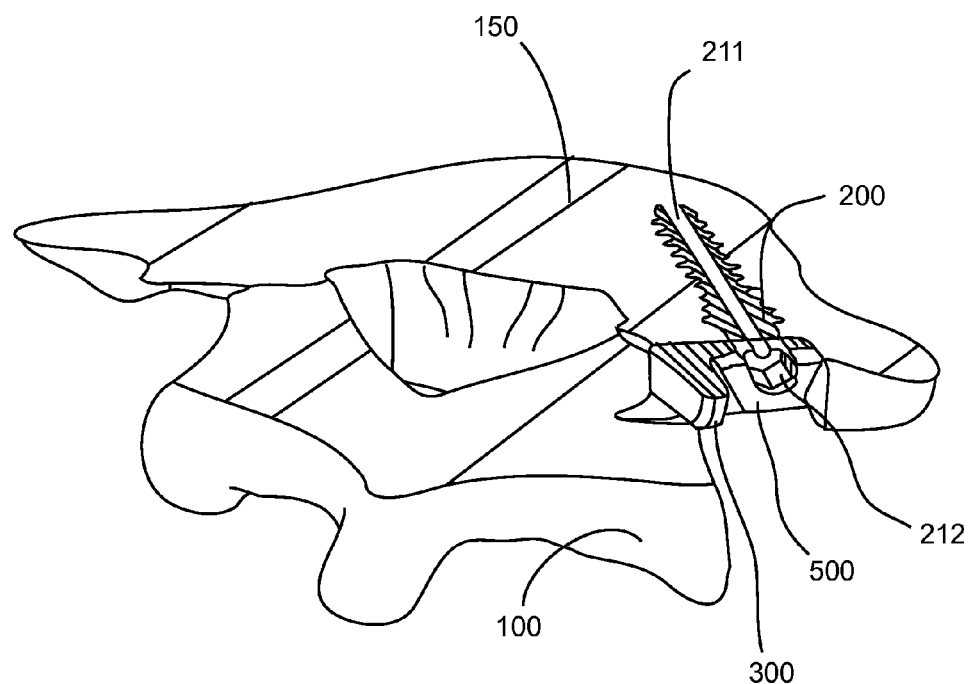
FIG. 26 is a cross-sectional view of the same vertebra and implant of FIG. 25 showing the result of a cross-sectional view cut aligned with the axis of the fixation element.
Figure 27:
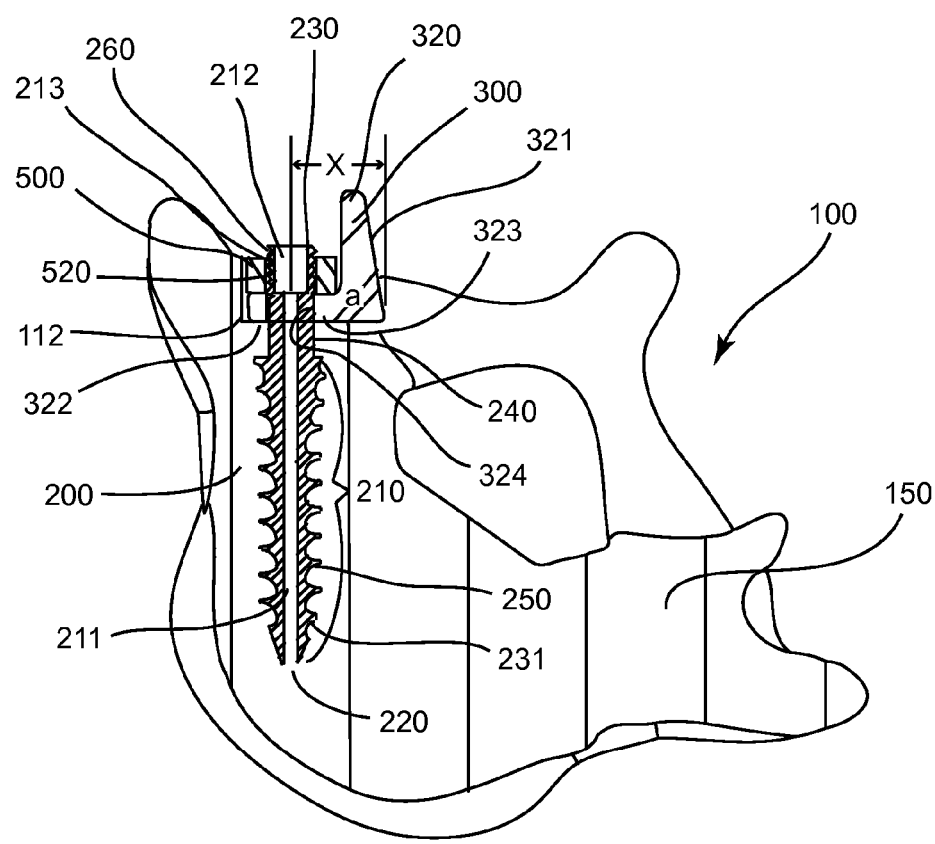
FIG. 27 is a view of the same cross-section described in FIG. 26, aligned to face the viewer.

FIG. 21 shows the vertebra 100 with a fixation element 200 portion of the facet implant placed through the superior resection 111 and into the bone of the pedicle P. The fixation element 200 is aligned and placed into the pedicle, similar to how other pedicle screws for posterior stabilization involved with vertebrae fusion are placed in the pedicle. In one method, a long guide wire (not shown), with a diameter sized to fit freely into a cannulation 211 (as shown in FIG. 26 and FIG. 27) in the fixation element 200, is placed through the first resection surface 112 and into the pedicle bone P. The alignment of the long guide wire can be confirmed by x-ray. The fixation element 200 is then guided over the guide wire and driven into the vertebra by a driver (not shown) engaged with the drive feature 212 (FIG. 21) on the proximal post 230 of the fixation element 200. The fixation element 200 is driven into the vertebra until a connection feature 213 (e.g., a screw thread) is just above the first resection surface 112. This connection feature 213 is eventually used to secure the superior facet prosthesis 300 to the vertebra 100.

In a second method for guiding the fixation element 200 in the pedicle P, a long guide wire (not shown), with a diameter sized to fit freely into a cannulation in a bone preparation instrument (not shown) such as a lap, drill, broach or reamer, is placed through the first resection surface 112 and into the pedicle bone P. The alignment of the long guide wire can be confirmed by x-ray. The bone preparation instrument is then guided over the guide wire and driven into the pedicle P bone to prepare a cavity for the fixation element 200. The guide wire and bone preparation instrument are then removed and the fixation element 200 is guided into the prepared cavity in the pedicle bone P by a driver (not shown) engaged with the drive feature 212 on the proximal post 230 of the fixation element 200. Like in the first method, the fixation element 200 is driven into the vertebra until a connection feature 213 (e.g., a screw thread) is just above the first resection surface 112. This connection feature 213 is eventually used to secure the superior facet prosthesis 300 to the vertebra 100.

In yet a third method of placing the fixation element 200 in the pedicle, the surgeon aligns the fixation element 200 with anatomic landmarks and simply drives the fixation element 200 through the first resected surface 112 and into the pedicle bone P. As with the first and second methods, the fixation element 200 is driven into the vertebra until a connection feature 213 (e.g., a screw thread) is just above the first superior resection surface 112.

In FIG. 22, a superior facet prosthesis 300 is shown placed around the fixation element 200. The superior facet prosthesis 300 has a facet articulating component 320 that articulates with the inferior facet articulating surface of the vertebra above it. Facet articulating component 320 is preferably formed in the general shape of a blade or wing ear. The superior facet prosthesis 300 also has a bone apposition surface 322 that has been placed on the first resection surface 112 and an opening 324 in a flange 323 that surrounds the fixation element 200. The superior facet articulating component 320 has an articulating surface 321 generally adjacent to the flange 323 that is orientated in a direction that faces approximately the same direction that the original anatomic superior articulating surface 145 faced prior to resection. This orientation of the articulating surface 321 allows the superior facet prosthesis 300 to function as either a hemiplasty implant and articulate against a natural anatomic inferior facet 6 or act as a unilateral prosthesis and articulate against an inferior facet prosthesis 400 on the vertebra superior (cephalad) to it. No portion of superior facet prosthesis 300 rests on the lamina.

Figure 23:
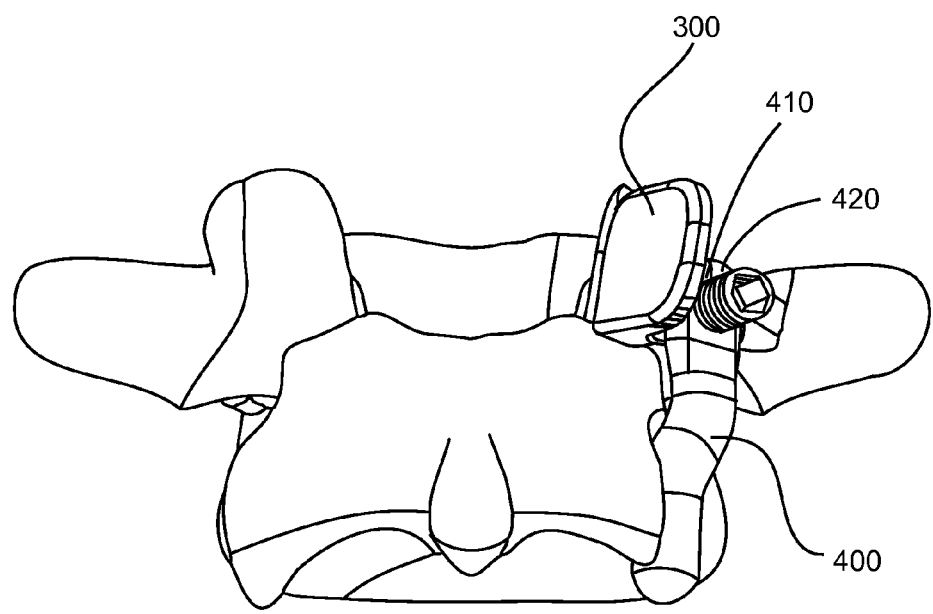
FIG. 23 is a dorsal view of the vertebra and the implant of FIG. 23 and also showing the addition of an inferior facet prosthesis.

FIG. 23 shows the addition of the inferior facet prosthesis 400 to the construct described in FIG. 22. The inferior facet prosthesis 400 generally has a shape similar to a longitudinal rod that is curved to match the contour of the inferior resection 121 (FIGS. 19 and 20). The inferior facet prosthesis 400 has an opening 410 through its superior end 420 that is shaped to surround the portion of the fixation element 200 that protrudes from the first resection surface 112. In FIG. 23, the inferior facet prosthesis 400 is placed over the superior facet prosthesis 300. However, the order of the placement of the prostheses can be reversed such that the inferior prosthesis 400 is placed on the fixation element 200 first followed by the superior prosthesis 300. When only the inferior facet 6 or the superior facet 43 is being replaced, only the appropriate (superior or inferior) facet prosthesis is placed on the fixation element 200 without the other (inferior or superior) facet prosthesis.

Because the various components of the implant are modular, many combinations of configurations and implant size, structure and shapes are feasible. For example, in a patient with unusual anatomy, the inferior facet prosthesis 400 may need to be larger than expected to conform to a particularly unusual or exceptionally large morphology of the inferior resection surface 121, and the superior facet prosthesis 300 may need to have an unusual angle to its articulating surface to conform to particular anatomic constraints. If this is the case, the modularity of the system allows for the surgeon to assemble an implant specifically designed to match the patient's anatomic structures during the surgery. This flexibility of a modular implant design allows the implant manufacturer to accommodate a large variation in anatomic structures with a limited selection of implant component sizes, shapes, and material types.

The modularity of the implant design also allows different components of the implant to be fabricated from different materials. Traditionally bone fixation implants such as the fixation element 300 are fabricated from biocompatible metals or alloys that provide sufficient strength and fatigue properties, such as cobalt chrome alloys, titanium and titanium alloys, and stainless steels. However, the fixation element 300 may be fabricated from ceramics, polymers, or biological materials such as allograft bone, composites, or other biocompatible structural materials. Likewise the superior facet prosthesis 300 and the inferior facet prosthesis 400 may be fabricated from metals, alloys, ceramics, polymers, biological materials, composites, or other biocompatible structural materials.

Figure 24:
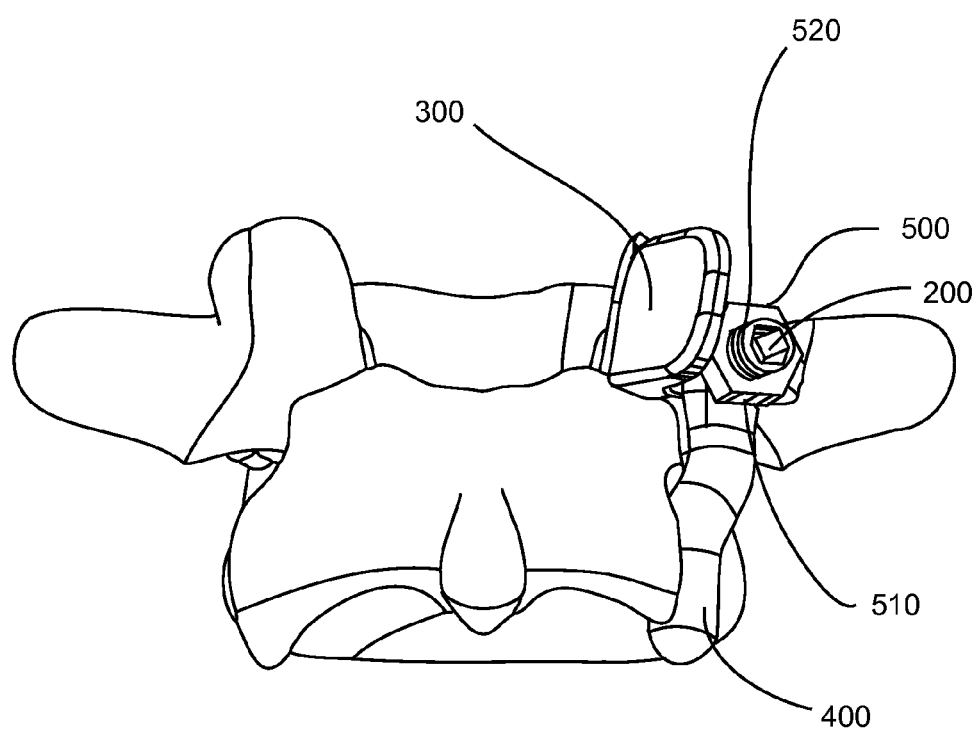
FIG. 24 is a dorsal view of the implant and vertebra of FIG. 23 and also showing the addition of an enlarged head that has the shape of a locking nut.

In FIG. 24, an enlarged head 500 is added to the fixation element 200 and is tightened down to force the prosthesis or prostheses into the bone to stabilize them. The enlarged head 500 shown in FIG. 24 has a hexagonal geometry on its external surface that is shaped to accept a driver (not shown) that is used to force an internal connection feature 520 (e.g., a screw thread) of the enlarged head 500 onto the connection feature 213 of the fixation element 200. In the case of the threaded embodiment of the connection feature 213, the enlarged head 500 is provided with a threaded connection feature 520 and is driven onto the fixation element 200 by turning the enlarged head 500 and allowing the threads to drive all components of the implant between the enlarged head 500 and the first resection surface 112 into the bone at or near the resection surface 112.

Figure 25:
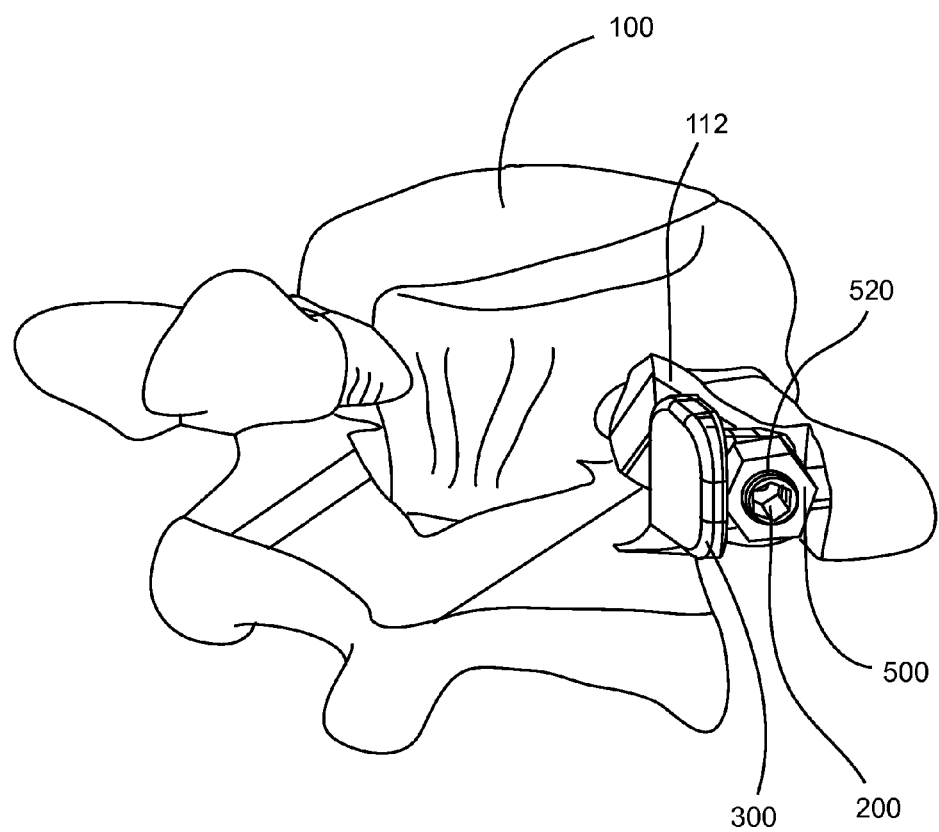
FIG. 25 is an isometric posteriolateral view of a vertebra with an assembled implant comprising a fixation element, superior facet prosthesis, and a locking nut.

FIG. 25 is an isometric posterior view of the assembly of the fixation element 200, the superior facet prosthesis 300, and the enlarged head 500 placed on the first resection surface 112. FIG. 26 is the same construct shown in FIG. 25, but with the implants and the vertebra 100 cut by a cross-sectioning plane 150 placed along an axis that passes through the center of the fixation element 200. The cross-section plan 150 shown cutting through the vertebra 100 and the implant in FIG. 26 is shown for visualization purposes to illustrate, using a cross-sectioned view, how the vertebra 100, fixation element 200, superior facet prosthesis 300 and the enlarged head 500 engage with each other. In actual surgery, it is highly unlikely that a surgeon would make a cut as illustrated by the cross-section 150 shown in FIG. 26.

FIG. 27 is a view of the vertebra 100 and the implant wherein the cross-section 150 shown in FIG. 26 is orientated such that the cross-section plane is facing the viewer. In FIG. 27, the fixation element 200 is in the vertebra 100. The embodiment of the fixation element 200 in FIG. 27 comprises a distal end 220 that is shaped to guide the fixation element 200 into bone tissue, a bone stabilizing portion 210 adjacent and proximal to the distal end, a shaft portion 240 adjacent and proximal to the bone stabilizing portion 210, a connection feature 213 adjacent and proximal to the shaft portion 240, and a drive feature 212.

The distal end 220 shown in FIG. 27 has a frustro-conical shape that allows the fixation element 200 to be driven or guided into the vertebra 100. The distal end 220 could be shaped in the form of a spade tip, trochar tip, or twist drill tip to assist in the guidance of the fixation element 200 in the vertebra 100. The fixation element 200 may also have a cutting flute (not shown) formed in the distal end 220 to help remove bone tissue and accommodate the guidance of the fixation element 200 in the vertebra 100. The fixation element 200 has a stabilizing portion 210 to help secure the fixation element 200 to the vertebra 100. This stabilizing portion 210 is a structure that can be the shape of various features that are designed to anchor into bone such as threads, ribs, grooves, slots, fins, barbs, splines, bone ingrowth surfaces, roughened surfaces, or any geometric feature that helps to engage the fixation element 200 with the bone tissue to help stabilize the fixation element 200. In FIG. 27, the stabilizing portion 210 is shown as a unitary continuous bone thread 231. However, other types of threads such as multiple lead threads, variable pitched thread, non-uniform pitch thread, buttress thread, or other thread forms, used on bone screws may be used. Because FIG. 27 is a cross-sectional view, the full length of the cannulation 211 is seen passing from the distal end 220 of the fixation element 200 to the proximal post 230 of the fixation element 200.

The drive feature 212 in the embodiment shown in FIG. 27 is an internal hex. However, any shape of drive feature 212 that transmits the loads necessary to drive the fixation element 200 into the vertebra 100 can be formed on the proximal post 230 of the fixation element 200. The depth of the drive feature 212 formed in the proximal post 230 of the fixation element 200 is seen in the cross-sectional view of FIG. 27. The drive feature 212 may be an internal drive feature such as the hex socket shown in this embodiment, or an external drive feature with geometry on the periphery of the proximal post 230 of the fixation element 200 that engages with a corresponding internal drive feature on a driver tool (not shown). In this embodiment the depth of the drive feature 212 is slightly longer than its cross-section is wide. This depth can be adjusted based on the material properties of the fixation element 200 and the drive tool (not shown).

The fixation element 200 is fabricated from biocompatible base materials that allow for the structural rigidity and strength needed. Examples of base materials that the fixation element 200 are made from include titanium, titanium alloys, cobalt-chrome alloys, stainless steel alloys, zirconium alloys, other biocompatible metal materials, biocompatible ceramics, biocompatible composites, and biocompatible polymers. The fixation element 200 may also have surface materials formed on the base material that allow for material properties specific to a particular portion of the fixation element 200. For example, the bone stabilization portion 210 could be coated with materials that allow for improved bone ingrowth into the implant surface such as a hydroxylapatite, bioceramic, Bioglass®, or other calcium phosphate derived material. The tribological bearing properties of the material in the areas that the fixation element 200 interfaces with other artificial elements may be improved by applying surface hardening techniques to the material of the fixation element 200 in these areas. Surface hardening techniques known in the materials science and materials engineering arts such as anodizing, ion implantation, and other techniques could be applied to these isolated areas.

A connection feature 213 is formed on the portion of the fixation element 200 that protrudes from the first resection surface 112. This connection feature 213 is designed to connect the enlarged head 500 to the fixation element 200. In the embodiment of the connection feature 213 shown in FIG. 21, threads 260 are on the external surface of this proximal section of the fixation element 200. These threads 260 engage with the threads on the internal connection feature 520 (FIG. 27) of the enlarged head 500. Although this connection feature 213 in this embodiment is threaded, other mechanical locking features (not shown) capable of locking the fixation element 200 and the enlarged head 500 together, such as press fit, taper fit, bonding fit by cement or glue, interference fit, expansion fit and mechanical interlocking fit such as a bayonet connection, can be used as the connection feature 213 (and a corresponding construction used on connection feature 520 of head 500).

Also shown in FIG. 27 is a cross-sectional view of an embodiment of the superior facet prosthesis 300. This embodiment of the superior facet prosthesis 300 has a flange 323 that has an opening 324 that wraps around the fixation element 200. In the assembled and implanted configuration of this embodiment, the flange 323 is positioned such that its bone contacting surface 322 makes contact with the first resection surface 112. Although not shown in this embodiment, other embodiments of the superior facet prosthesis 300 have structures (e.g., spikes) that protrude into the first resection surface 112 to help resist torsion and other anatomic loads. Protruding from the flange 323 at a given angle α, and a given distance X from the opening 324, is an articulating component 320. The articulating component 320 has an articulating surface 321 that replicates the natural articular surface of the replaced facet. Once the surgeon assesses the anatomy of the superior facet 43 that is being replaced, a particular superior facet prosthesis 300 is selected that has the angle α and the distance X that best fits the anatomy of the level of vertebra, the left or right side, and the size of the patient's anatomy being replaced. Thus a kit containing various sizes and shapes of superior facet prostheses 300 are provided to the surgeon and the surgeon selects the superior facet prosthesis 300 that best suits the situation.

After the fixation element 200 and the superior facet prosthesis 300 are selected and placed, they are locked to the vertebra by the enlarged head 500. As shown in FIG. 24, the enlarged head 500 in this embodiment has an internal connection feature 520 and a hexagonal shaped external drive feature 511C that is used to drive the enlarged head 500 over the fixation element 200 and against the superior facet prosthesis 300. The specific shape of the external drive feature 510 is dependent on the mating shape of the driver (not shown).

Figure 28:
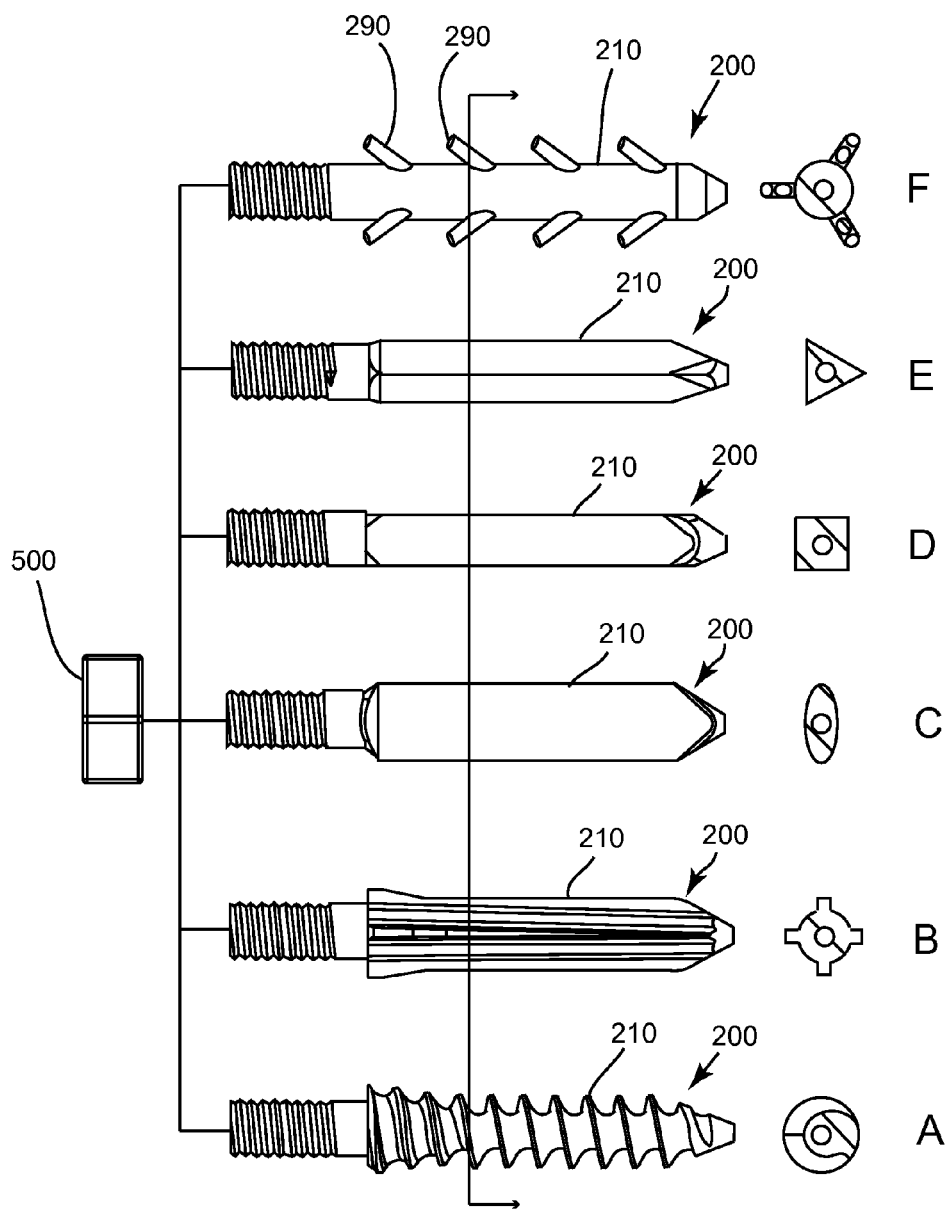
FIG. 28 is a side view of embodiments A, B, C, D, E, and F of the fixation element, and a cross-sectional view of the same embodiments, and a side view of the enlarged head in the shape of a locking nut.

Referring to FIG. 28, six different embodiments of the bone stabilization portion 210 of the fixation element 200 are shown that are labeled A, B, C, D, E, and F. The figure shows a side view of each fixation element 200 embodiment and a cross-sectional view of each embodiment to the right of the respective side view. To the left of the six embodiments is a representative enlarged head 500. Embodiment A is the threaded fixation element 200 embodiment shown in FIGS. 26 and 27 and described above. Embodiments B through E are various designs of fixation elements with non-circular cross-sections. Embodiment B is a four rib cruciate design with four longitudinal fins configured to resist torsion when the fixation element 200 is in the vertebra 100. Embodiment C is an oval shaped cross-section design that is wider in the first direction than the second direction to resist torsion. If the dimension of the width in the first and second directions is equal, the cross-section shape becomes more of a circle and bone stabilization portion 210 becomes more of a press-fit peg. Embodiment D is a square cross-section design with four approximately perpendicular sides, The corners of the sides help to resist torsion. Embodiment E is a triangular cross-section design with three sides to resist torsion. Embodiment F is an anchor-like design that is driven into the vertebra, with the wire arches or barbs 290 being compressed against the host bone and applying a radial expansion force so as to lock the structure to the bone.

Figure 28A:
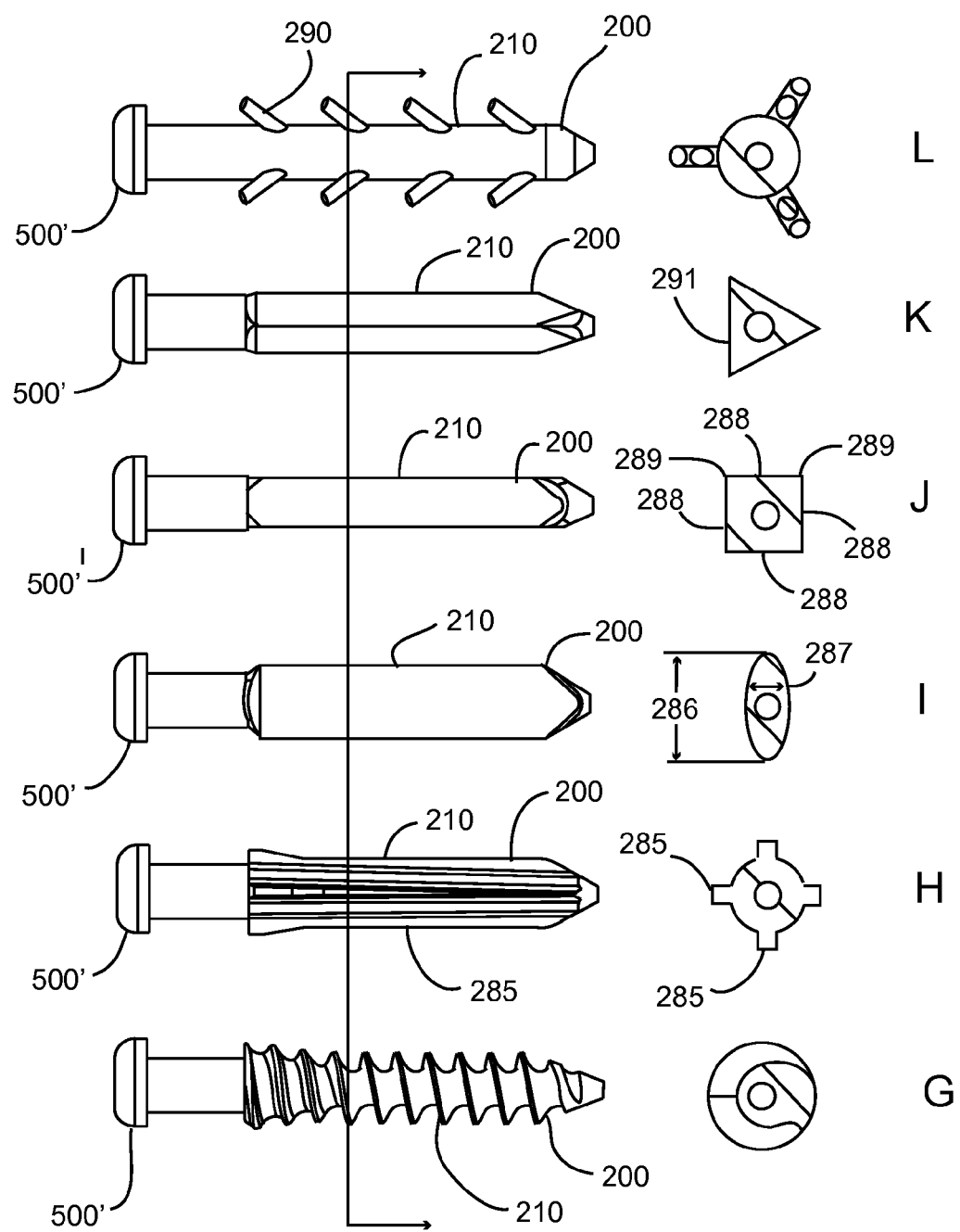
FIG. 28A is a side view of embodiments G, H, I, J, K, and L of the fixation element with attached enlarged heads, and a cross-sectional view of the same embodiments.

Referring to FIG. 28A, six more different embodiments of the bone stabilization portion 210 of the fixation element 200 are show that are labeled G, H, J, K, L, and I. FIG. 28A shows a side view of each fixation element 200 embodiment and a cross-sectional view of each embodiment to the right of the respective side view. Each embodiment has an attached enlarged head 500. Embodiment G is similar to the threaded fixation element 200 embodiment shown in FIGS. 10, 11, 12 and 24 and described above. Embodiments H through K are various designs of fixation elements 200 with non-circular cross-sections. Embodiment H is a four rib cruciate design with four longitudinal fins 285 configured to resist torsion when the fixation element 200 is in the vertebra 100. Embodiment I is an oval shaped cross-section design that is wider in the first direction 286 than the second direction 287 to resist torsion. If the dimension of the width in the first direction 286 and second direction 287 is equal, the cross-section shape becomes more of a circle and bone stabilization portion 210 becomes more of a press-fit peg. Embodiment J is a square cross-section design with four approximately perpendicular sides 288. The corners 289 of the sides 288 help to resist torsion. Embodiment K is a triangular cross-section design with three sides 291 to resist torsion.

Embodiment L is an anchor-like design that is similar to Embodiment F in FIG. 28, but with an attached enlarged head 500'. As embodiment L is, driven into the vertebra, wire arches or barbs 290 are compressed and apply radial expansion force against the wall of the prepared bone and into the pedicle bone P resulting in a locking anchor.

Figure 29:
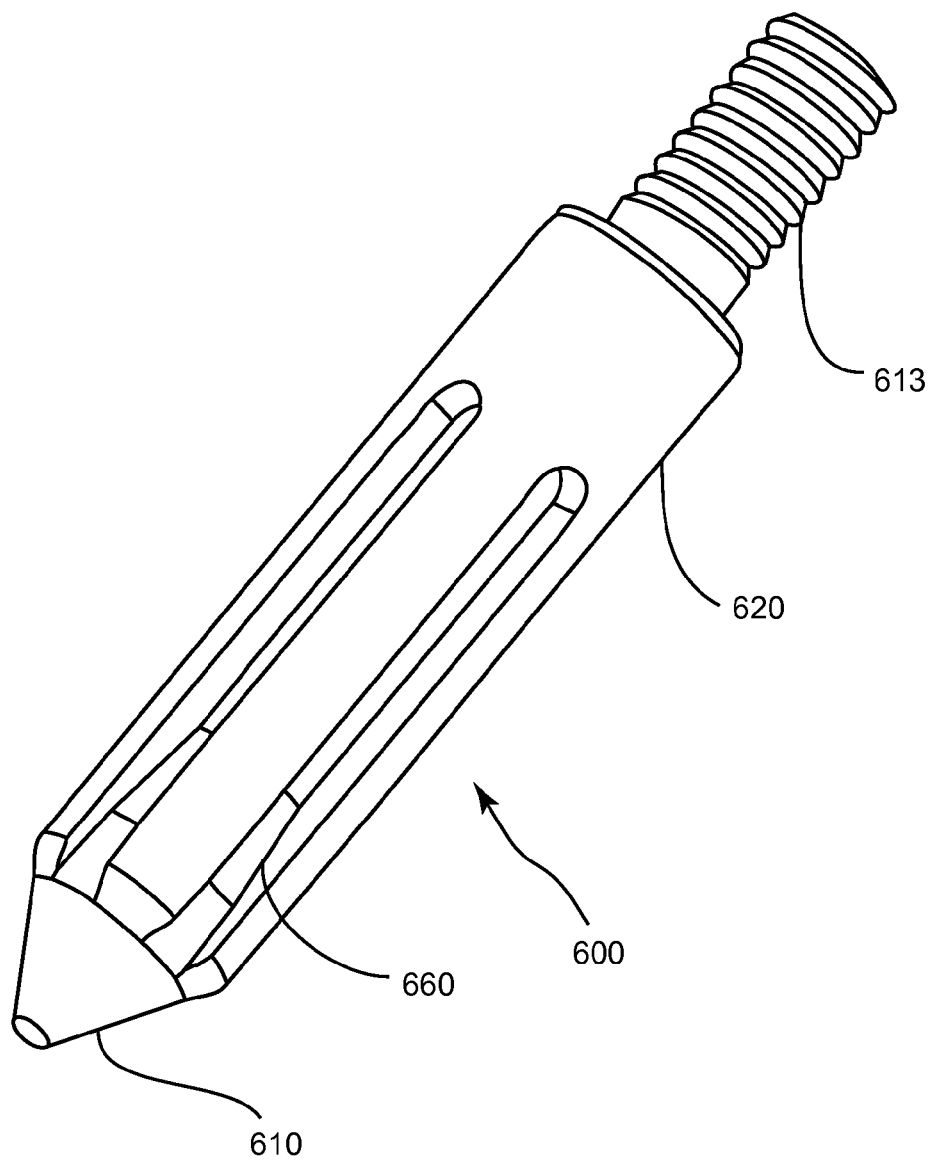
FIG. 29 is an isometric view of a radially expanding fixation element in its unexpanded state.
Figure 30:
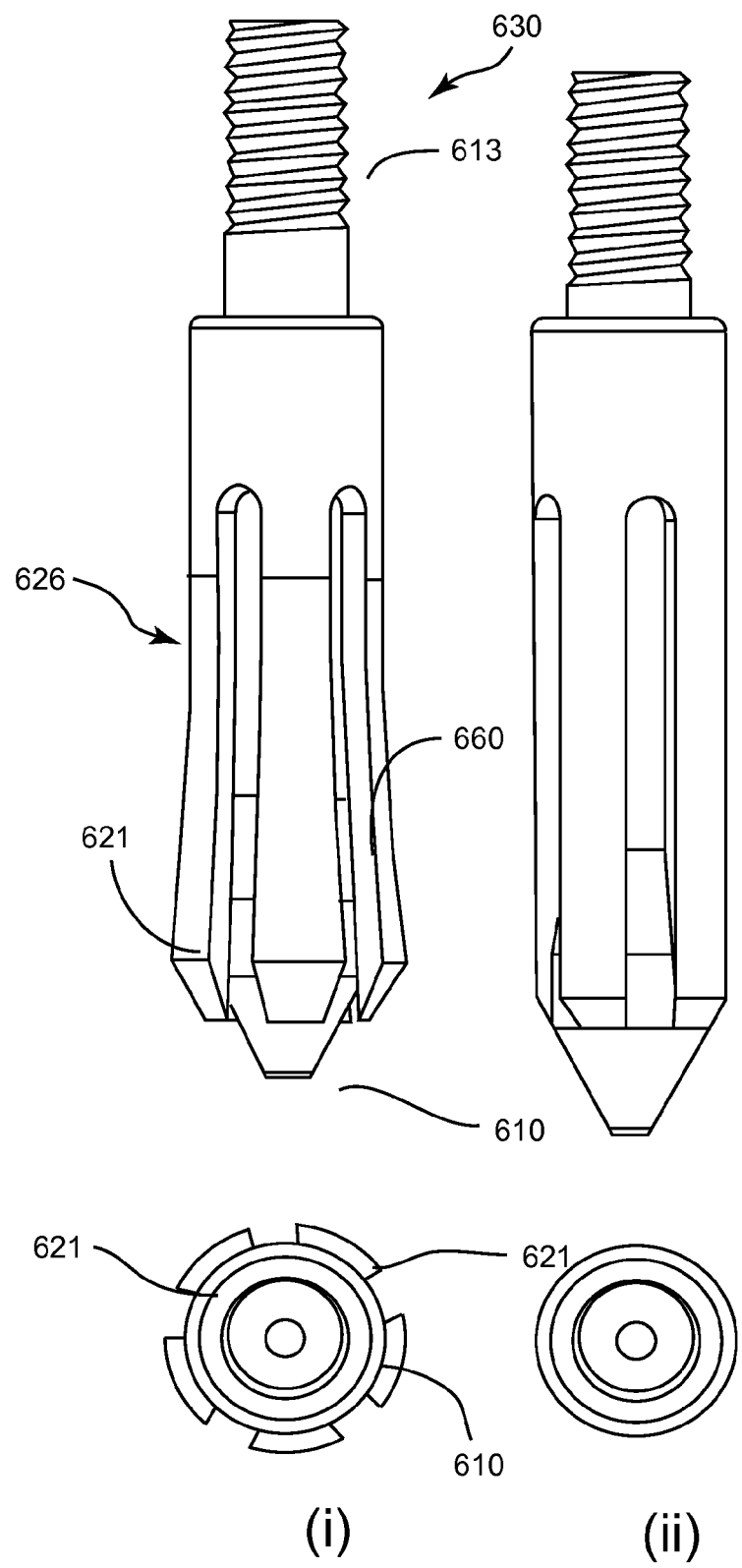
FIG. 30 is a side view and a bottom view of (i) an expanded radially expanding fixation element and (ii) an unexpanded radially expanding fixation element.

FIG. 29 is an isometric view of a radially expanding fixation element 600. The radially expanding fixation element 600 comprises two main elements, an expansion sleeve 620 and a central element 610 that is inside of the expansion sleeve 620. The radially expanding fixation element 600 is placed into the vertebra and then the central element 610 is pulled relative to the expansion sleeve 620 resulting in radial expansion of the fixation element 600. This is shown in FIG. 30. As the proximal post 630 of the central element 610 is pulled axially along its longitudinal axis, and the expansion sleeve is held axially in the bone by compression fit, talons 621 on the expansion sleeve 620 are radially expanded outward by a mandrel 660 on the central element 610. The talons or fingers 621 provide both torsional and axial stability to the radially expanding fixation element 600. This provides a secure fixation element for fixation of the remaining components of the implant.

Figure 31:
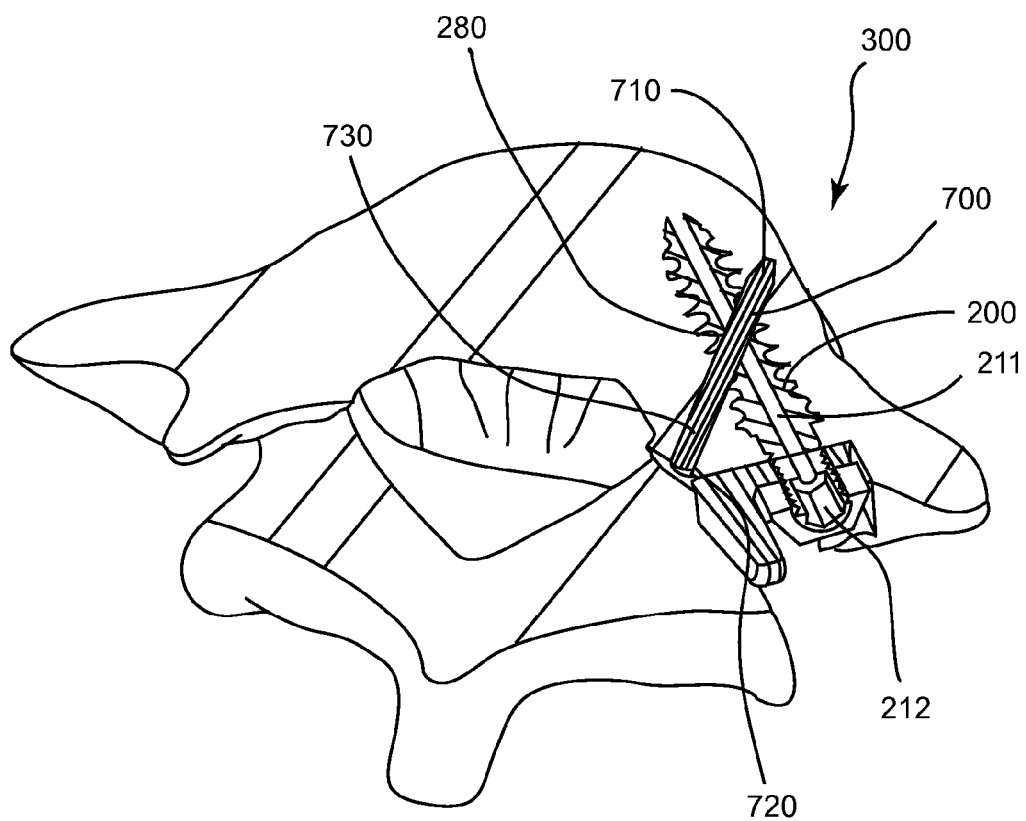
FIG. 31 is an isometric cross-sectional view of a vertebra and a facet implant showing a cross-pin torsionally and axially securing the fixation element.

FIG. 31 shows a cross-pin element 700 engaged with the fixation element 200 to help secure the fixation element 200 both torsionally and axially. The cross-pin element 700 is columnar in shape having a distal end 710, mid section 730 (with a length along its longitudinal axis that is longer than its transverse cross-sectional width), and a proximal post 720. The distal end 710 is shaped to penetrate through bone tissue and into a cross hole 280 formed in the fixation element 200. Instrumentation (not shown) is used to align the cross-pin element 700 with the cross-hole 280 by fixing to the drive feature 212 or the cannulation 211 on the fixation element 200 and aligning the direction of insertion of the cross-pin element 700 with the cross-hole 280. Once the cross-pin element 700 is in place in the bone and through the fixation element 200, the torsional and axial stability of the fixation element 200 is improved.

The various embodiments of the fixation element 200 described above and shown in FIG. 28 through FIG. 31 function in conjunction with the enlarged head 500 to hold the inferior facet prosthesis 400 and/or the superior facet prosthesis 300 to their respective resection surfaces. Various combinations of this modular implant will be described below and shown in FIGS. 32 through 37. Although these figures show a fixation element 200 and enlarged head 500 as the means of securing the prostheses to the vertebra, other clamping means such as the screw fastener 17 (FIG. 10) may be used to mount the prosthesis to the bone. For example, the screw prostheses 17 shown in FIGS. 10 through 12 passes through either the opening 324 (FIG. 22) in the superior facet prosthesis 300 or the opening 410 (FIG. 23) in the inferior facet prosthesis 400 or through both of these openings wherein the head of the screw fastener 17 acts as the securing means pressing the inferior facet prostheses 400 and the superior facet prosthesis 300 against their respective resection surfaces.

FIGS. 32 through 37 demonstrate different combinations of assemblies of the facet replacement prosthesis. The basic components of the prosthesis are the fixation element 200, superior facet prosthesis 300, inferior facet prosthesis 400, and the enlarged head 500. However, as described above, a screw fastener 17 can replace the fixation element 200 and the enlarged head 500.

Figure 32:
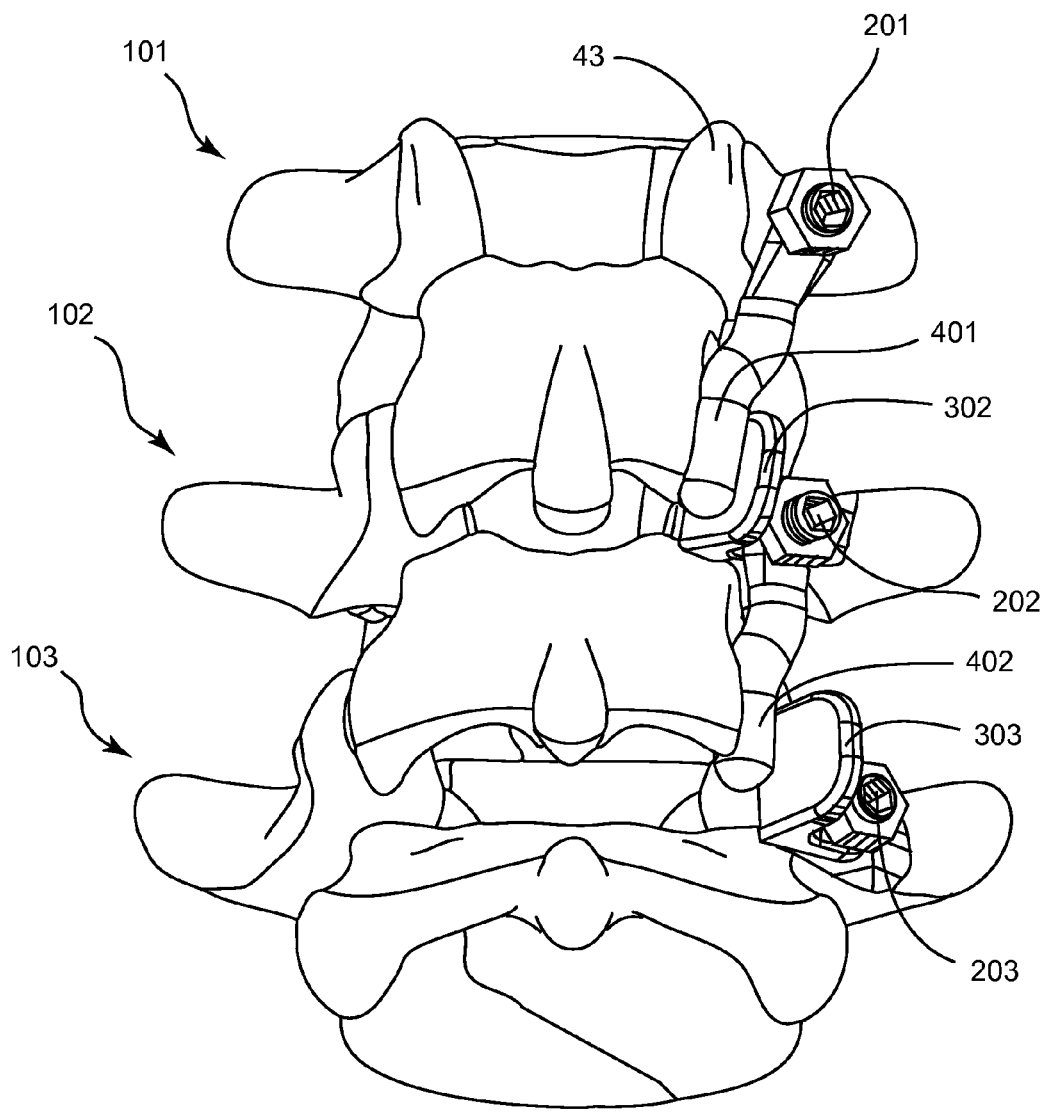
FIG. 32 is a dorsal view of a spinal section showing a top, middle, and bottom vertebra with unilateral facet replacements on the right side of the spine section, both between the top and middle vertebra, and between the middle and bottom vertebra.

Referring to FIG. 32, three sequential layers of vertebra are shown, the top vertebra 101 is above the middle vertebra 102 that is shown above the bottom vertebra 103. Portions of some of the facets on the right side of the vertebrae are replaced by prostheses. Looking at the facet joint between the top vertebra 101 and the middle vertebra 102, inferior facet prosthesis 401 is articulating against superior facet prosthesis 302 to form an artificial unilateral joint. The inferior facet of the middle vertebra 102 is replaced by inferior facet prosthesis 402 and the superior facet of the bottom vertebra 103 is replaced by superior facet prosthesis 303. Thus, a second unilateral prosthetic joint is formed that is also on the right side and is located at the level between the middle vertebra 102 and the bottom vertebra 103. FIG. 32 demonstrates the difference in shape of the inferior facet prosthesis 401 that is; implanted around the fixation element 201 without a superior facet prosthesis 300 and an inferior facet prosthesis 402 that is implanted around a fixation element 202 and over a superior facet prosthesis 302. The opening 410 of the inferior facet prosthesis 401 on the top vertebra 101 in this assembly is offset more laterally than the opening 410 in the inferior facet prosthesis 402 for the middle vertebra 102. This is because the fixation element 201 is implanted more laterally on the top vertebra 101 to preserve more of the superior facet since it is not replaced by a prosthesis at this level.

Figure 33:
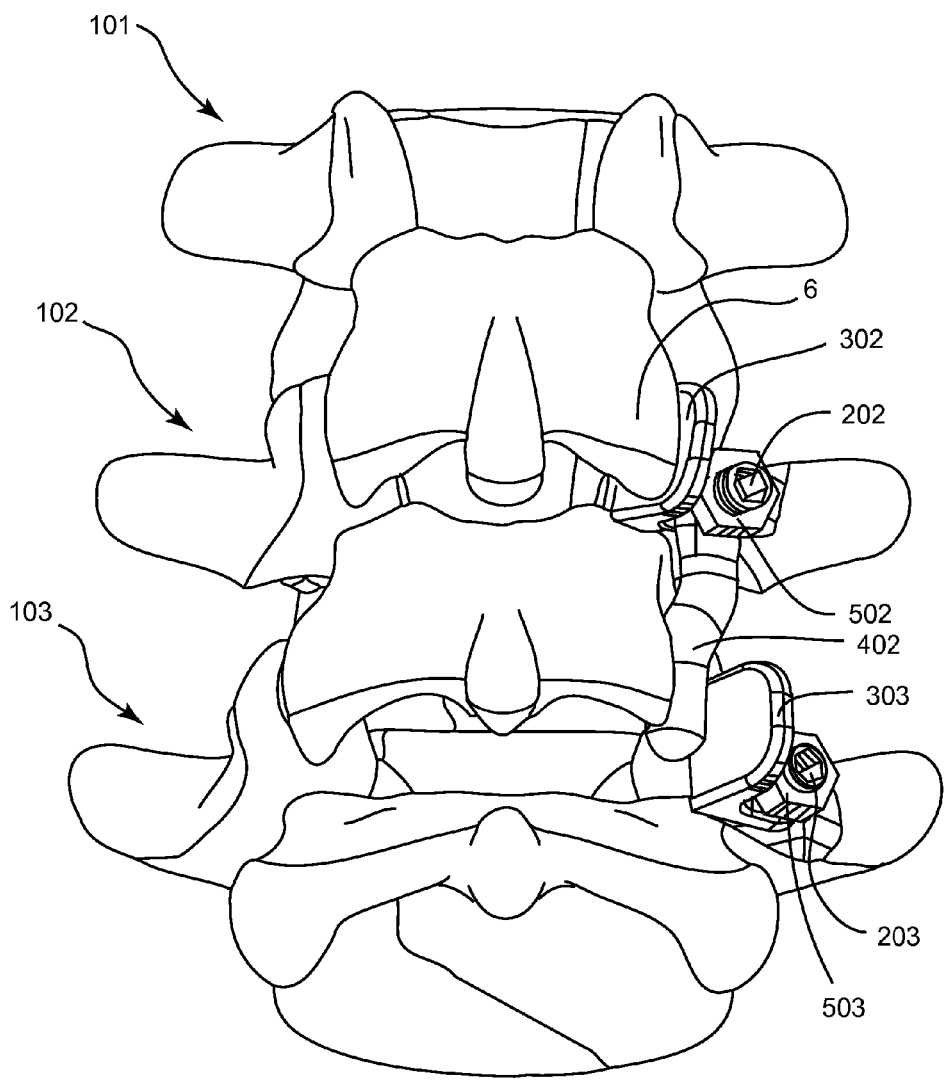
FIG. 33 is a dorsal view of a spine section showing a superior hemiplasty facet replacement between the top and the middle vertebra and unilateral replacement between the middle and the bottom vertebra.

Referring to FIG. 33, the top vertebra 101 is left intact without resection of the facets. Portions of both the superior and inferior facets on the right side of the middle vertebra 102 are replaced by superior facet prosthesis 302 and an inferior facet prosthesis 402. Only the right superior facet of the bottom vertebra 103 is replaced (i.e., by a superior facet prosthesis 303) in FIG. 33. Thus, a hemiplasty replacement results on the right facet joint between the top vertebra 101 and the middle vertebra 102 and a unilateral replacement results between the middle vertebra 102 and the bottom vertebra 103. This assembly shown in FIG. 33 demonstrates how the superior facet prosthesis 302 can articulate against a natural inferior facet 6 or superior facet prosthesis 303 can articulate against an inferior facet prosthesis 402.

Figure 34:
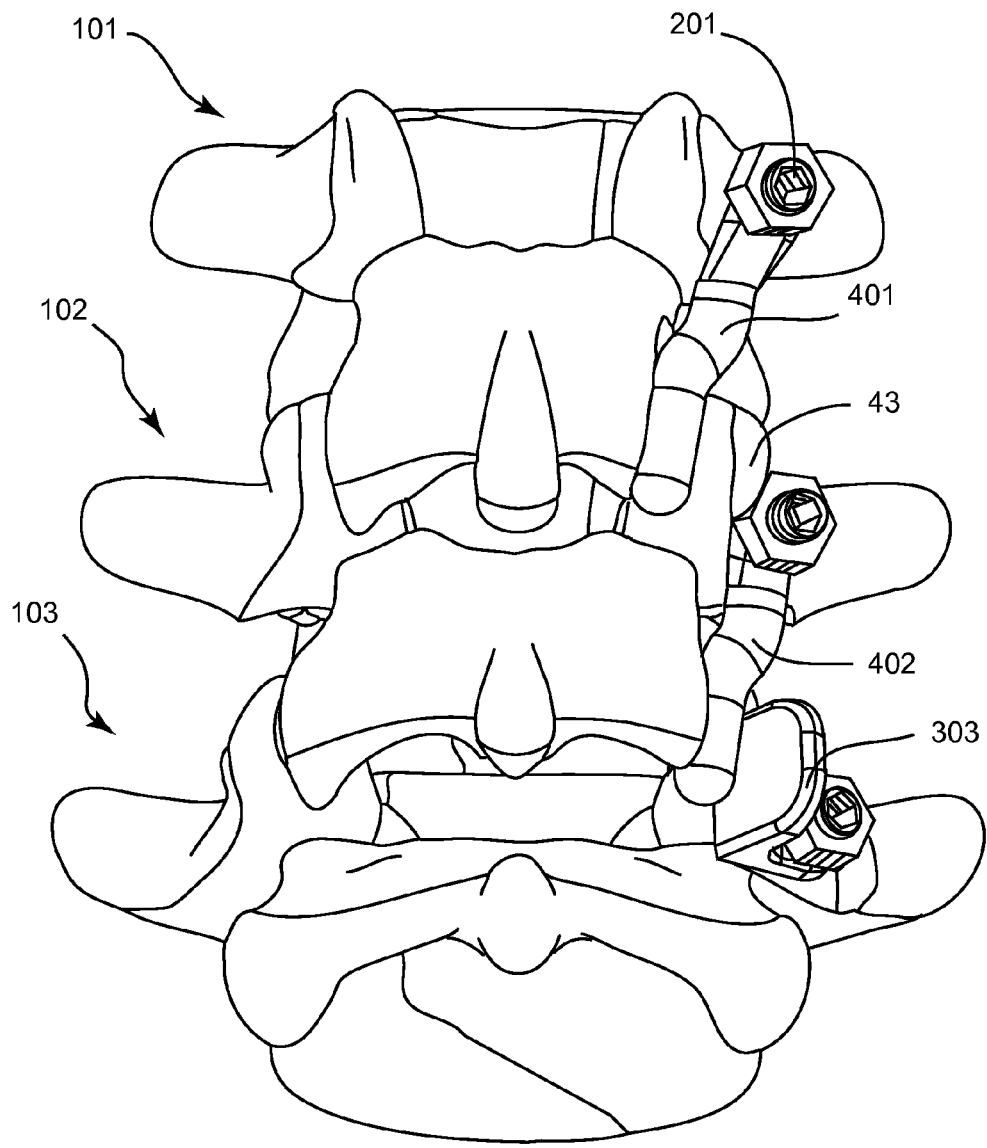
FIG. 34 is a dorsal view of a spinal section showing an inferior facet hemiplasty replacement between the top and the middle vertebra and a unilateral replacement on the right side between the middle and the bottom vertebra.

FIG. 34 shows how an inferior facet prosthesis 401 can articulate against a natural superior facet 43, or a inferior facet prosthesis 402 can articulate against superior facet prosthesis 303. The right facet joint between the top vertebra 101 and the middle vertebra 102 is a hemiplasty replacement with the inferior facet replaced by an inferior facet prosthesis 401. The right facet joint between the middle vertebra 102 and the bottom vertebra 103 is a unilateral replacement with the inferior facet replaced by in inferior facet prosthesis 402 and the superior facet of the bottom vertebra 103 replaced by a superior facet prosthesis 303.

Figure 35:
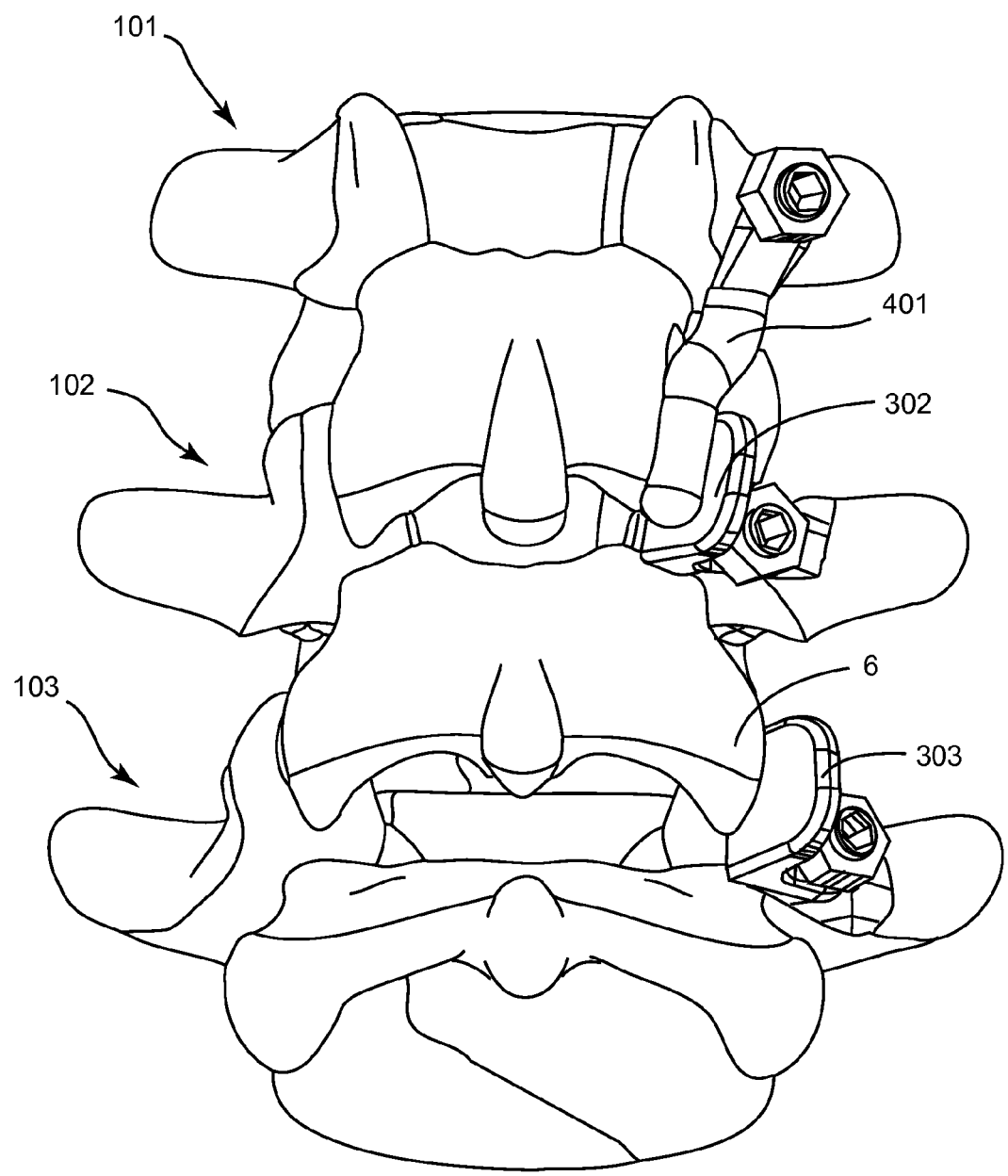
FIG. 35 is a dorsal view of a spinal section showing a unilateral replacement between the top and the middle vertebra on the right side, and an inferior facet hemiplasty replacement between the middle and the bottom vertebra on the same side.

FIG. 35 shows another example of how the superior facet prosthesis 303 can articulate against a natural inferior facet 6 or superior facet prosthesis 302 can articulate against an inferior facet prosthesis 401. In this assembly of the implant, the right side between the top vertebra 101 and the middle vertebra 102 is a unilateral replacement and the right side between the middle vertebra 102 and the bottom vertebra 103 is a hemiplasty replacement.

Figure 36:
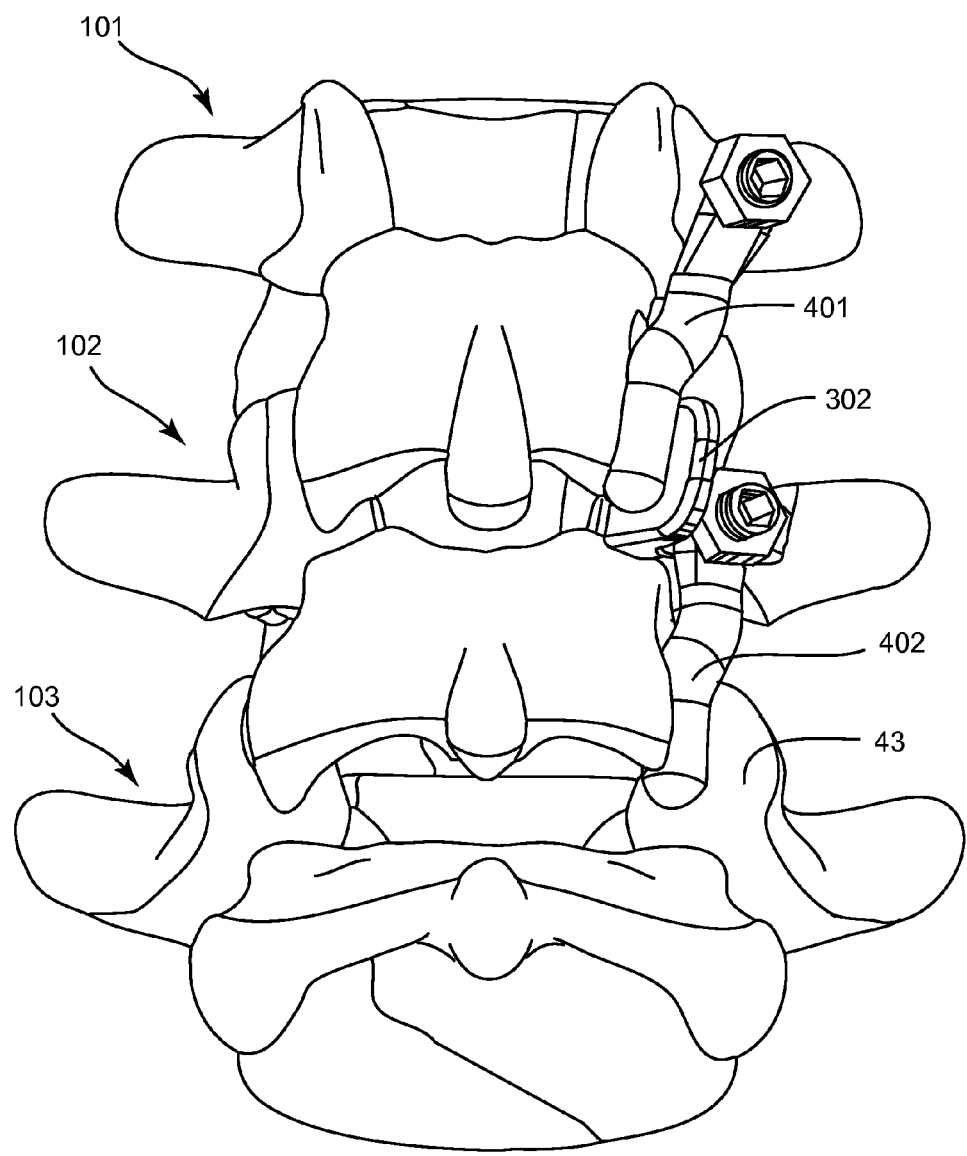
FIG. 36 is a dorsal view of a spinal section showing a unilateral replacement between the top and the middle vertebra on the right side and a superior facet hemiplasty replacement on the right side between the middle and the bottom vertebra on the same side.

FIG. 36 shows another example of how an inferior facet prosthesis 402 can articulate against a natural superior facet 43, or an inferior facet prosthesis 401 can articulate against superior facet prosthesis 302. The right facet joint between the top vertebra 101 and the middle vertebra 102 is an unilateral replacement with the inferior facet replaced by an inferior facet prosthesis 401 and the superior facet of the middle vertebra 102 replaced by a superior facet prosthesis 302. The right facet joint between the middle vertebra 102 and the bottom vertebra 103 is a hemiplasty replacement with the inferior facet replaced by an inferior facet prosthesis 402.

Figure 37:
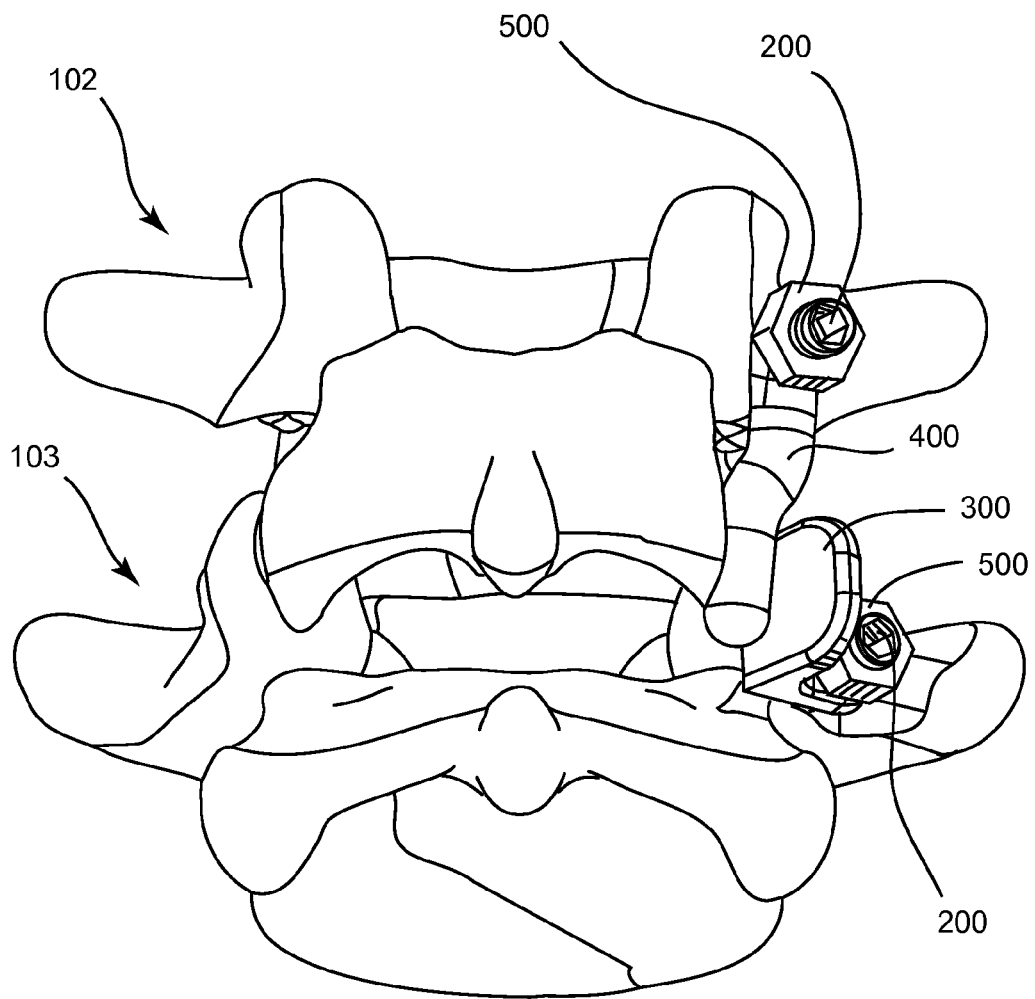
FIG. 37 is a spinal section of two vertebra showing the inferior facet of the top vertebra and the superior facet of the joining bottom vertebra replaced by an articulating facet implant.
Figure 38:
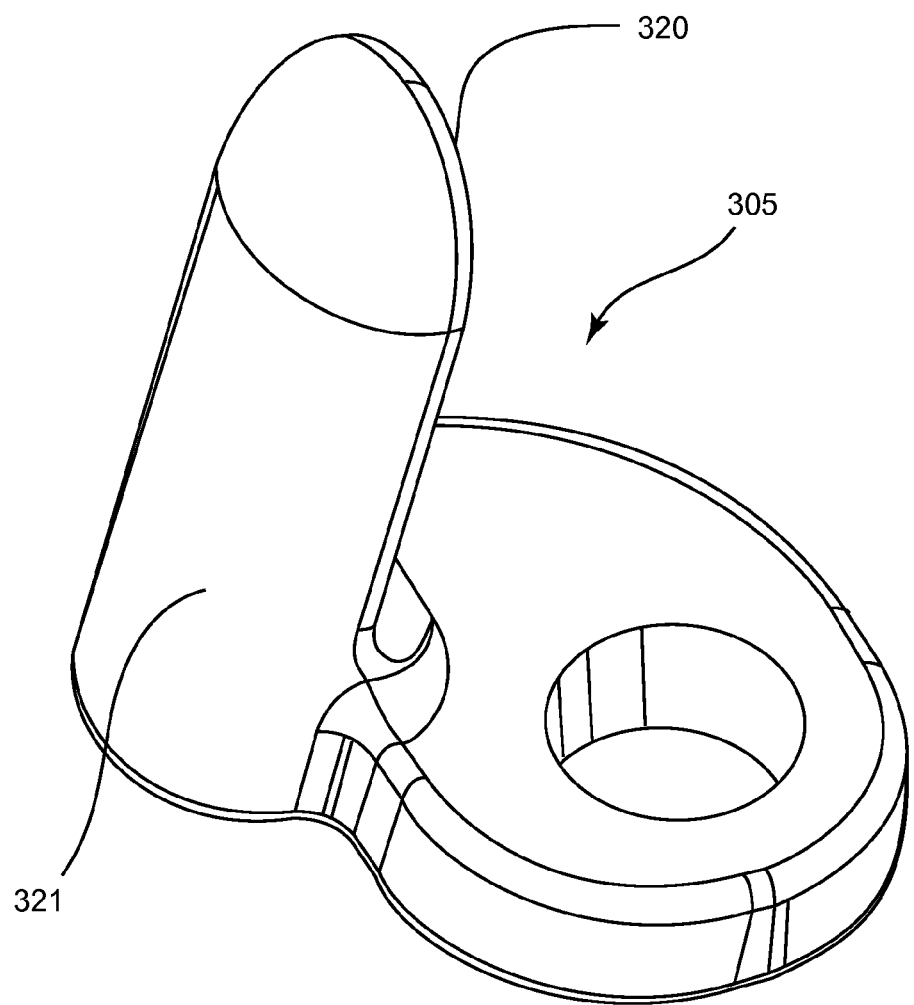
FIG. 38 is an isometric view of a curved superior facet prosthesis.
Figure 39:
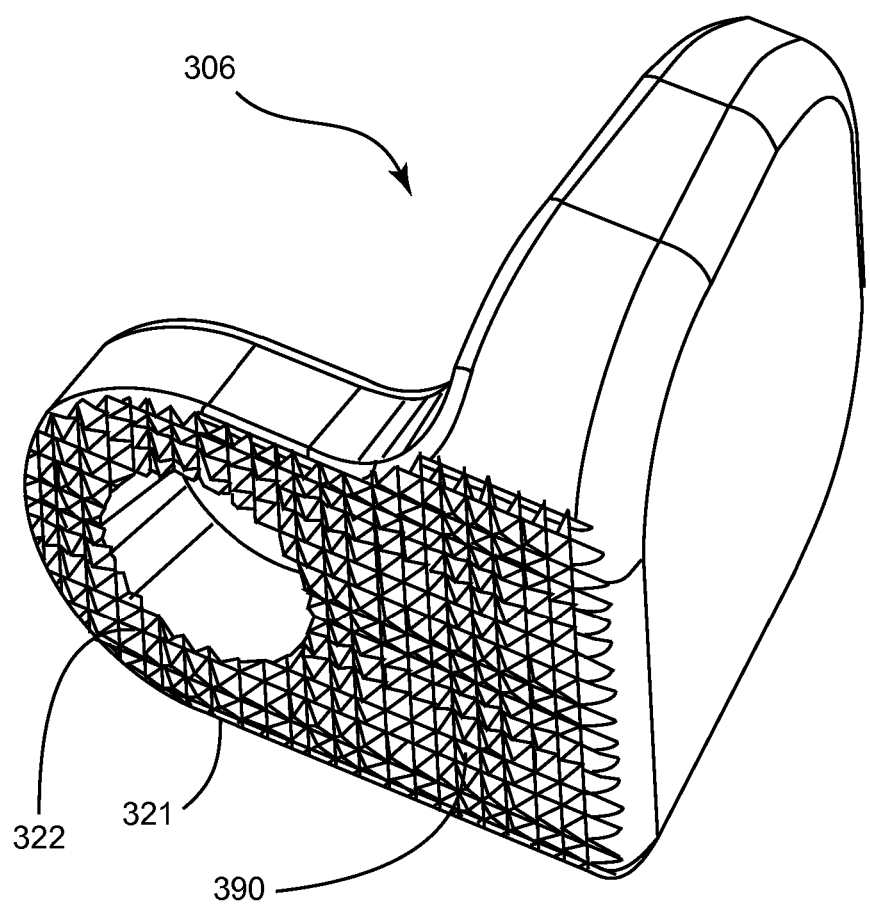
FIG. 39 is an isometric view of the bone ingrowth surface on a superior facet prosthesis.

The assembly of the implant shown in FIG. 37 demonstrates only one level, that between the middle vertebra 102 and the bottom vertebra 103, being replaced on the right side FIG. 38 and FIG. 39 show two embodiments of the superior facet prosthesis. The embodiment shown in FIG. 38 is curved superior facet prosthesis 305 with a curved articulating component 320 that has a curved articulating surface 321. This curved articulating surface 321 allows for a more distributed contact load between an inferior facet prosthesis 400 and the curved articulating surface 321. This allows slightly more flexibility in the position that the surgeon places the curved superior facet prosthesis 305 than the superior facet prosthesis 300 previously described. The articulating surface 321 of the superior facet prosthesis 300 previously described is relatively flat. The articulating surface 221 of the curved superior facet prosthesis 305 is curved. Since the bearing portion of the inferior facet prosthesis 400 is columnar, the two prosthesis can be aligned on a slight mismatch and make more of an anatomic contact if the articulated surface is curved as in FIG. 38.

FIG. 39 illustrates bone ingrowth feature 390 on the superior facet prosthesis 306. This bone ingrowth feature can be any surface that allows bone to grow into the implant between the first resection 111 of the vertebra and the 322 bone-contacting surface 321 of the implant. Examples of bone ingrowth features 390 include porous coating of beads or meshes, electrochemically etched shapes and porous pads pressed onto the implant surface made from tantalum, titanium, cobalt chrome alloys or and other biocompatible material such as hydroxylapatite or calcium phosphate ceramics.

Figure 40:
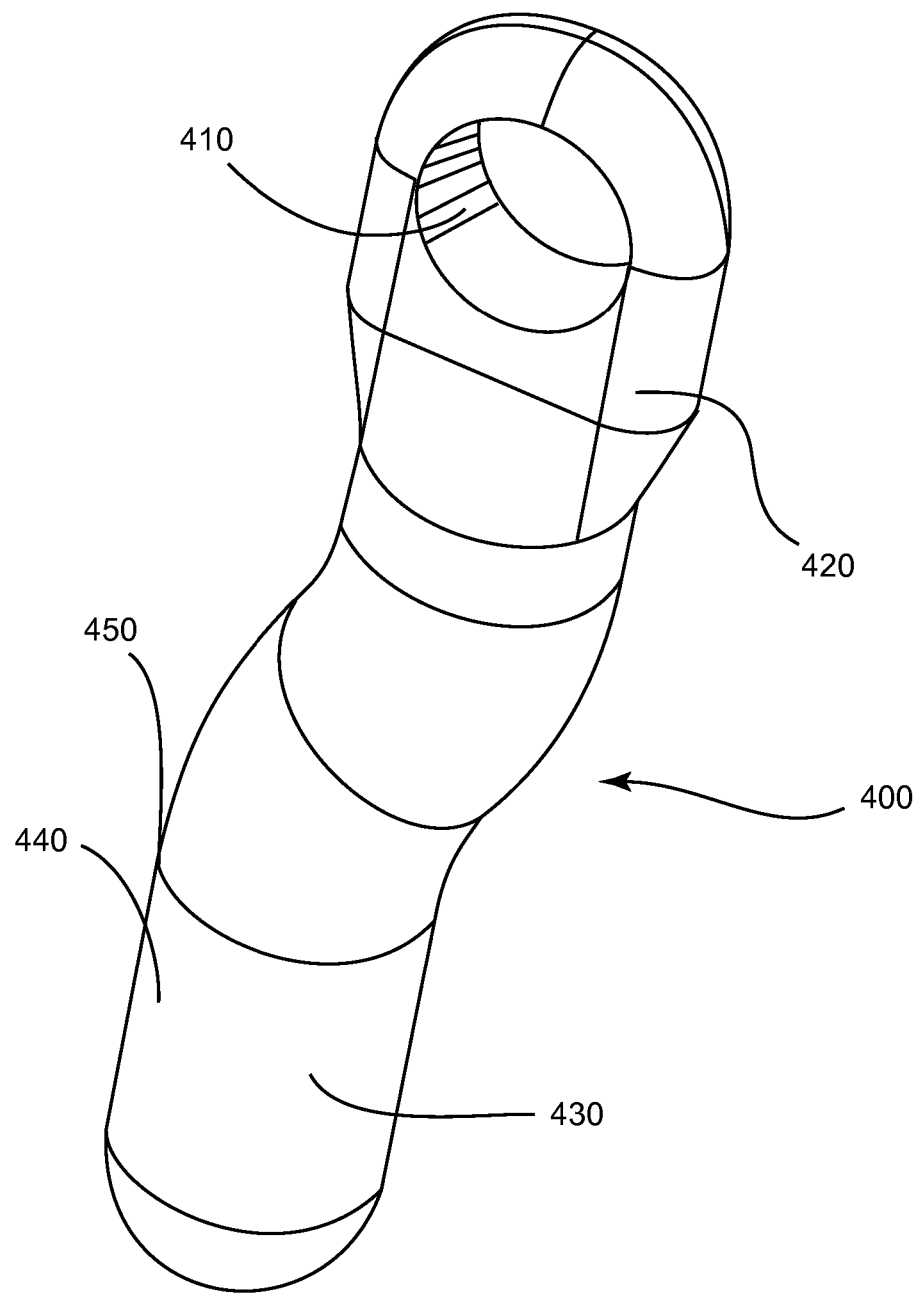
FIG. 40 is an isometric view of an inferior facet prosthesis.

FIG. 40 shows an isometric view of an inferior facet prosthesis 400 formed in the general shape of a finger or talon. More particularly, inferior facet prosthesis 400 is formed with a flange 420 on its superior side shaped to either fit between the superior facet prosthesis 300 and the enlarged head 500, or between the first resection surface 112 and the enlarged head 500. The flange 420 has an opening 410 through it that is dimensioned to allow the inferior facet prosthesis 400 to fit over the proximal end 210 or the fixation element 200 and around the post of the fixation element 200. The inferior facet prosthesis 400 also has an inferior portion 450 on the opposite side of the flange 420 that has a bone apposition side 440 that is shaped to contact the surface of the resected bone 121 (FIG. 19) and joint articulation side 430 that is shaped to articulate with a natural or prosthetic superior facet.

Figure 41:
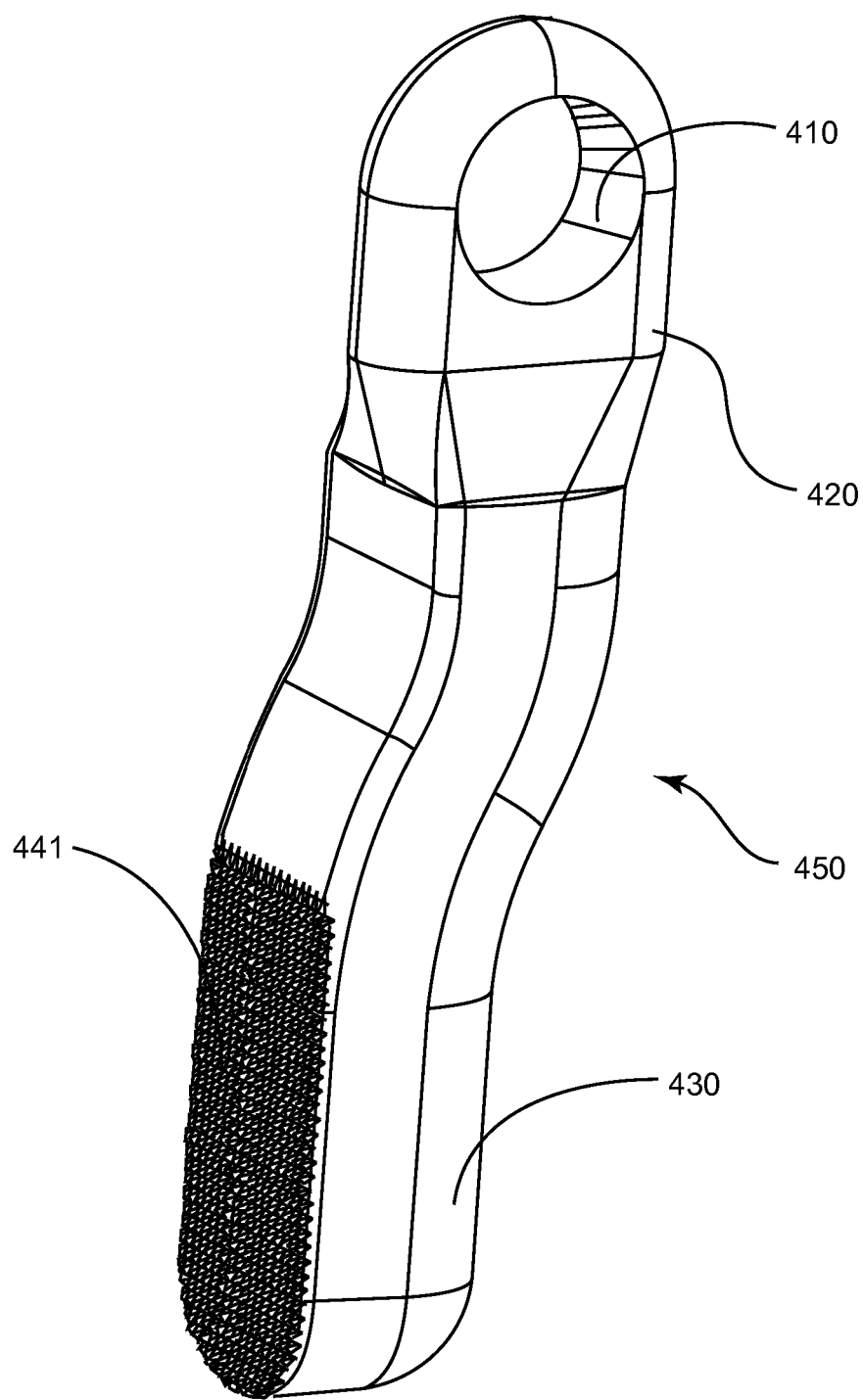
FIG. 41 is an isometric view of an inferior facet prosthesis with a bone ingrowth surface.

FIG. 41 shows an isometric view of an inferior facet prosthesis 400 also formed in the general shape of a finger or talon. Inferior facet prosthesis 400 is formed with a superior end 420 having an opening 410 that is dimensioned and shaped to accept the fixation element 200. The inferior facet prosthesis is generally columnar in shape, having a curved length designed to conform to the prepared anatomy of the vertebra 100. The inferior facet prosthesis 400 of FIG. 41 has an inferior portion 450, which is shown opposite the superior end 420, and slightly medially offset from the superior end 420. This medial offset of the opening 410 relative to the inferior portion 450 allows the inferior facet prosthesis 400 to be anchored to the bone by the fixation element 200 and secured to the bone by the enlarged head 500, or the superior facet prosthesis 300 in combination with the enlarged head 500, at an anatomical position that allows optimal bone fixation. The inferior facet prosthesis embodiment of FIG. 41 has a bone ingrowth surface 441 and an articulating surface 430 on its inferior end 450. In this embodiment, the bone ingrowth surface 441 is a textured structure that permits bone cells to grow into the implant surface. The shape of the bone ingrowth surface 441 can be a uniform textured surface as shown in FIG. 41, or can be a non-uniform randomized structure such as a open cell foam structure, a porous beaded structure, a wire mesh structure, an electrochemical etched structure, or other bone ingrowth structures known in the design of orthopedic implants. The bone ingrowth surface is shaped to mate with the inferior resected bone surface 121 such as shown in FIG. 19 and FIG. 20.

Figure 42:
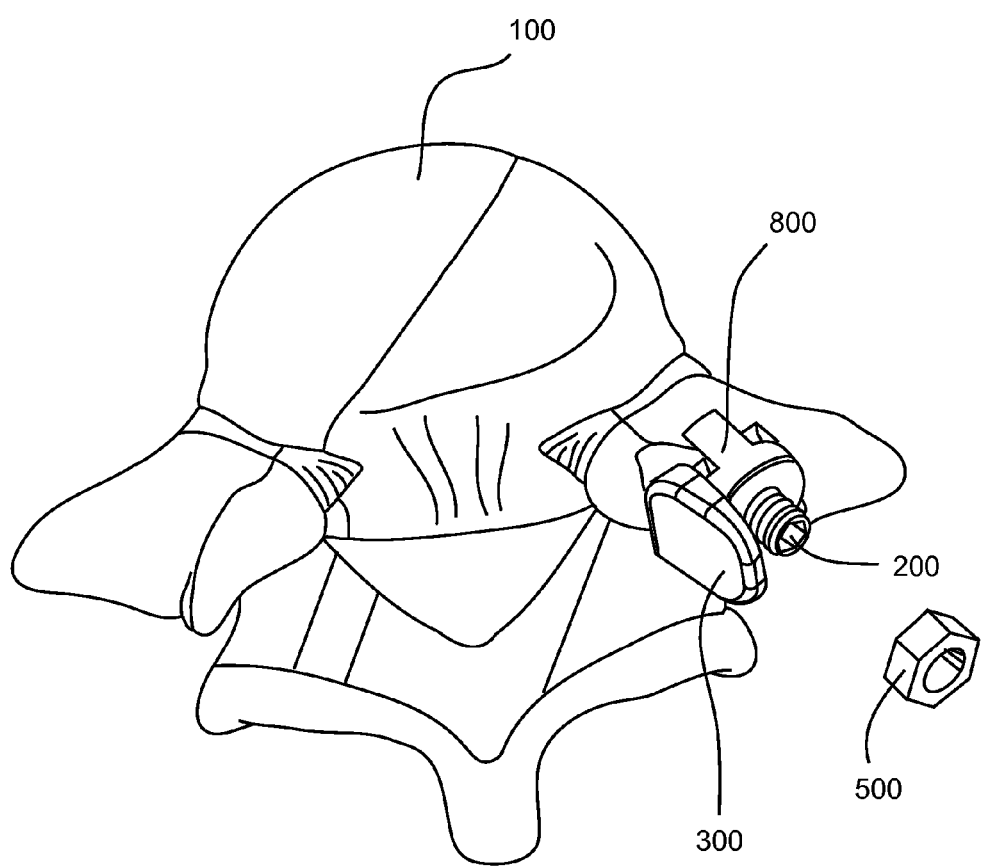
FIG. 42 shows the addition of a locking washer to the construction of the implant shown in FIG. 25.

FIG. 42 shows a posterior isometric view of an embodiment of the superior facet implant 300 that has an additional locking washer 800 to assist in stabilizing the superior facet implant to the first resection surface 112. The construction of the implant assembly shown in FIG. 42 is similar to that of the assembly shown in FIG. 25 with the addition of the locking washer 800 that is placed over and around the superior facet implant 300.

Figure 43:
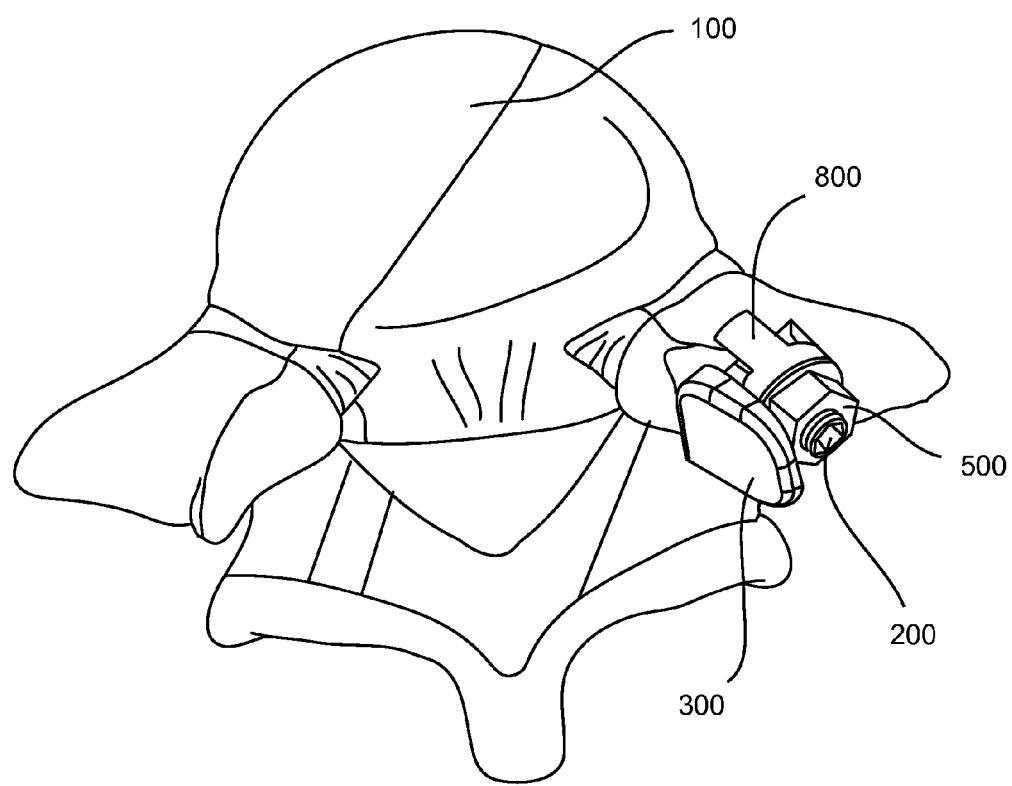
FIG. 43 shows the assembly of the construct shown in FIG. 42.

FIG. 43 shows the same implant of FIG. 42 with the enlarged head 500 locked onto the fixation element 200 and pushing the locking washer 800 against the superior prosthesis 300 and into the bone tissue. This added bone penetration of the locking washer 800 helps to fix the superior prosthesis 300 such that the entire assembly is more mechanically stable with respect to the vertebra 100.

FIG. 43 shows a further step in the assembly of the implant construct described in FIG. 42. In FIG. 43, the locking washer 800 is secured over the fixation element 200 and into the bone tissue by the enlarged head 500. Although this embodiment of the locking washer 800 is only shown with the superior facet prosthesis 300, the locking washer 800 can also be used to mechanically secure the inferior facet prosthesis 400 and the combination of the inferior facet prosthesis 400 and the superior facet prosthesis 300. In the embodiment of the locking washer 800 shown in FIG. 42 and FIG. 43, the locking washer 800 is placed over the superior facet prosthesis 300. However, the locking washer 800 may be placed under the superior facet prosthesis 300 or under any other combination of inferior facet prosthesis 400 and superior facet prosthesis 300, or between the superior facet prosthesis 300 and the inferior facet prosthesis 400 to stabilize the implant construct.

Figure 44:
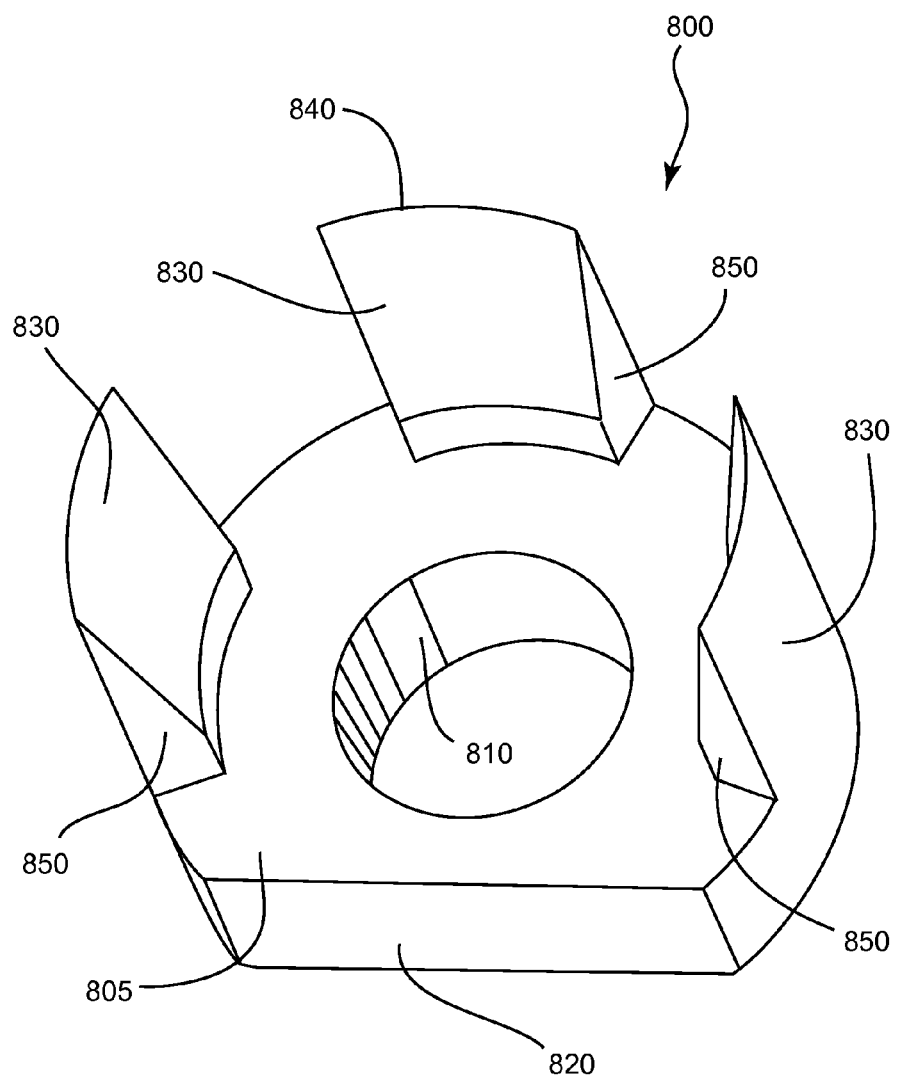
FIG. 44 shows an isometric view of the locking washer shown in FIG. 42.

FIG. 44 shows an isometric view of the locking washer 800. The locking washed 800 has an opening 810 in the body 805 that is dimensioned to fit over the proximal post 230 of the fixation element 200. The locking washer 800 also has an anti-rotation feature 820 that mates with either the superior facet prosthesis 300 or the inferior facet prosthesis 400 or a combination of both the inferior facet prosthesis 400 and the superior facet prosthesis 400. The anti-rotation feature 820 shown in this embodiment is a flat surface, however, any feature that would rotationally constrain the locking washer 800 to the other components of the implant (such as a tab, groove, taper or other geometric shape) can be formed on the washer as a anti-rotation feature 820. The locking washer 800 also has prongs 830 that pass into the bone tissue of vertebra 100 to help stabilize the implant construct. The prongs in this embodiment of the locking washer 800 are elongated protrusions that taper to a tissue penetration tip 840. The prongs have sidewalls 850 that provide a surface to resist torsion once the locking washer 800 penetrates the bone tissue. The prongs 830 may also be simple spikes that are either symmetrical or nonsymmetrical in cross-section that protrude from the locking washer body 805. The shape and length of the locking washer prongs 830 is dependent on how the locking washer is used. The prongs 830 of the locking washer 800 that holds only one of the inferior facet prosthesis 400 or the superior facet prosthesis 300 to the vertebra 100 may be shorter than the prongs 830 of the locking washer 800 that holds both the inferior facet prosthesis 400 and the superior facet prosthesis 300 to the vertebra 100.

Figure 45:
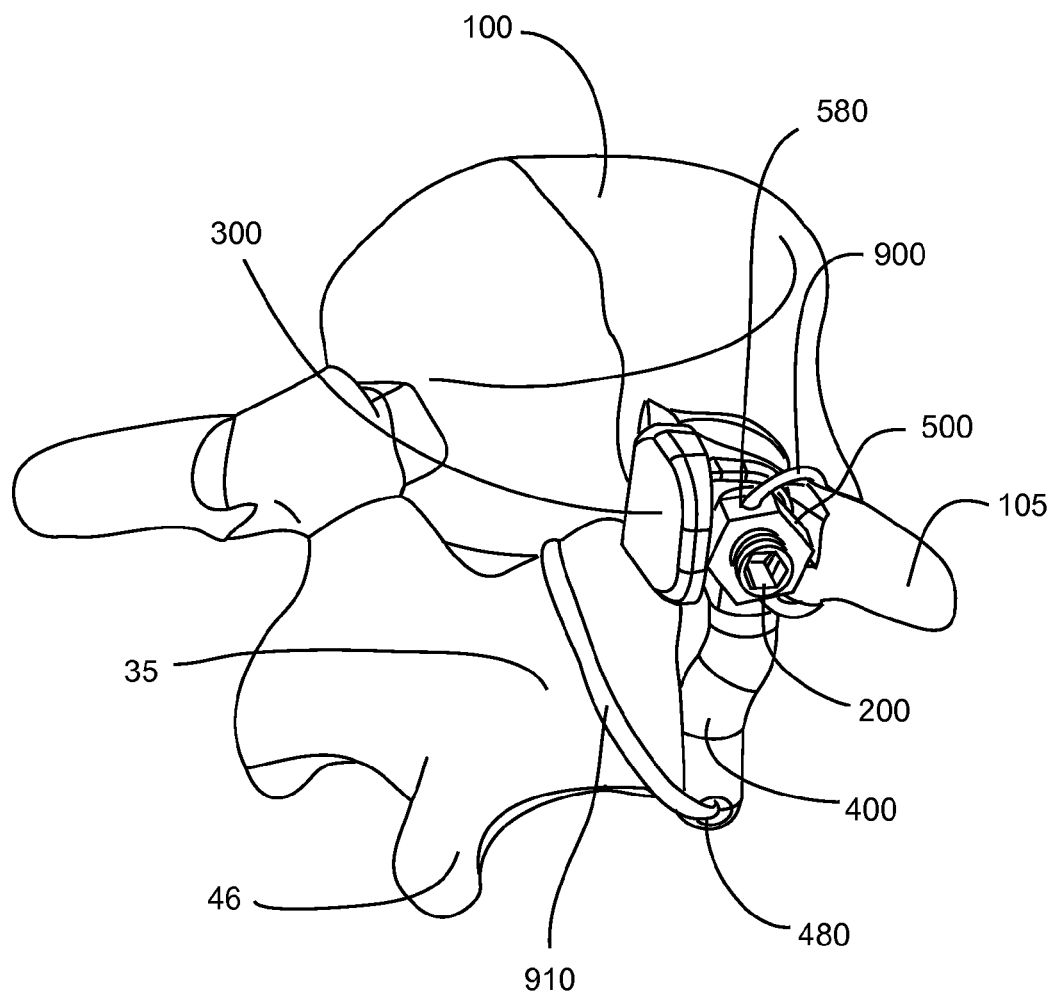
FIG. 45 shows superior and inferior facet prostheses held to a vertebra by flexible fixation elements.

FIG. 45 shows the superior facet prosthesis 300 and inferior facet prosthesis 400 held to the vertebra 100 by adjunctive flexible fixation element 900 and secondary flexible fixation element 910. These flexible fixation elements 900 and/or 910 may be made from such constructs as suture, braided cable, wire, ribbon, and other constructs that have longer lengths than cross-sections and withstand larger loads in tension than in compression. The flexible fixation element 900 and/or 910 may be manufactured from biocompatible metals, alloys such as cobalt chrome alloys, titanium alloys, stainless steel alloys, polymers, bioabsorbale materials, composites, or other materials that are biocompatible and can be formed into a flexible element structure 900 and/or 910 such as those shown in FIG. 45. The adjunctive flexible element 900 shown in FIG. 45 is shown attached to and securing the elongated head 500. A flexible element attachment portion 580 (e.g., including an opening) mates the flexible element 900 to the elongated head. However, the adjunctive flexible fixation element 900 may attach to and add adjunctive fixation element 900 to the fixation element 200, the superior facet prosthesis 300, the inferior facet prosthesis 400 or a combination of the above listed elements of the prosthesis. A flexible fixation attachment portion 480 (e.g., including an opening) in the inferior facet prosthesis 400 allows the secondary flexible fixation element 910 to secure the inferior facet prostheses 400 to the vertebra 100. The flexible fixation elements 900 and/or 910 may be secured to the vertebra 100 by physically wrapping around anatomic features such as the posterior arch 35, the spinous process 46, or transverse process 105 or a combination of these anatomic features. The flexible element 900 and secondary flexible element 910 may also be secured to the vertebra by bone anchors such as anchors designed to anchor flexible fixation elements (such as suture) to bone. Suture anchors such as threaded suture anchors, barbed suture anchors, toggle suture anchors or any other means of anchoring a flexible fixation element to bone may be used to anchor the flexible fixation element 900 or the secondary flexible fixation element 910 to the vertebra 100.

Figure 46:
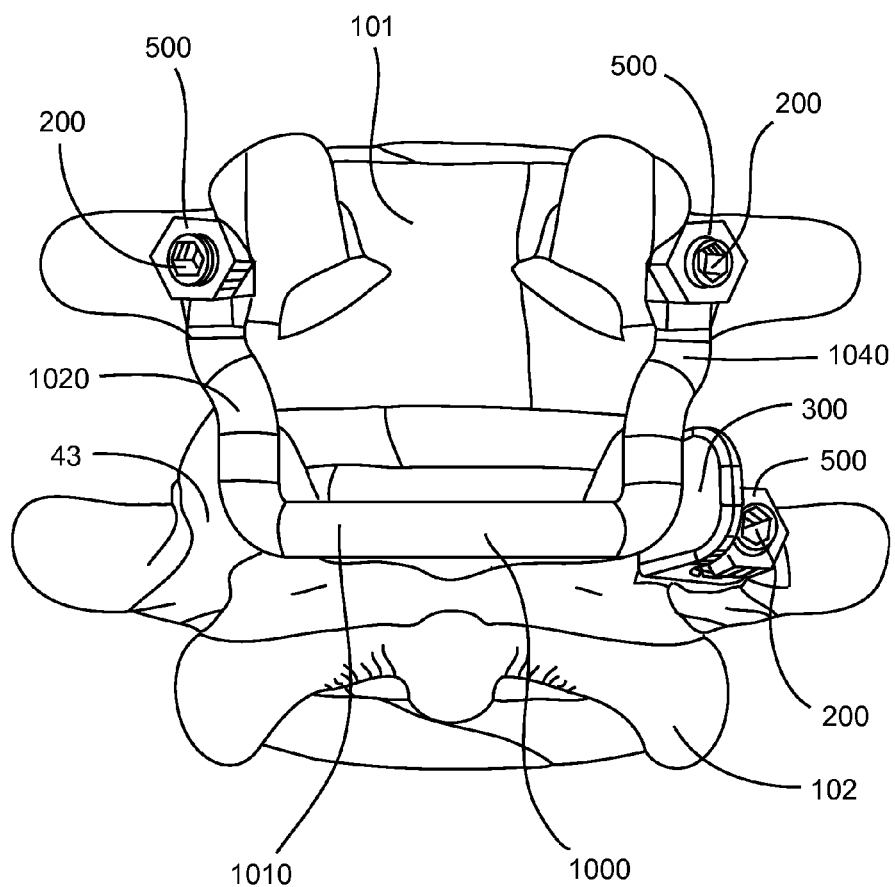
FIG. 46 is a dorsal view of a bilateral inferior implant.

FIG. 46 is a dorsal view of a bilateral inferior facet prosthesis 1000. The bilateral inferior facet prosthesis 1000 is a one-piece inferior facet prosthesis that has both a right inferior side 1040 and a left inferior side 1020 connected by a stabilizing bar 1010. Both the right inferior side 1040 and the left inferior side 1020 are designed to fix to the vertebra at the respective inferior resection surface 121 (FIG. 19) and the first resection surface 112. The bilateral inferior prosthesis is a design that allows replacement of both the left and the right inferior facet. In this embodiment, the bilateral inferior prosthesis is placed over the left and right fixation elements 200 which extend into the top vertebra 101. In this embodiment shown in FIG. 46, the right inferior side is articulating with a right superior facet prosthesis 300 attached to the lower vertebra 102. Also in this embodiment, the left inferior side 1020 is articulating with the left natural superior facet 43 of the lower vertebra 102. The stabilizing bar 1010 of the bilateral inferior prosthesis 1000 is designed to stabilize the left side 1020 and the right side 1040 so that they are secure.

Having described preferred embodiments of the invention with reference to the accompanying drawings, it is to be understood that the embodiments shown herein are by way of example, and that various changes and modifications may be effected by one skilled in the art without departing from the scope or spirit of the invention as defined in the following claims.

The invention claimed is:

1. A method for replacing at least a portion of a natural facet of a first vertebra, the method comprising:
    positioning a superior articular surface to articulate with an adjacent inferior articular surface on an adjacent upper vertebra;
    positioning an inferior articular surface at any of a plurality of orientations with respect to the superior articular surface to enable the inferior articular surface to articulate with an adjacent superior articular surface on an adjacent lower vertebra; and
    implanting a fixation member in the first vertebra to secure the positioned superior and inferior articular surfaces to the first vertebra,
    wherein the superior articular surface is incorporated into a superior prosthesis and the inferior articular surface is incorporated into an inferior prosthesis, wherein positioning the superior articular surface comprises positioning the superior prosthesis, wherein positioning the inferior articular surface comprises positioning the inferior prosthesis,
wherein at least one of positioning the superior prosthesis and positioning the inferior prosthesis is carried out such that after the corresponding prosthesis has been positioned, no portion of the corresponding prosthesis encircles a spinous process of the first vertebra.

2. The method of claim 1, wherein the steps of positioning the superior articular surface, positioning the inferior articular surface, and implanting the fixation member are all carried out independently from each other.

3. The method of claim 1, wherein at least one of positioning the superior prosthesis and positioning the inferior prosthesis is carried out such that after the corresponding prosthesis has been positioned, no portion of the corresponding prosthesis contacts a lamina of the first vertebra.

4. The method of claim 1, wherein positioning the inferior prosthesis is carried out such that after the inferior prosthesis has been positioned, the inferior prosthesis is free of contact with a posterior surface of a lamina of the first vertebra.

5. The method of claim 1, wherein implanting the fixation member in the first vertebra comprises implanting the fixation member in a pedicle of the first vertebra to secure both of the superior articular surface and the inferior articular surface to a single side of the first vertebra.

6. A method for replacing at least a portion of a natural facet of a first vertebra, the method comprising:
    positioning a superior articular surface to articulate with an adjacent inferior articular surface on an adjacent upper vertebra;
    positioning an inferior articular surface at any of a plurality of orientations with respect to the superior articular surface to enable the inferior articular surface to articulate with an adjacent superior articular surface on an adjacent lower vertebra; and
    implanting a fixation member in the first vertebra to secure the positioned superior and inferior articular surfaces to the first vertebra
    wherein the superior articular surface is incorporated into a superior prosthesis and the inferior articular surface is incorporated into an inferior prosthesis, wherein positioning the superior articular surface comprises positioning the superior prosthesis, wherein positioning the inferior articular surface comprises positioning the inferior prosthesis,
wherein each of the superior and inferior prostheses comprises an opening; the method further comprising passing a portion of the fixation member through the openings prior to implantation of the fixation member in the first vertebra.

7. The method of claim 6, wherein at least one of the superior and inferior prostheses comprises a flange through which the opening passes, wherein the corresponding superior or inferior articular surface is oriented perpendicular or nearly perpendicular to the flange.

8. A method for replacing at least a portion of a natural facet of a first vertebra, the method comprising:
    positioning a superior articular surface to articulate with an adjacent inferior articular surface on an adjacent upper vertebra;
    positioning an inferior articular surface at any of a plurality of orientations with respect to the superior articular surface to enable the inferior articular surface to articulate with an adjacent superior articular surface on an adjacent lower vertebra; and
    implanting a fixation member in the first vertebra to secure the positioned superior and inferior articular surfaces to the first vertebra,
    wherein the superior articular surface is incorporated into a superior prosthesis and the inferior articular surface is incorporated into an inferior prosthesis, wherein positioning the superior articular surface comprises positioning the superior prosthesis, wherein positioning the inferior articular surface comprises positioning the inferior prosthesis, further comprising securing an enlarged head to the fixation member to press portions of the superior and inferior prostheses against the first vertebra.

9. A method for replacing at least a portion of a natural facet of a first vertebra, the method comprising:

positioning a superior prosthesis having an opening such that a superior articular surface of the superior prosthesis is positioned to articulate with an adjacent inferior articular surface on an adjacent vertebra;

positioning an inferior prosthesis having an opening such that an inferior articular surface of the inferior prosthesis is positioned to articulate with an adjacent superior articular surface on an adjacent vertebra; and implanting a fixation member in the first vertebra to secure the positioned inferior and superior articular surfaces to the first vertebra by passing a portion of the fixation member through the openings, wherein the superior prosthesis, the inferior prosthesis, and the fixation member are separate pieces from each other.

10. The method of claim 9, wherein at least one of positioning the superior prosthesis and positioning the inferior prosthesis is carried out such that after the corresponding prosthesis has been positioned, no portion of the corresponding prosthesis contacts a lamina of the first vertebra.

11. The method of claim 9, wherein at least one of positioning the superior prosthesis and positioning the inferior prosthesis is carried out such that after the corresponding has been positioned, no portion of the corresponding prosthesis encircles a spinous process of the first vertebra.

12. The method of claim 9, wherein at least one of the superior and inferior prostheses comprises a flange through which the opening of the corresponding prosthesis passes, wherein the corresponding superior or inferior articular surface is oriented perpendicular or nearly perpendicular to the flange.

13. The method of claim 9, further comprising securing an enlarged head to the fixation member to press portions of the superior and inferior prostheses against the first vertebra.

14. The method of claim 9, wherein positioning the inferior prosthesis is carried out such that after the inferior prosthesis has been positioned, the inferior prosthesis is free of contact with a posterior surface of a lamina of the first vertebra.

15. The method of claim 9, wherein implanting the fixation member in the first vertebra comprises implanting the fixation member in a pedicle of the first vertebra to secure both the superior articular surface and inferior articular surface to a single side of the first vertebra.

* * * * *